(12) United States Patent
Zhang

(10) Patent No.: US 9,108,965 B2
(45) Date of Patent: Aug. 18, 2015

(54) MALONIC ACID DI-SALTS AND A METHOD FOR PREPARING MALONYL DIHALIDES

(71) Applicant: E I DU PONT DE NEMOURS AND COMPANY, Wilmington, DE (US)

(72) Inventor: Wenming Zhang, Newark, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/364,340

(22) PCT Filed: Dec. 13, 2012

(86) PCT No.: PCT/US2012/069468
§ 371 (c)(1),
(2) Date: Jun. 11, 2014

(87) PCT Pub. No.: WO2013/090547
PCT Pub. Date: Jun. 20, 2013

(65) Prior Publication Data
US 2014/0343284 A1   Nov. 20, 2014

Related U.S. Application Data

(60) Provisional application No. 61/570,962, filed on Dec. 15, 2011.

(51) Int. Cl.
*C07D 471/04* (2006.01)
*C07C 57/34* (2006.01)
(Continued)

(52) U.S. Cl.
CPC ............. *C07D 471/04* (2013.01); *C07C 51/60* (2013.01); *C07C 55/36* (2013.01); *C07C 57/34* (2013.01); *C07C 57/36* (2013.01); *C07D 213/55* (2013.01)

(58) Field of Classification Search
CPC .................................................. C07D 471/04
USPC ......................................................... 544/282
See application file for complete search history.

(56) References Cited

U.S. PATENT DOCUMENTS 5,358,924 A    10/1994   Kruger et al.
6,140,358 A    10/2000   Lieb et al.
(Continued)

FOREIGN PATENT DOCUMENTS

CN    1903851 A      1/2007
WO    97/36868 A1   10/1997
(Continued)

OTHER PUBLICATIONS

King, Med. Chem., Principle and Practice (1994), pp. 206-208.*
(Continued)

*Primary Examiner* — Taofiq A Solola
(74) *Attorney, Agent, or Firm* — Renee M Lett

(57) ABSTRACT

A compound of Formula 2 is disclosed

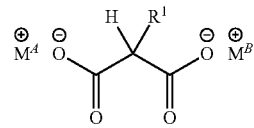

wherein $R^1$, $M^A$ and $M^B$ are as defined in the disclosure.
Also disclosed is a method for preparing a compound of Formula 1

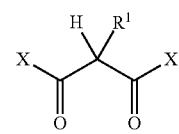

wherein $R^1$ and X are as defined in the disclosure comprising contacting a compound of Formula 2 with a halogenating agent.
Also disclosed is a method for preparing a compound of Formula 4

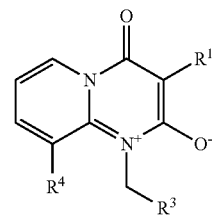

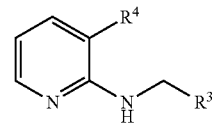

wherein $R^1$, $R^3$ and $R^4$ are as defined in the disclosure, comprising reacting a compound of Formula 5 wherein $R^3$ and $R^4$ are as defined in the disclosure with a compound of Formula 1, with a compound of Formula 1, the process of preparing the compound of Formula 4 includes the step of preparing the compound of Formula 1 from the compound of Formula 2 by the method disclosed above.
Also disclosed is compound that is methyl 3,5-dichlorobenzeneethanimidate methyl 3,5-dichlorobenzeneethanimidate or ethyl 3,5-dichlorobenzeneethanimidate or salts thereof.

13 Claims, No Drawings

(51) Int. Cl.
  *C07C 51/60* (2006.01)
  *C07C 55/36* (2006.01)
  *C07C 57/36* (2006.01)
  *C07D 213/55* (2006.01)

(56) References Cited

U.S. PATENT DOCUMENTS

| | | | |
|---|---|---|---|
| 8,552,007 | B2 | 10/2013 | Holyoke, Jr. et al. |
| 8,697,707 | B2 | 4/2014 | Holyoke, Jr. et al. |
| 8,722,690 | B2 | 5/2014 | Zhang et al. |
| 2003/0153728 | A1 | 8/2003 | Kolb et al. |
| 2004/0167329 | A1 | 8/2004 | Horwitz et al. |
| 2012/0122679 | A1 | 5/2012 | Zhang et al. |
| 2012/0122680 | A1 | 5/2012 | Holyoke, Jr. et al. |
| 2013/0190171 | A1 | 7/2013 | Pahutski, Jr. et al. |
| 2013/0338002 | A1 | 12/2013 | Holyoke, Jr. et al. |
| 2014/0187776 | A1 | 7/2014 | Holyoke, Jr. et al. |
| 2014/0206536 | A1 | 7/2014 | Zhang et al. |

FOREIGN PATENT DOCUMENTS

| | | |
|---|---|---|
| WO | 2009/099929 A1 | 8/2009 |
| WO | 2011/017334 A2 | 2/2011 |
| WO | 2011/017342 A2 | 2/2011 |
| WO | 2011/017347 A2 | 2/2011 |
| WO | 2011/017351 A2 | 2/2011 |
| WO | 2012/092115 A1 | 7/2012 |
| WO | 2012/106495 A1 | 8/2012 |

OTHER PUBLICATIONS

XP002696068, CAS registry No. 1196533-04-6, published Dec. 8, 2009.

XP002696069, CAS registry No. 1196155-85-7, published Dec. 8, 2009.

V. Aranyos et.al., "Electrochemical and Photoelectrochemical investigation of new carboxylatobipyridine (bis-bipyridine)ruthenium(II) Complexes for Dye-sensitized TiO2 Electrodes", Solar Energy Materials and Solar Cells 2000, vol. 64, pp. 97-114.

XP002696071 abstract of CN 1903851(Ma, Q.; Wang, J., "Preparation Method of 2-Substituted Calcium Malonate and Use of Calcium Salt".

G. Van Dyke Tiers, "Preparation of Acyl Halides and Esters from Salts of Perfluoroalkanoic Acids", J. Org. Chem. 1964, vol. 29, pp. 2038-2039.

\* cited by examiner

MALONIC ACID DI-SALTS AND A METHOD FOR PREPARING MALONYL DIHALIDES

BACKGROUND OF THE INVENTION

This invention relates to novel malonic acid di-salts. These di-salts are useful in the method of preparing certain malonyl di-halides which are, in turn, useful in preparing certain mesoionic insecticides (see e.g., PCT Publication WO 2009/99929 A1).

SUMMARY OF THE INVENTION

This invention relates to a compound of Formula 2

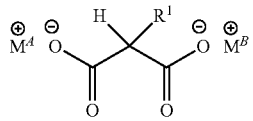

wherein
- $R^1$ is phenyl or pyridinyl, each optionally substituted with Q and up to 3 substituents independently selected from $R^2$; provided $R^1$ is substituted with at least one Q or one $R^2$;
- each $R^2$ is independently halogen, cyano, $SF_5$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;
- Q is phenyl or pyridinyl, each optionally substituted with up to 5 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy;
- each $M^A$ and $M^B$ is independently Li, Na, K, Ca, Ba or $N(R^A)(R^B)(R^C)(R^D)$; and
- each $R^A$, $R^B$, $R^C$ and $R^D$ is independently H, $C_1$-$C_4$ alkyl, cyclohexyl, phenyl or benzyl.

This invention provides a method for preparing a compound of Formula 1

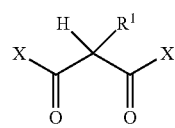

wherein
- $R^1$ is phenyl or pyridinyl, each optionally substituted with Q and up to 3 substituents independently selected from $R^2$;
- each $R^2$ is independently halogen, cyano, $SF_5$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;
- Q is phenyl or pyridinyl, each optionally substituted with up to 5 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy; and
- X is Cl or Br comprising contacting a compound of Formula 2

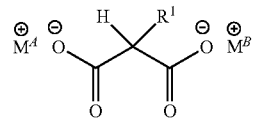

wherein
- $R^1$ is phenyl or pyridinyl, each optionally substituted with Q and up to 3 substituents independently selected from $R^2$;
- each $R^2$ is independently halogen, cyano, $SF_5$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;
- Q is phenyl or pyridinyl, each optionally substituted with up to 5 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy;
- each $M^A$ and $M^B$ is independently Li, Na, K, Ca, Ba or $N(R^A)(R^B)(R^C)(R^D)$; and
- each $R^A$, $R^B$, $R^C$ and $R^D$ is independently H, $C_1$-$C_4$ alkyl, cyclohexyl, phenyl or benzyl with a halogenating agent.

This invention also provides a method for preparing a compound of Formula 4

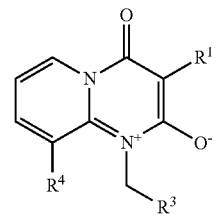

wherein
- $R^1$ is phenyl or pyridinyl, each optionally substituted with Q and up to 3 substituents independently selected from $R^2$;
- each $R^2$ is independently halogen, cyano, $SF_5$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;
- Q is phenyl or pyridinyl, each optionally substituted with up to 5 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy;

R³ is thiazolyl, pyridinyl or pyrimidinyl, each optionally substituted with halogen or C₁-C₄ alkyl; and
R⁴ is H, C₁-C₄ alkyl or C₁-C₄ haloalkyl
comprising reacting a compound of Formula 5

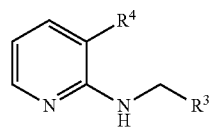

wherein
R³ is thiazolyl, pyridinyl or pyrimidinyl, each optionally substituted with halogen or C₁-C₄ alkyl; and
R⁴ is H, C₁-C₄ alkyl or C₁-C₄ haloalkyl
with a compound of Formula 1, the process of preparing the compound of Formula 4 includes the step of preparing the compound of Formula 1 from the compound of Formula 2 by the method disclosed above.

This invention also provides a compound that is methyl 3,5-dichlorobenzeneethanimidate or ethyl 3,5-dichlorobenzeneethanimidate or salts thereof.

DETAILED DESCRIPTION OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such phrase would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

In the context of the present disclosure, the terms "contact", "contacted" or "contacting" means bringing at least two chemical reagents together. The term describes this interaction which is intended to bring about a specific chemical transformation. For example in the Summary of the Invention, when a compound of Formula 2 is "contacted" with a halogenating agent, the two reagents are "reacted" to prepare a compound of Formula 1. This "contacting" may also be performed in the presence of additional reagents, solvents, catalysts and the like as described in the Summary of the Invention or any of the Embodiments herein.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkylene" denotes a straight-chain or branched alkanediyl. Examples of "alkylene" include CH₂, CH₂CH₂, CH(CH₃), CH₂CH₂CH₂, CH₂CH(CH₃) and the different butylene isomers. "Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include —CF₃, —CH₂Cl, —CH₂CF₃ and —CCl₂CF₃. The terms "haloalkoxy", "haloalkylthio", and the like, are defined analogously to the term "haloalkyl". Examples of "haloalkoxy" include —OCF₃, —OCH₂CCl₃, —OCH₂CH₂CF₂H and —OCH₂CF₃. Examples of "haloalkylthio" include —SCCl₃, —SCF₃, —SCH₂CCl₃ and —SCH₂CH₂CHCl As used herein, the term "alkylating agent" refers to a chemical compound in which a carbon-containing radical is bound through a carbon atom to leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of carbon-bound substituent radicals specified for R¹ and R². As used herein, the term "halogenating agent" refers to a chemical reagent that provides, inserts or places a halogen atom into (or onto) an organic molecule at a specified position through a variety of mechanisms.

Embodiments of the present invention include:
Embodiment 1. A compound of Formula 2

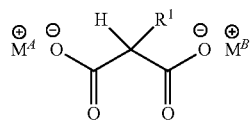

wherein
R¹ is phenyl or pyridinyl, each optionally substituted with Q and up to 3 substituents independently selected from R²; provided R¹ is substituted with at least one Q or one R²;
each R² is independently halogen, cyano, $SF_5$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;
Q is phenyl or pyridinyl, each optionally substituted with up to 5 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy;
each $M^A$ and $M^B$ is independently Li, Na, K, Ca, Ba or $N(R^A)(R^B)(R^C)(R^D)$; and
each $R^A$, $R^B$, $R^C$ and $R^D$ is independently H, $C_1$-$C_4$ alkyl, cyclohexyl, phenyl or benzyl.

Embodiment 2. A compound of Embodiment 1 wherein R¹ is phenyl optionally substituted with Q and up to 3 substituents independently selected from R².

Embodiment 3. A compound of any one of Embodiments 1 or 2 wherein R¹ is phenyl optionally substituted with up to 3 substituents independently selected from R².

Embodiment 4. A compound of any one of Embodiments 1 through 3 wherein R¹ is phenyl optionally substituted with up to 2 substituents independently selected from R².

Embodiment 5. A compound of any one of Embodiments 1 through 4 wherein R¹ is phenyl substituted with 1 substituent selected from R².

Embodiment 6. A compound of Embodiment 5 wherein R¹ is phenyl substituted with 1 substituent selected from R² at the 3-position.

Embodiment 7. A compound of Embodiment 6 wherein R¹ is 3-(trifluoromethyl)phenyl or 3-(trifluoromethoxy)phenyl.

Embodiment 8. A compound of any one of Embodiments 1 through 4 wherein R¹ is phenyl substituted with 2 substituents selected from R² at the 3- and 5-positions.

Embodiment 9. A compound of Embodiment 8 wherein R¹ is 3,5-dichlorophenyl or 3-chloro-5-(trifluoromethyl)phenyl.

Embodiment 10. A compound of any one of Embodiments 1 or 2 wherein R¹ is phenyl substituted with 1 substituent selected from Q.

Embodiment 11. A compound of Embodiment 10 wherein R¹ is phenyl substituted with one substituent selected from Q at the 3-position.

Embodiment 12. A compound of Embodiment 1 wherein R¹ is pyridinyl substituted with 1 to 2 substituents independently selected from R²; or pyridinyl substituted with 1 substituent selected from Q.

Embodiment 13. A compound of Embodiment 12 wherein R¹ is pyridinyl substituted with 1 to 2 substituents independently selected from R².

Embodiment 14. A compound of any one of Embodiments 1 through 13 wherein each R² is independently halogen, $C_1$-$C_4$ alkyl, $C_1$-$C_4$ haloalkyl, $C_1$-$C_4$ alkoxy or $C_1$-$C_4$ haloalkoxy.

Embodiment 15. A compound of Embodiment 14 wherein each R² is independently halogen, $C_1$-$C_2$ alkyl, $C_1$-$C_2$ haloalkyl, $C_1$-$C_2$ alkoxy or $C_1$-$C_2$ haloalkoxy.

Embodiment 16. A compound of Embodiment 15 wherein each R² is independently halogen, $C_1$-$C_2$ haloalkyl or $C_1$-$C_2$ haloalkoxy.

Embodiment 17. A compound of Embodiment 16 wherein each R² is independently $C_1$-$C_2$ haloalkyl or $C_1$-$C_2$ haloalkoxy.

Embodiment 18. A compound of Embodiment 16 wherein each R² is independently halogen or $C_1$-$C_2$ haloalkyl.

Embodiment 19. A compound of Embodiment 16 wherein each R² is independently Cl, —$CF_3$ or —$OCF_3$.

Embodiment 20. A compound of Embodiment 19 wherein each R² is independently Cl.

Embodiment 21. A compound of Embodiment 19 wherein each R² is independently Cl or —$CF_3$.

Embodiment 22. A compound of Embodiment 19 wherein each R² is independently —$CF_3$ or —$OCF_3$.

Embodiment 23. A compound of any one of Embodiments 1, 2, 10, 11 or 12 wherein Q is pyridinyl optionally substituted with up to 4 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy.

Embodiment 24. A compound of Embodiment 23 wherein Q is pyridinyl optionally substituted with up to 2 substituents independently selected from halogen and $C_1$-$C_4$ haloalkyl.

Embodiment 25. A compound of Embodiment 24 wherein Q is pyridinyl optionally substituted with 2 substituents independently selected from Cl and —$CF_3$.

Embodiment 26. A compound of Embodiment 25 wherein Q is 2-pyridinyl substituted with Cl and —$CF_3$.

Embodiment 27. A compound of Embodiment 26 wherein Q is 3-chloro-5-trifluoromethyl-pyridin-2-yl.

Embodiment 28. A compound of any one of Embodiments 1 through 27 wherein each $M^A$ and $M^B$ is independently Li, Na, K, $NH_4$, $NH(CH_2CH_3)_3$, $NH(CH_2CH_2CH_2CH_3)_3$, $NH_2(Bn)_2$, $NH_2(cyclohexyl)_2$ or $NH_2(phenyl)_2$.

Embodiment 29. A compound of Embodiment 28 wherein each $M^A$ and $M^B$ is independently Na, K, $NH_4$, $NH(CH_2CH_3)_3$ or $NH(CH_2CH_2CH_2CH_3)_3$.

Embodiment 30. A compound of Embodiment 28 wherein each $M^A$ and $M^B$ is independently Na, K, $NH_4$ or $NH(CH_2CH_3)_3$.

Embodiment 31. A compound of Embodiment 28 wherein each $M^A$ and $M^B$ is independently Na, K or $NH_4$.

Embodiment 32. A compound of Embodiment 31 wherein each $M^A$ and $M^B$ is independently Na or K.

Embodiment 33. A compound of Embodiment 31 wherein each $M^A$ and $M^B$ is independently Na.

Embodiment 34. A compound of Embodiment 31 wherein each $M^A$ and $M^B$ is independently K.

Embodiment 35. A compound of Embodiment 1 wherein R¹ is other than 3-(trifluoromethoxy)phenyl.

Embodiment 36. A compound of Embodiment 1 wherein R¹ is other than 2-fluorophenyl.

Embodiment 37. A compound of Embodiment 1 wherein R¹ is other than 2',3'-dichloro-[1,1'-biphenyl]-3-yl.

Embodiment 38. A compound of Embodiment 1 wherein R¹ is other than 3-(trifluoromethyl)phenyl.

Embodiment 39. A compound of Embodiment 1 wherein R¹ is other than 3-[3-chloro-5-(trifluoromethyl)-2-pyridinyl]phenyl.

Embodiment 40. A compound of any one of Embodiments 35 through 38 wherein and each $M^A$ and $M^B$ is independently other than Na.

Embodiment 41. A compound of Embodiment 7 wherein R¹ is 3-(trifluoromethyl)phenyl.

Embodiment 42. A compound of Embodiment 9 wherein R¹ is 3,5-dichlorophenyl.

Embodiment 1A. A method for preparing a compound of Formula 1

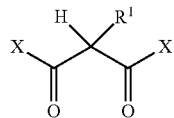

wherein
R¹ is phenyl or pyridinyl, each optionally substituted with Q and up to 3 substituents independently selected from R²;
each R² is independently halogen, cyano, SF₅, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;
Q is phenyl or pyridinyl, each optionally substituted with up to 5 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy; and
X is Cl or Br
comprising contacting a compound of Formula 2

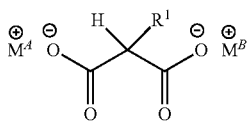

wherein
R¹ is phenyl or pyridinyl, each optionally substituted with Q and up to 3 substituents independently selected from R²;
each R² is independently halogen, cyano, SF₅, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;
Q is phenyl or pyridinyl, each optionally substituted with up to 5 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy;
each $M^A$ and $M^B$ is independently Li, Na, K, Ca, Ba or $N(R^A)(R^B)(R^C)(R^D)$; and
each $R^A$, $R^B$, $R^C$ and $R^D$ is independently H, $C_1$-$C_4$ alkyl, cyclohexyl, phenyl or benzyl
with a halogenating agent.
Embodiment 2A. The method of Embodiment 1A wherein R¹ is phenyl optionally substituted with Q and up to 3 substituents independently selected from R².
Embodiment 3A. The method of any one of Embodiments 1A or 2A wherein R¹ is phenyl optionally substituted with up to 3 substituents independently selected from R².
Embodiment 4A. The method of any one of Embodiment 1A through 3A wherein R¹ is phenyl optionally substituted with up to 2 substituents independently selected from R².
Embodiment 5A. The method of any one of Embodiments 1A through 4A wherein R¹ is phenyl substituted with 1 substituent selected from R².
Embodiment 6A. The method of Embodiment 5A wherein R¹ is phenyl substituted with 1 substituent selected from R² at the 3-position.
Embodiment 7A. The method of Embodiment 6A wherein R¹ is 3-(trifluoromethyl)phenyl or 3-(trifluoromethoxy)phenyl.
Embodiment 8A. The method of any one of Embodiments 1A through 4A wherein R¹ is phenyl substituted with 2 substituents selected from R² at the 3- and 5-positions.
Embodiment 9A. The method of Embodiment 8A wherein R¹ is 3,5-dichlorophenyl or 3-chloro-5-(trifluoromethyl)phenyl.
Embodiment 10A. The method of any one of Embodiments 1A or 2A wherein R¹ is phenyl substituted with 1 substituent selected from Q.
Embodiment 11A. A compound of Embodiment 10A wherein R¹ is phenyl substituted with one substituent selected from Q at the 3-position.
Embodiment 12A. The method of Embodiment 1A wherein R¹ is pyridinyl substituted with 1 to 2 substituents independently selected from R²; or pyridinyl substituted with 1 substituent selected from Q.
Embodiment 13A. The method of Embodiment 12A wherein R¹ is pyridinyl substituted with 1 to 2 substituents independently selected from R².
Embodiment 14A. The method of any one of Embodiments 1A through 13A wherein each R² is independently halogen, $C_1$-$C_4$ alkyl, $C_1$-$C_4$ haloalkyl, $C_1$-$C_4$ alkoxy or $C_1$-$C_4$ haloalkoxy.
Embodiment 15A. The method of Embodiment 14A wherein each R² is independently halogen, $C_1$-$C_2$ alkyl, $C_1$-$C_2$ haloalkyl, $C_1$-$C_2$ alkoxy or $C_1$-$C_2$ haloalkoxy.
Embodiment 16A. The method of Embodiment 15A wherein each R² is independently halogen, $C_1$-$C_2$ haloalkyl or $C_1$-$C_2$ haloalkoxy.
Embodiment 17A. The method of Embodiment 16A wherein each R² is independently $C_1$-$C_2$ haloalkyl or $C_1$-$C_2$ haloalkoxy.
Embodiment 18A. The method of Embodiment 16A wherein each R² is independently halogen or $C_1$-$C_2$ haloalkyl.
Embodiment 19A
The method of Embodiment 16A wherein each R² is independently Cl, —CF₃ or —OCF₃.
Embodiment 20A. The method of Embodiment 19A wherein each R² is independently Cl.
Embodiment 21A. The method of Embodiment 19A wherein each R² is independently Cl or —CF₃.
Embodiment 22A. The method of Embodiment 19A wherein each R² is independently —CF₃ or —OCF₃.
Embodiment 23A. The method of any one of Embodiments 1A, 2A, 10A, 11A or 12A wherein Q is pyridinyl optionally substituted with up to 4 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy.
Embodiment 24A. The method of Embodiment 23A wherein Q is pyridinyl optionally substituted with up to 2 substituents independently selected from halogen and $C_1$-$C_4$ haloalkyl.
Embodiment 25A. The method of Embodiment 24A wherein Q is pyridinyl optionally substituted with 2 substituents independently selected from Cl and —CF₃.
Embodiment 26A. The method of Embodiment 25A wherein Q is 2-pyridinyl substituted with Cl and —CF₃.
Embodiment 27A. The method of Embodiment 24A wherein Q is 3-chloro-5-trifluoromethyl-pyridin-2-yl.
Embodiment 28A. The method of any one of Embodiments 1A through 27A wherein each $M^A$ and $M^B$ is independently Li, Na, K, $NH_4$, $NH(CH_2CH_3)_3$, $NH(CH_2CH_2CH_2CH_3)_3$, $NH_2(Bn)_2$, $NH_2(cyclohexyl)$, or $NH_2(phenyl)_2$.

Embodiment 29A. A compound of Embodiment 28A wherein each $M^A$ and $M^B$ is independently Na, K, $NH_4$, $NH(CH_2CH_3)_3$ or $NH(CH_2CH_2CH_2CH_3)_3$.

Embodiment 30A. A compound of Embodiment 28A wherein each $M^A$ and $M^B$ is independently Na, K, $NH_4$ or $NH(CH_2CH_3)_3$.

Embodiment 31A. The method of Embodiment 28A wherein each $M^A$ and $M^B$ is independently Na, K or $NH_4$.

Embodiment 32A. The method of Embodiment 28A wherein each $M^A$ and $M^B$ is independently Na or K.

Embodiment 33A. The method of Embodiment 28A wherein each $M^A$ and $M^B$ is independently Na.

Embodiment 34A. The method of Embodiment 28A wherein each $M^A$ and $M^B$ is independently K.

Embodiment 35A. The method of any one of Embodiments 1A through 34A wherein the halogenating agent is oxalyl chloride, thionyl chloride, phosgene, triphosgene, cyanuric chloride, phosphorous oxychloride, phosphorous trichloride, phosphorous pentachloride, diphosgene, sulfuryl chloride, thionyl bromide, triphenylphosphine dibromide or phosphorous tribromide.

Embodiment 36A. The method of Embodiment 35A wherein the halogenating agent is oxalyl chloride, thionyl chloride, phosgene, triphosgene or cyanuric chloride.

Embodiment 37A. The method of Embodiment 36A wherein the halogenating agent is oxalyl chloride or thionyl chloride.

Embodiment 38A. The method of Embodiment 37A wherein the halogenating agent is oxalyl chloride.

Embodiment 39A. The method of any one of Embodiments 1A through 38A wherein the contacting is performed in the presence of pyridine or a compound of Formula 3

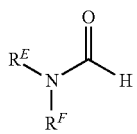

3 wherein
$R^E$ is $C_1$-$C_4$ alkyl;
$R^F$ is $C_1$-$C_4$ alkyl; or
$R^E$ and $R^F$ are taken together as $C_4$-$C_6$ alkylene.

Embodiment 40A. The method of Embodiment 39A wherein the contacting is performed in the presence of pyridine.

Embodiment 41A. The method of Embodiment 40A wherein $R^E$ is —$CH_3$; and $R^F$ is —$CH_3$.

Embodiment 42A. The method of Embodiment 39A wherein $R^E$ and $R^F$ are taken together as $C_5$ alkylene.

Embodiment 43A. The method of any one of Embodiments 1A through 42A wherein the molar ratio of pyridine or the compound of Formula 3 to the compound of Formula 2 is about 0.001 to about 0.5.

Embodiment 44A. The method of Embodiment 43A wherein the molar ratio of pyridine or the compound of Formula 3 to the compound of Formula 2 is about 0.001 to about 0.4.

Embodiment 45A. The method of Embodiment 44A wherein the molar ratio of pyridine or the compound of Formula 3 to the compound of Formula 2 is about 0.005 to about 0.3.

Embodiment 46A. The method of Embodiment 45A wherein the molar ratio of pyridine or the compound of Formula 3 to the compound of Formula 2 is about 0.005 to about 0.2.

Embodiment 47A. The method of Embodiment 46A wherein the molar ratio of pyridine or the compound of Formula 3 to the compound of Formula 2 is about 0.005 to about 0.1.

Embodiment 48A. The method of any one of Embodiments 1A through 47A wherein the contacting is performed in an organic solvent.

Embodiment 49A. The method of Embodiment 48A wherein the organic solvent is toluene, dichloromethane, cyclohexane, benzene, 1,2-dichloroethane, ethyl acetate or butyl acetate.

Embodiment 50A. The method of Embodiment 49A wherein the organic solvent is toluene, dichloromethane or cyclohexane.

Embodiment 51A. The method of Embodiment 50A wherein the organic solvent is toluene.

Embodiment 52A. The method of any one of Embodiments 1A through 51A wherein the contacting is performed at a temperature up to about 200° C.

Embodiment 53A. The method of Embodiment 52A wherein the contacting is performed at a temperature from about 0 to about 200° C.

Embodiment 54A. The method of Embodiment 53A wherein the contacting is performed at a temperature from about 0 to about 100° C.

Embodiment 55A. The method of Embodiment 54A wherein the contacting is performed at a temperature from about 0 to about 70° C.

Embodiment 56A. The method of Embodiment 55A wherein the contacting is performed at a temperature from about 18 to about 30° C.

Embodiment 57A. The method of Embodiment 52A wherein the contacting is performed at a temperature from about 45 to about 55° C.

Embodiment 58A. The method of any one of Embodiments 1A through 57A wherein the contacting is performed by adding a compound of Formula 2 to the halogenating agent.

Embodiment 59A. The method of any one of Embodiments 1A through 57A wherein the contacting is performed by adding the halogenating agent to a compound of Formula 2.

Embodiment 60A. The method of any one of Embodiments 1A through 59A wherein the compound of Formula 1 is optionally isolated.

Embodiment 61A. The method of Embodiment 60A wherein the compound of Formula 1 is isolated.

Embodiment 62A. The method of Embodiment 60A wherein the compound of Formula 1 is other than isolated (i.e. used in-situ in the organic solvent).

Embodiment 63A. The method of any one of Embodiments 1A through 34A wherein the halogenating agent is a chlorinating agent or brominating agent.

Embodiment 64A. The method of Embodiment 63A wherein the chlorinating agent is oxalyl chloride, thionyl chloride, phosgene, triphosgene, cyanuric chloride, phosphorous oxychloride, phosphorous trichloride, phosphorous pentachloride, diphosgene or sulfuryl chloride.

Embodiment 65A. The method of Embodiment 63A wherein the brominating agent is thionyl bromide, triphenylphosphine dibromide or phosphorous tribromide.

Embodiment 66A. The method of any one of Embodiments 1A through 34A wherein X is Cl.

Embodiment 67A. The method of any one of Embodiments 1A through 34A wherein X is Br.

Embodiment 68A. A compound of Embodiment 7A wherein $R^1$ is 3-(trifluoromethyl)phenyl.

Embodiment 69A. A compound of Embodiment 9A wherein $R^1$ is 3,5-dichlorophenyl.

Embodiment 1B. A method of preparing a compound of Formula 4

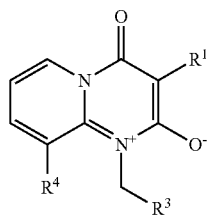

4 wherein
$R^1$ is phenyl or pyridinyl, each optionally substituted with Q and up to 3 substituents independently selected from $R^2$;
each $R^2$ is independently halogen, cyano, $SF_5$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;
Q is phenyl or pyridinyl, each optionally substituted with up to 5 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy;
$R^3$ is thiazolyl, pyridinyl or pyrimidinyl, each optionally substituted with halogen or $C_1$-$C_4$ alkyl; and
$R^4$ is H, $C_1$-$C_4$ alkyl or $C_1$-$C_4$ haloalkyl
comprising preparing a compound of Formula 1

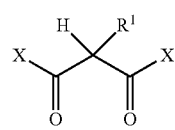

1 wherein
$R^1$ is phenyl or pyridinyl, each optionally substituted with Q and up to 3 substituents independently selected from $R^2$;
each $R^2$ is independently halogen, cyano, $SF_5$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;
Q is phenyl or pyridinyl, each optionally substituted with up to 5 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy; and
X is Cl or Br
by contacting a compound of Formula 2

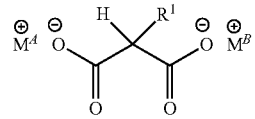

2 wherein
$R^1$ is phenyl or pyridinyl, each optionally substituted with Q and up to 3 substituents independently selected from $R^2$;
each $R^2$ is independently halogen, cyano, $SF_5$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;
Q is phenyl or pyridinyl, each optionally substituted with up to 5 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy;
each $M^A$ and $M^B$ is independently Li, Na, K, Ca, Ba or $N(R^A)(R^B)(R^C)(R^D)$; and
each $R^A$, $R^B$, $R^C$ and $R^D$ is independently H, $C_1$-$C_4$ alkyl, cyclohexyl, phenyl or benzyl
with a halogenating agent to produce a compound of Formula 1; and
reacting a compound of Formula 5

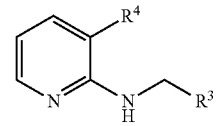

5 wherein
$R^3$ is thiazolyl, pyridinyl or pyrimidinyl, each optionally substituted with halogen or $C_1$-$C_4$ alkyl; and
$R^4$ is H, $C_1$-$C_4$ alkyl or $C_1$-$C_4$ haloalkyl
with the compound of Formula 1 to prepare the compound of Formula 4.

Embodiment 2B. A method for preparing a compound of Formula 4

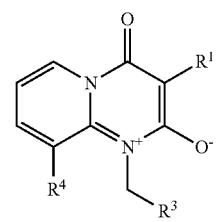

4 wherein
$R^1$ is phenyl or pyridinyl, each optionally substituted with Q and up to 3 substituents independently selected from $R^2$;
each $R^2$ is independently halogen, cyano, $SF_5$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;

Q is phenyl or pyridinyl, each optionally substituted with up to 5 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy;

$R^3$ is thiazolyl, pyridinyl or pyrimidinyl, each optionally substituted with halogen or $C_1$-$C_4$ alkyl; and $R^4$ is H, $C_1$-$C_4$ alkyl or $C_1$-$C_4$ haloalkyl comprising reacting a compound of Formula 5

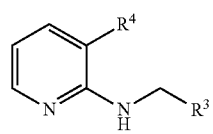

wherein $R^3$ is thiazolyl, pyridinyl or pyrimidinyl, each optionally substituted with halogen or $C_1$-$C_4$ alkyl; and $R^4$ is H, $C_1$-$C_4$ alkyl or $C_1$-$C_4$ haloalkyl with a compound of Formula 1

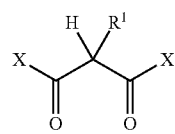

where the compound of Formula 1 is prepared by the method of Embodiment 1A.

Embodiment 3B. The method of preparing a compound of Formula 4 comprising reacting a compound of Formula 5 with a compound of Formula 1; the method characterized by preparing the compound of Formula 1 from the compound of Formula 2 by the method disclosed above, as described in the Summary of the Invention.

Embodiment 4B. The method of any one of Embodiments 1B through 3B wherein $R^1$ is phenyl optionally substituted with Q and up to 3 substituents independently selected from $R^2$.

Embodiment 5B. The method of any one of Embodiments 1B through 4B wherein $R^1$ is phenyl optionally substituted with up to 3 substituents independently selected from $R^2$.

Embodiment 6B. The method of any one of Embodiment 1B through 5B wherein $R^1$ is phenyl optionally substituted with up to 2 substituents independently selected from $R^2$.

Embodiment 7B. The method of any one of Embodiments 1B through 6B wherein $R^1$ is phenyl substituted with 1 substituent selected from $R^2$.

Embodiment 8B. The method of Embodiment 7B wherein $R^1$ is phenyl substituted with 1 substituent selected from $R^2$ at the 3-position.

Embodiment 9B. The method of Embodiment 8B wherein $R^1$ is 3-(trifluoromethyl)phenyl or 3-(trifluoromethoxy) phenyl.

Embodiment 10B. The method of any one of Embodiments 1B through 6B wherein $R^1$ is phenyl substituted with 2 substituents selected from $R^2$ at the 3- and 5-positions.

Embodiment 11B. The method of Embodiment 10B wherein $R^1$ is 3,5-dichlorophenyl or 3-chloro-5-(trifluoromethyl)phenyl.

Embodiment 12B. The method of any one of Embodiments 1B through 4B wherein $R^1$ is phenyl substituted with 1 substituent selected from Q.

Embodiment 13B. The method of Embodiment 12B wherein $R^1$ is phenyl substituted with one substituent selected from Q at the 3-position.

Embodiment 14B. The method of any one of Embodiments 1B through 3B wherein $R^1$ is pyridinyl substituted with 1 to 2 substituents independently selected from $R^2$; or pyridinyl substituted with 1 substituent selected from Q.

Embodiment 15B. The method of Embodiment 14B wherein $R^1$ is pyridinyl substituted with 1 to 2 substituents independently selected from $R^2$.

Embodiment 16B. The method of any one of Embodiments 1B through 15B wherein each $R^2$ is independently halogen, $C_1$-$C_4$ alkyl, $C_1$-$C_4$ haloalkyl, $C_1$-$C_4$ alkoxy or $C_1$-$C_4$ haloalkoxy.

Embodiment 17B. The method of Embodiment 16B wherein each $R^2$ is independently halogen, $C_1$-$C_2$ alkyl, $C_1$-$C_2$ haloalkyl, $C_1$-$C_2$ alkoxy or $C_1$-$C_2$ haloalkoxy.

Embodiment 18B. The method of Embodiment 17B wherein each $R^2$ is independently halogen, $C_1$-$C_2$ haloalkyl or $C_1$-$C_2$ haloalkoxy.

Embodiment 19B. The method of Embodiment 18B wherein each $R^2$ is independently $C_1$-$C_1$ haloalkyl or $C_1$-$C_2$ haloalkoxy.

Embodiment 20B. The method of Embodiment 18B wherein each $R^2$ is independently halogen or $C_1$-$C_2$ haloalkyl.

Embodiment 21B. The method of Embodiment 18B wherein each $R^2$ is independently Cl, —$CF_3$ or —$OCF_3$.

Embodiment 22B. The method of Embodiment 21B wherein each $R^2$ is independently Cl.

Embodiment 23B. The method of Embodiment 21B wherein each $R^2$ is independently Cl or —$CF_3$.

Embodiment 24B. The method of Embodiment 21B wherein each $R^2$ is independently —$CF_3$ or —$OCF_3$.

Embodiment 25B. The method of any one of Embodiments 1B, 2B, 3B, 4B, 12B, 13B or 14B wherein Q is pyridinyl optionally substituted with up to 4 substituents independently selected from halogen, cyano, $C_1$-$C_4$ alkyl, $C_1$-$C_4$ haloalkyl, $C_1$-$C_4$ alkoxy and $C_1$-$C_4$ haloalkoxy.

Embodiment 26B. The method of Embodiment 25B wherein Q is pyridinyl optionally substituted with up to 2 substituents independently selected from halogen and $C_1$-$C_4$ haloalkyl.

Embodiment 27B. The method of Embodiment 26B wherein Q is pyridinyl optionally substituted with 2 substituents independently selected from Cl and —$CF_3$.

Embodiment 28B. The method of Embodiment 27B wherein Q is 2-pyridinyl substituted with Cl and —$CF_3$.

Embodiment 29B. The method of Embodiment 29B wherein Q is 3-chloro-5-trifluoromethyl-pyridin-2-yl.

Embodiment 30B. The method any one of Embodiments 1B through 29B wherein $R^3$ is thiazolyl or pyrimidinyl, each optionally substituted with halogen or $C_1$-$C_2$ alkyl.

Embodiment 31B. The method of Embodiment 30B wherein $R^3$ is thiazolyl optionally substituted with halogen or $C_1$-$C_1$ alkyl.

Embodiment 32B. The method of Embodiment 31B wherein $R^3$ is thiazolyl optionally substituted with halogen.

Embodiment 33B. The method of Embodiment 32B wherein $R^3$ is 5-thiazolyl optionally substituted with halogen.

Embodiment 34B. The method of Embodiment 33B wherein $R^3$ is 2-chloro-5-thiazolyl.

Embodiment 35B. The method of Embodiment 30B wherein $R^3$ is pyrimidinyl optionally substituted with halogen or $C_1$-$C_4$ alkyl.

Embodiment 36B. The method of Embodiment 35B wherein $R^3$ is pyrimidinyl (i.e. unsubstituted).

Embodiment 37B. The method of Embodiment 36B wherein $R^3$ is 5-pyrimidinyl (i.e. unsubstituted).

Embodiment 38B. The method of any one of Embodiments 1B through 37B wherein $R^4$ is H or $C_1$-$C_4$ alkyl.

Embodiment 39B. The method of Embodiment 38B wherein $R^4$ is H or $CH_3$.

Embodiment 40B. The method of Embodiment 39B wherein $R^4$ is H.

Embodiment 41B. The method of Embodiment 39B wherein $R^4$ is $CH_3$.

Embodiment 42B. The method of any one of Embodiments 1B through 41B wherein the reacting is performed in the presence of a base.

Embodiment 43B. The method of Embodiment 42B wherein the base is an organic base.

Embodiment 44B. The method of Embodiment 43B wherein the organic base is trimethylamine, triethylamine, tributylamine N,N-diisopropylethylamine, pyridine, 2-picoline, 3-picoline, 4-picoline or 2,6-lutidine.

Embodiment 45B. The method of Embodiment 44B wherein the organic base is triethylamine tributylamine pyridine or 4-picoline.

Embodiment 46B. The method of Embodiment 45B wherein the organic base is triethylamine or 4-picoline.

Embodiment 47B. The method of Embodiment 46B wherein the organic base is triethylamine.

Embodiment 48B. The method of Embodiment 46B wherein the organic base is 4-picoline.

Embodiment 49B. The method of any one of Embodiments 40B through 48B wherein the molar ratio of the base to a compound of Formula 1 is about 1 to about 10.

Embodiment 50B. The method of Embodiment 49B wherein the molar ratio of the base to a compound of Formula 1 is about 1 to about 5.

Embodiment 51B. The method of Embodiment 50B wherein the molar ratio of the base to a compound of Formula 1 is about 1.8 to about 2.5.

Embodiment 52B. The method of Embodiment 50B wherein the molar ratio of the base to a compound of Formula 1 is about 1.5 to about 3.5.

Embodiment 53B. The method of Embodiment 52B wherein the molar ratio of the base to a compound of Formula 1 is about 2 to about 3.5.

Embodiment 54B. The method of Embodiment 53B wherein the molar ratio of the base to a compound of Formula 1 is about 2 to about 3.25.

Embodiment 55B. The method of any one of Embodiments 42B through 54B wherein the molar ratio of the base to a compound of Formula 1 is at least about 2.

Embodiment 56B. The method of any one of Embodiments 1B through 59B wherein the contacting is performed in a solvent.

Embodiment 57B. The method of Embodiment 56B wherein the solvent is toluene, dichloromethane, cyclohexane, benzene, 1,2-dichloroethane, ethyl acetate or butyl acetate, or a mixture thereof.

Embodiment 58B. The method of Embodiment 57B wherein the solvent is toluene.

Embodiment 59B. The method of 57B wherein the solvent is a mixture of toluene and ethyl acetate.

Embodiment 60B. The method of 57B wherein the solvent is a mixture of toluene and butyl acetate.

Embodiment 61B. A compound of Embodiment 9B wherein $R^1$ is 3-(trifluoromethyl)phenyl.

Embodiment 62B. A compound of Embodiment 11B wherein $R^1$ is 3,5-dichlorophenyl.

Embodiment 1C. A compound that is methyl 3,5-dichlorobenzeneethanimidate or ethyl 3,5-dichlorobenzeneethanimidate or salts thereof.

Embodiment 2C. A compound of Embodiment 1C that is methyl 3,5-dichlorobenzeneethanimidate or a salt thereof.

Embodiment 3C. A compound of Embodiment 2C that is methyl 3,5-dichlorobenzeneethanimidate hydrochloride (1:1).

Combinations of Embodiments 1 through 42 of the present invention include:

Embodiment A. A compound of Formula 2 of Embodiment 1 wherein
  $R^1$ is phenyl optionally substituted with Q and up to 3 substituents independently selected from $R^2$;
  each $R^2$ is independently halogen, $C_1$-$C_4$ alkyl, $C_1$-$C_4$ haloalkyl, $C_1$-$C_4$ alkoxy or $C_1$-$C_4$ haloalkoxy;
  Q is pyridinyl optionally substituted with up to 2 substituents independently selected from halogen and $C_1$-$C_4$ haloalkyl; and
  each $M^A$ and $M^B$ is independently Li, Na, K, $NH_4$, $NH(CH_2CH_3)_3$, $NH(CH_2CH_2CH_3)_3$, $NH_2(Bn)_2$, $NH_2(cyclohexyl)_2$ or $NH_2(phenyl)_2$.

Embodiment B. A compound of Embodiment A wherein
  $R^1$ is phenyl optionally substituted with up to 2 substituents independently selected from $R^2$;
  each $R^2$ is independently halogen, $C_1$-$C_2$ alkyl, $C_1$-$C_2$ haloalkyl, $C_1$-$C_2$ alkoxy or $C_1$-$C_2$ haloalkoxy; and
  each $M^A$ and $M^B$ is independently Na, K, $NH_4$ or $NH(CH_2CH_3)_3$.

Embodiment C. A compound of Embodiment B wherein
  $R^1$ is phenyl substituted with 2 substituents selected from $R^2$ at the 3- and 5-positions;
  each $R^2$ is independently Cl or —$CF_3$; and
  each $M^A$ and $M^B$ is independently Na, K or $NH_4$.

Embodiment D. A compound of Embodiment B wherein
  $R^1$ is phenyl substituted with 1 substituent selected from $R^2$ at the 3-position;
  each $R^2$ is independently —$CF_3$ or —$OCF_3$; and
  each $M^A$ and $M^B$ is independently Na, K or $NH_4$.

Combinations of Embodiments 1A through 69A of the present invention include:

Embodiment AA. A method for preparing a compound of Formula 1 as described Embodiment 1A wherein
  $R^1$ is phenyl optionally substituted with Q and up to 3 substituents independently selected from $R^2$;
  each $R^2$ is independently halogen, $C_1$-$C_4$ alkyl, $C_1$-$C_4$ haloalkyl, $C_1$-$C_4$ alkoxy or $C_1$-$C_4$ haloalkoxy;
  Q is pyridinyl optionally substituted with up to 2 substituents independently selected from halogen and $C_1$-$C_4$ haloalkyl; and
  each $M^A$ and $M^B$ is independently Li, Na, K, $NH_4$, $NH(CH_2CH_3)_3$, $NH(CH_2CH_2CH_3)_3$, $NH_2(Bn)_2$, $NH_2(cyclohexyl)_2$ or $NH_2(phenyl)_2$.

Embodiment BB. The method of Embodiment AA wherein
  $R^1$ is phenyl optionally substituted with up to 2 substituents independently selected from $R^2$;
  each $R^2$ is independently halogen, $C_1$-$C_2$ alkyl, $C_1$-$C_2$ haloalkyl, $C_1$-$C_2$ alkoxy or $C_1$-$C_2$ haloalkoxy; and
  each $M^A$ and $M^B$ is independently Na, K, $NH_4$, $NH(CH_2CH_3)_3$ or $NH(CH_2CH_2CH_3)_3$.

Embodiment CC. The method of Embodiment BB wherein
the halogenating agent is oxalyl chloride, thionyl chloride, phosgene, triphosgene, cyanuric chloride, phosphorous oxychloride, phosphorous trichloride, phosphorous pentachloride, diphosgene, sulfuryl chloride, thionyl bromide, triphenylphosphine dibromide or phosphorous tribromide;
the contacting is performed in an organic solvent; and
X is Cl or Br.

Embodiment DD. The method of Embodiment CC wherein
the halogenating agent is oxalyl chloride, thionyl chloride, phosgene, triphosgene or cyanuric chloride;
X is Cl; and
the organic solvent is toluene, dichloromethane, cyclohexane, benzene, 1,2-dichloroethane, ethyl acetate or butyl acetate.

Combinations of Embodiments 1B through 62B of the present invention include:

Embodiment EE. The method for preparing a compound of Formula 4 as described in any one of Embodiments 1B, 2B or 3B wherein
$R^1$ is phenyl optionally substituted with Q and up to 3 substituents independently selected from $R^2$;
each $R^2$ is independently halogen, $C_1$-$C_4$ alkyl, $C_1$-$C_4$ haloalkyl, $C_1$-$C_4$ alkoxy or $C_1$-$C_4$ haloalkoxy;
Q is pyridinyl optionally substituted with up to 2 substituents independently selected from halogen and $C_1$-$C_4$ haloalkyl;
$R^3$ is thiazolyl or pyrimidinyl, each optionally substituted with halogen or $C_1$-$C_2$ alkyl; and
$R^4$ is H or $C_1$-$C_4$ alkyl.

Embodiment FF. The method of Embodiment EE wherein
$R^1$ is phenyl optionally substituted with up to 2 substituents independently selected from $R^2$;
each $R^2$ is independently Cl or —$CF_3$;
$R^3$ is 2-chloro-5-thiazolyl; and
$R^4$ is $CH_3$.

Embodiment GG. The method of Embodiment EE wherein
$R^1$ is phenyl substituted with 1 substituent selected from $R^2$;
each $R^2$ is independently —$CF_3$ or —$OCF_3$;
$R^3$ is 5-pyrimidinyl; and
$R_4$ is H.

Embodiments of this invention, including Embodiments 1 through 42, 1A through 69A, 1B through 62B, and A-GG above as well as any other embodiments described herein, can be combined in any manner. Moreover, the descriptions of variables in the embodiments pertain not only to the compounds of Formulas 1 through 5, but also to the starting compounds and intermediate compounds useful for preparing the compounds of Formulae 1 through 5 (i.e. 1b, 2a, 6, 6a, 7, 8, 9, 10, 11 and 11a, 1a and 5a. In addition, embodiments of this invention, including Embodiments 1 through 54 above as well as any other embodiments described herein, and any combination thereof, pertain to any of the methods of the present invention.

Malonic acids used in the preparation of a compound of Formula 2 can be unstable on standing or in storage (alone or as a solution in a suitable solvent) on account of the tendency of at least one of the two "—$CO_2H$" moieties to decarboxylate, thus generating $CO_{2(g)}$. Formation of $CO_{2(g)}$ is undesirable since it can cause unwanted build-up of pressure in any storage container creating a hazardous situation. Furthermore, partial decarboxylation of malonic acids (i.e. decarboxylation of at least one of the two "—$CO_2H$" moieties) introduces an impurity (i.e. the acetic acid) into the reagent. When the impurity is carried through during the preparation of a compound of Formula 2 it is difficult to remove from the desired product component. Since the compound of Formula 2 is more stable than the corresponding starting malonic acid on standing (or as a solution in an appropriate solvent), an additional aspect of this invention is a stable composition comprising a compound of Formula 2 in an appropriate solvent. Appropriate solvents for the composition include those listed as being appropriate for use in the method used to prepare a compound of Formula 1.

One skilled in the art will appreciate the malonic acid di-salts of the present invention can exist as the symmetrical di-salt or the asymmetrical di-salt. The present compounds are therefore not limited by the value for $M^A$ or $M^B$ being identical. As the compounds are useful as intermediates, the value for $M^A$ or $M^B$ may therefore be the same or different. One aspect of the invention is where $M^A$ and $M^B$ are equivalent (i.e. both cations are identical) and another aspect of the invention is where $M^A$ and $M^B$ are different (i.e. both cations are not identical). For example in a compound of Formula 1, both $M^A$ and $M^B$ can be Na. Alternatively $M^A$ can be Na and $M^B$ can be Li, or any other combination of values for $M^A$ and $M^B$.

The compounds of Formula 4 are mesoionic inner salts. "Inner salts", also known in the art as "zwitterions", are electrically neutral molecules but carry formal positive and negative charges on different atoms in each valence bond structure according to valence bond theory. Furthermore the molecular structure of the compounds of Formula 4 can be represented by the six valence bond structures shown below, each placing the formal positive and negative charges on different atoms. Because of this resonance, the compounds of Formula 4 are also described as "mesoionic". Although for sake of simplicity, the molecular structure of Formula 4 is depicted as a single valence bond structure herein, this particular valence bond structure is to be understood as representative of all six valence bond structures relevant to bonding in molecules of compounds of Formula 4. Therefore reference to Formula 4 herein relates to all six applicable valence bond structures and other (e.g., molecular orbital theory) structures unless otherwise specified.

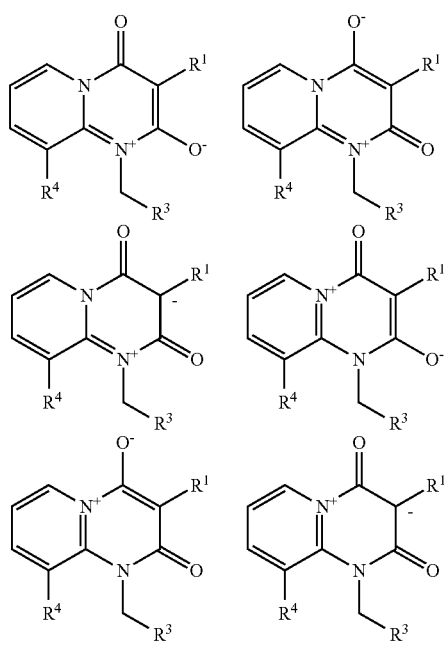

Compounds of this invention can exist as one or more conformational isomers due to restricted bond rotation caused by steric hinderance. For example, a compound of Formula 4 wherein substitution on $R^1$ (i.e. $R^2$ or Q) is a sterically demanding alkyl group (e.g., isopropyl or phenyl) in the ortho-position of the phenyl ring with respect to the pyrimidinium ring may exist as two rotamers due to restricted rotation about the phenyl ring-pyrimidinium ring bond. This invention comprises mixtures of conformational isomers. In addition, this invention includes compounds that are enriched in one conformer relative to others.

Compounds selected from Formula 4 typically exist in more than one form, and Formula 4 thus includes all crystalline and non-crystalline forms of the compounds that Formula 4 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 4 can exhibit beneficial effects (e.g., suitability for preparation of useful formulations, improved biological performance) relative to another polymorph or a mixture of polymorphs of the same compound represented by Formula 4. Preparation and isolation of a particular polymorph of a compound represented by Formula 4 can be achieved by methods known to those skilled in the art including, for example, crystallization using selected solvents and temperatures.

One skilled in the art recognizes that because in the environment and under physiological conditions salts of a compound of Formula 4 are in equilibrium with their corresponding nonsalt forms, salts share the biological utility of the nonsalt forms. Thus a wide variety of salts of the compounds of Formula 4 are useful for control of invertebrate pests and animal parasites (i.e. are suitable for animal health use). The salts of the compounds of Formula 4 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

In the following Schemes 1 though 9 the definitions of $M^A$, $M^B$, $R_1$, $R^3$ and $R^4$ in the compounds of Formulae 1, 1b, 2, 2a, 4, 5, 6, 6a, 7, 8, 9, 10, 11 and 11a are as defined above in the Summary of the Invention and description of Embodiments unless otherwise indicated. Formula 1b is a subset of Formula 1 and Formula 2a is a subset of Formula 2, Formula 6a is a subset of Formula 6a and Formula 11a is a subset of Formula 11.

In the method illustrated in Scheme 1, compounds of Formula 2 when "$M^{A+}$" or "$M^{B+}$" is a metal cation usually exist as a reaction intermediate during base hydrolysis (i.e. saponification) of compounds of Formula 6 (aryl malonates) are always acidified in situ, converted into and are used as the corresponding malonic acid in the laboratory (See, for example: *J. Org. Chem.* 1997, 62, 5116-5127).

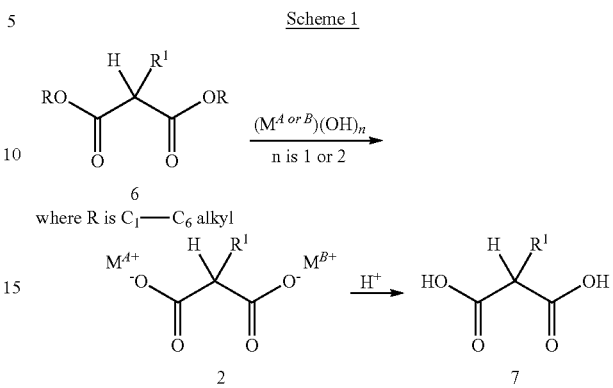

Scheme 1

The saponification reaction can take place with various bases, such as LiOH, NaOH, KOH, Ba(OH)$_2$, Ca(OH)$_2$, NH$_4$OH. Preferred for reasons of low cost are NaOH, KOH and Ca(OH)$_2$. When the cation is the +1 oxidation state, at least two equivalents of base are needed to convert both ester groups into carboxylate groups. When the cation is the +2 oxidation state, at least one equivalent of base is needed to convert both ester groups into carboxylate groups. An excess of base is not deleterious to the reaction, and it may even be desirable to run the reaction with a small amount excess of base, ranging from 0.02 to 0.2 equivalents of base to the malonate to ensure complete conversion of the more expensive malonate of Formula 6.

The saponification can be performed at a temperature ranging from a low of about 0° C. or room temperature (about 25° C.) to a higher temperature of about 100° C. When the saponification is run at higher temperature, such as about 40° C. or above, side reactions such as decarboxylations can take place. It is most preferred to run the reaction at lower temperature, such as at room temperature.

Because the saponification reaction is exothermic, it is desirable to control the rate of reaction, particularly when performing on a large scale. The rate of reaction can be controlled by either slow addition of a compound of Formula 6 into the base solution, or by slow addition of the base into the mixture of compound of Formula 6 in water.

Preparation of a compound of Formula 2 can be performed in a co-solvent, such as an alcohol, an aromatic compound or an alkyl ether to facilitate the reaction. When a co-solvent is used a phase transfer catalyst, such as a tetrabutylammonium halide can also be employed to facilitate the hydrolysis. To eliminate the possibility of forming the partially decarboxylated side product (i.e. arylacetate), saponification of the malonate is best performed in water without a co-solvent or phase transfer catalyst. The arylacetate side product can not be easily removed during the isolation of a compound of Formula 2. Furthermore, this side product is not easily removed during the preparing the subsequent malonyl di-halide, or preparation of a compound of Formula 4.

Isolation of the malonate di-salt is normally accomplished by removal of the solvent upon completion of the reaction. Removal of the solvent can be achieved by direct concentration of the saponification reaction mixture under vacuum. For example, the aqueous solution of malonate di-salt can be concentrated directly to remove water. The resulting residue can be further triturated with an organic solvent, such as methanol, to isolate the di-salt compound (*Chem. Commun.*

2000, 1519-1520). This method frequently requires the reaction mixture to be heated to temperatures higher than ambient to temperature to promote the distillation of water. Since aqueous solutions of a compound of Formula 2 exhibit a higher rate of decomposition than the solid malonyl di-salts, an alternative procedure may be used. Excess water may be removed from the reaction mixture by slowly adding the reaction mixture into a heated organic solvent capable of rapidly distilling out water azeotropically. By running the distillation in this fashion, the aqueous solution will have minimal time to be exposed to high temperature. Another method of removing excess water involves running the distillation at low temperature and under vacuum. The distillation can be run by slowly adding the reaction mixture into the desired organic solvent, or by distilling a mixture of the aqueous solution of a compound of Formula 2 and the desired organic solvent. Distillation under vacuum makes the process rather efficient while the lower temperature (such as those below 50° C. or even ambient temperature) will prevent decomposition of the compound of Formula 2.

Solvents appropriate to facilitate the removal by distillation of water for the present isolation method include aprotic solvents capable of forming a low-boiling azeotrope with water. The aprotic solvent is ordinarily a single solvent; it can also be a mixture of solvents such as xylene isomers. Low-boiling azeotropes usually have a boiling point less than both the boiling point of water and the boiling point of the solvent. By definition, low-boiling azeotropes containing water have normal boiling points of less than 100° C. (i.e. the normal boiling point of water). Thus the boiling point of the low-boiling azeotrope is substantially less than the boiling points of the compound of Formula 2, such that it will remain in the reaction mixture during distillation. As already mentioned, preferably the polar aprotic solvent and the aprotic solvent capable of forming a low-boiling azeotrope are selected so that the polar aprotic solvent has a boiling point higher than the azeotrope. The polar solvent is therefore not removed during the distillation. Solvents forming azeotropes with water are well known in the art, and compendia published listing their boiling points (see, for example, *Azeotropic Data*, Number 6 in the Advances in Chemistry Series, American Chemical Society, Washington, D.C., 1952, particularly pages 6-12). Examples of suitable aprotic solvents forming low-boiling azeotropes with water include esters such as ethyl acetate, butyl acetate and methyl butyrate; aromatic hydrocarbons such as benzene, toluene and xylenes; ethers such as tert-butyl methyl ether, tetrahydrofuran and 1,4-dioxane; alcohols such as isopropanol and n-propyl alcohol; and others such as acetonitrile and cyclohexane are suitable for the present method. Preferably, the azeotrope formed by the aprotic solvent and water contains a higher percentage of water than is soluble in the aprotic solvent at room temperature (e.g., 15-35° C.), thus facilitating large-scale separation of water from the condensed azeotrope in a decanter trap, and recycling the water-depleted aprotic solvent to the middle of the distillation column. Water-immiscible aprotic solvents such as ethyl acetate, benzene, toluene and tert-butyl methyl ether are preferred. The distillation can be run either at ambient atmosphere or at reduced pressure, such as 100 mm Hg, which can easily be achieved in a manufacturing process. Distillation at reduced pressure speeds the distillation rate and lowers the boiling temperature and pot temperature. Lower pot temperature is beneficial because decarboxylation side reactions compounds of Formula 2 are less likely.

The ammonium salts of malonic acids can be prepared by mixing the appropriate malonic acid and ammonia at ambient temperature (*J. Am. Chem. Soc.* 1914, 36, 742-747) as shown in Scheme 2. Similarly, the salts prepared with other ammonium salts can be likewise prepared using other organic amines such as triethylamine, tributylamine, diphenylamine or dicyclohexylamine.

Scheme 2

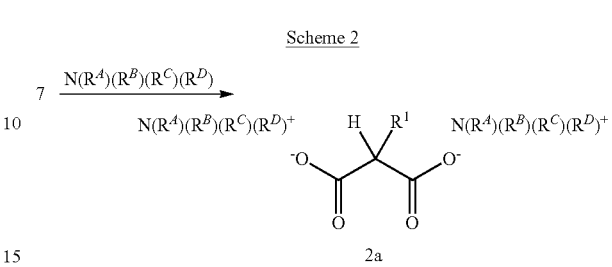

Compounds of Formula 6 can be prepared by arylation of malonate esters (using compounds of formula $R^1X^1$ wherein $X^1$ is Cl, Br or I) catalyzed by palladium (*J. Org. Chem.* 2002, 67, 541-555; see route (a) in Scheme 3) or copper (*Org. Lett.* 2002, 4, 269-272 and *Org. Lett.* 2005, 7, 4693-4695). Alternatively, compounds of Formula 6 can be prepared by the method shown in Scheme 3 (see, for example, *J. Med. Chem.* 1982, 25(6), 745-747; see route (b) in Scheme 3).

Scheme 3 where R is $C_1$—$C_6$ alkyl

Compounds of Formula 6 (wherein R is $C_1$-$C_6$ alkyl) can also be prepared from the corresponding acids by methods well known in the art. Many of the acids are commercially available or readily prepared by methods known in the art.

Compounds of Formula 6 can also be prepared by the method shown in Scheme 4. Reaction of nitriles of Formula 9 with dialkyl carbonates yields nitrile esters of Formula 10, and subsequent acidic hydrolysis in the presence of an alcohol provides the compounds of Formula 6 (see, for example, *Helvetica Chimica Acta* 1991, 74(2), 309-314). Many of the nitriles of Formula 9 are commercially available or readily prepared by methods known in the art.

Scheme 4

Alternatively, a compound of Formula 6 can be prepared by hydrolysis of the corresponding imidate ester salt of Formula 11 or imidate ester of Formula 11a as shown in Scheme 5. In this method, a compound of Formula 9 is contacted with a strong acid such as hydrogen chloride dissolved in an alcoholic solvent such as methanol or ethanol (also known as the Pinner reaction) to provide imidate ester salts of Formula 11 or imidate esters of Formula 11a. Compounds of Formula 11 or 11a can be hydrolyzed in aqous conditions, then reacted with a dialkyl carbonate under basic conditions to provide a compound of Formula 6.

Scheme 5

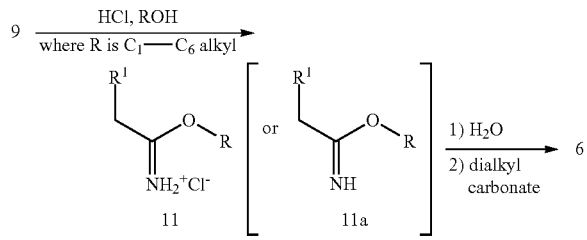

Imidate ester salts of Formula 11 or imidate esters of Formula 11a are particularly useful in the preparation of a compound of Formula 6. Therefore, one aspect of this invention is a compound of Formulae 11 or 11a wherein $R^1$ is 3,5-dichlorophenyl, 3-trifluoromethylphenyl, 3-trifluoromethoxyphenyl or 3-trifluoromethyl-5-chlorophenyl and R is methyl or ethyl which are particularly useful in the preparation of a compound of Formula 6. In particular a compound of Formula 11 wherein $R^1$ is 3,5-dichlorophenyl and R is methyl (11b) or ethyl (11c) is particularly useful in preparing a compound of Formula 6, which is useful in preparing a compound of Formula 2, (a compound of the instant invention) which is, in turn, useful in the method for preparing a compound of Formula 4 (a method of the instant invention).

There are many reports on converting malonic acids into the corresponding malonyl di-halides using different halogenation reagents such as $SOCl_2$, $(COCl)_2$, $POCl_3$, triphosgene, $PCl_5$ and $PPh_3Br_2$ in the presence or absence of a catalyst such as N,N-dimethylformamide (see *Tetrahedron*, 2011, 2548-2554) and converting the carboxylic acid into the corresponding acid halides (*Science of Synthesis, 20a-Product Class 1: acid halides*, 2006, 15-52) as shown in Scheme 6. The compound of Formula 1b also be formed in the halogenation reaction as a by-product during the formation of a compound of Formula 1.

Scheme 6

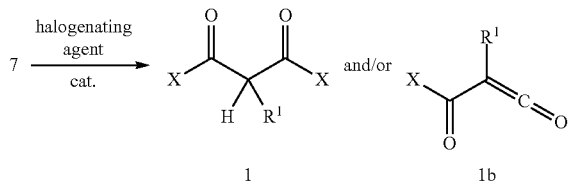

Surprisingly, conversion of malonic acid di-salts of Formula 2 can be directly converted to malonyl di-halides of Formula 1 according to the present invention as shown below in Scheme 7. Note that the compound of Formula 1b can also be formed in the halogenation reaction of the present invention. The reaction is performed in the same fashion as converting malonic acids into the corresponding acid di-halide, but does not require isolation of the malonic acid. The conversion can be conducted with various halogenation reagents such as $SOCl_2$, $(COCl)_2$, $POCl_3$, triphosgene, $PCl_5$ and $PPh_3Br_2$. Thionyl chloride, (i.e. $SOCl_2$) can be used, however, oxalyl chloride (i.e. $(COCl)_2$) can be used with lower reaction temperatures (about 0° C. to about 30° C.) to affect the conversion. In order to convert one mole of malonic acid di-salt to the corresponding dihalide, the minimum required amount of halogenation reagent is two equivalents so as to convert both carboxylate di-salt groups into acid halide groups. The reaction is usually run with an excess of halogenation reagent, from about 2.02 to about 3.0 equivalents of halogenating agent relative to the malonic acid di-salt in order to ensure complete conversion of the compound of Formula 2.

The reaction can be run in the presence of a catalyst such as pyridine, N,N-dimethylformamide or 1-formylpiperidine, with a molar ratio of the catalyst to the compound of Formula 2 ranging from about 0.001 to about 0.4 or from about 0.005 to about 0.05. The reaction can be run in aprotic solvents such as toluene, dichloromethane, cyclohexane, benzene, 1,2-dichloroethane, ethyl acetate or butyl acetate, or a combination of these solvents. The reaction takes place at different temperatures depending on the chlorinating agent. When $(COCl)_2$ is used, the temperature ranges from about 0° C. to room temperature or from about 18° C. to about 30° C. When $SOCl_2$ is employed as the halogenating agent, a temperature of about 45° C. to about 80° C. can be used.

Combining a compound of Formula 2 with the halogenating agent can be accomplished in variety of ways. One method is to add a compound of Formula 2 as a solid (or as slurry in an appropriate solvent) into a solution of halogenation reagent in an aprotic solvent such as toluene, dichloromethane, cyclohexane, benzene, 1,2-dichloroethane, ethyl acetate or butyl acetate, or a combination of these solvents. The same or different solvents can be used to form the solution of halogenation reagent and slurry with a compound of Formula 2. This method keeps the compound of Formula 2 continuously exposed to the halogenating reagent in large excess and is therefore halogenated as soon as the solid or slurry is added.

Scheme 7

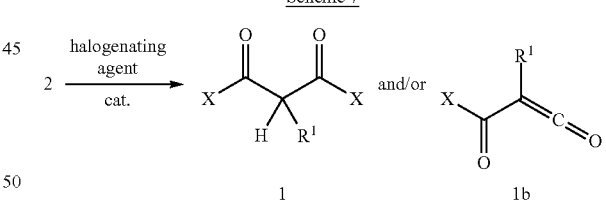

Although the conversion of malonic acid di-salts to malonyl di-halides use similar reaction conditions as the conversion of malonic acids to malonyl di-halides, the malonate di-salt is converted directly to the corresponding malonyl di-halide without formation of the malonic acid. Metal carboxylates are known to convert into the corresponding acid halide directly (*Science of Synthesis, 20a-Product Class 1: acid halides*, 2006, 15-52, mechanism discussion on page 29). The advantage of using malonic acid di-salts of the present invention is that only the corresponding metal or ammonium halides are generated as reaction byproducts. This eliminates acidic reaction conditions which can be encountered during traditional conversion of carboxylic acid into the corresponding acid halide since hydrogen halides are generated as reaction byproducts as shown in Scheme 8.

Scheme 8

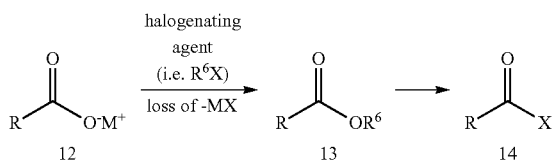

The strong reactivity of acid halides or malonyl di-halides towards relatively weak nucleophiles such as water requires that moisture be rigorously excluded when preparing, manipulating, or storing acid halides or malonyl di-halides. The reaction should be conducted under dry nitrogen in dried solvents to obtain good yields. For the same reason, crude malonyl halide solution of Formula 1 should be used promptly with no purification in order to minimize the possibility of introducing moisture during manipulation or storage.

A compound of Formula 4 can be prepared by reacting a compound of Formula 1 with a compound of Formula 5. Specifically, a compound of Formula 4 can be prepared by condensing a compound of Formula 1 with a compound of Formula 5, or by condensation of a compound of Formula 1 (or a mixture of a compound of Formulae 1 and 1b) with a compound of Formula 5 as shown in Scheme 9. A compound of Formula 1 (or a mixture of a compound of Formula 1 and 1b) are often generated in situ during the preparation of compounds of Formula 4. The compound of Formula 1 (or a mixture of a compound of Formula 1 and 1b) can be made according to Scheme 6 above and can exist in-situ in various concentrations. For example, in the above recitations, where a mixture of a compound of Formula 1 and 1b is mentioned a particularly useful mixture for preparing a compound of Formula 4 is a composition comprising a compound of Formula 1 to 1b in a ratio of 0.01:99.09 to 99.09:0.01, 49:1 to 99:1, 80:1 to 99:1 or 89:1 to 1:99.

Scheme 9

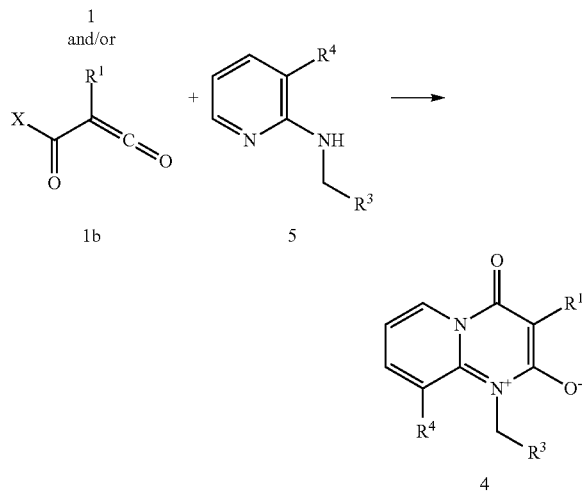

The stoichiometry of this reaction involves equimolar amounts of the compounds of Formula 1 (and/or a mixture of a compound of Formula 1 and 1b) with a compound of Formula 5. However, small molar excesses of one of the reactants are not deleterious to the reaction, and if one of the reactants is much less expensive or more preparatively accessible, using it in a slight excess (e.g., 1.05 molar equivalents) may be desirable to ensure complete conversion of the more expensive or less preparatively accessible reactant.

A compound of Formula 1b is often formed as a by-product when preparing a compound of Formula 1 and thus is also useful in preparing a compound of Formula 4. In one instance, a compound of Formula 1b wherein $R^1$ is 3-trifluoromethylphenyl and X is Cl can be used to prepare the corresponding compound of Formula 4. In another instance, a compound of Formula 1b wherein $R^1$ is 3,5-dichlorophenyl and X is Cl can be used to prepare the corresponding compound of Formula 4. A compound of Formula 1b wherein $R^1$ is 3-trifluoromethylphenyl and X is Cl can optionally be isolated, ($^1$H NMR (CDCl$_3$) δ ppm 7.91 (s, 1H), 7.80 (m, 2H), 7.65 (dd, J=7.9 Hz, 7.9 Hz, 1H), $^{19}$F NMR (CDCl$_3$) δ ppm −62.81 (s)) but is normally reacted immediately with a compound of Formula 5 (i.e in situ) as shown above in Scheme 9.

These reactions are more typically performed in the presence of an acid acceptor (see, for example, *Zeitschrift für Naturforschung, Teil B: Anorganische Chemie, Organische Chemie* 1982, 37B(2), 222-233). Typical acid acceptors include, but are not limited to, organic amines, such as trimethylamine, triethylamine, tributylamine, N,N-diisopropylethylamine, pyridine and substituted pyridines, metal oxides, such as calcium oxide, metal hydroxides such as sodium hydroxide and potassium hydroxide, metal carbonates, such as potassium carbonate and sodium carbonate, and metal bicarbonates, such as sodium bicarbonate or potassium bicarbonate.

The acid acceptor is added to the reaction mixture such that the molar ratio of acid acceptor to the compound of Formula 1 is typically in the range of about 1 to about 5. Typically a ratio in the range of about 2.0 to about 3.0 provides a rapid rate of reaction and high product yields.

These reactions are typically performed in an aprotic solvent such as toluene, dichloromethane, cyclohexane, benzene, 1,2-dichloroethane, ethyl acetate or butyl acetate, or a combination of these solvents. The solvent used for this cyclization step can be the same solvent used for the malonyl chloride or a different solvent.

The compounds of Formula 1 (or its solution in an aprotic solvent) and 5, acid acceptor, and the aprotic solvent can be combined in any convenient order to form the reaction mixture. It is discovered that two mixing modes are particularly beneficial; the first being adding the acid acceptor slowly into the mixture of compounds of Formulae 1 and 5 to scavenge the hydrogen halide byproduct. The second mode of addition is to first prepare a mixture of a compound of Formula 5 and the acid acceptor, then slowly add a solution of a compound of Formula 1 to the resulting mixture. These two addition modes provide better control of the reaction rate and higher overall yield for the cyclization. Because both the cyclization reaction and the accompanying acid scavenging operation are exothermic, this step is performed at low temperature, ranging from about −10 to about 40° C. Cooling is necessary to remove excess heat generated, particularly at the beginning of each mixing operation when the most heat is generated during a short period of time.

Without further elaboration, it is believed that one skilled in the art using the preceding description can utilize the present invention to its fullest extent. The following Examples are, therefore, to be construed as merely illustrative, and not limiting of the disclosure in any way whatsoever. The starting material for the following Examples may not have necessarily been prepared by a particular preparative run whose procedure is described in other Examples. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane at 300 MHz unless otherwise indicated; "s" means singlet, "d" means doublet, "t" means triplet, "m" means multiplet, "dd" means doublet of doublets, "br s" means broad singlet, and "dec." means decomposition.

EXAMPLE 1

Preparation of 1-[(2-chloro-5-thiazolyl)methyl]-3-(3, 5-dichlorophenyl)-2-hydroxy-9-methyl-4-oxo-4H-pyrido[1,2-a]pyridinium inner salt Step A: Preparation of 1,3-dimethyl 2-(3,5-dichlorophenyl)propanedioate To a 3-neck 1 L reactor equipped with temperature probe, overhead stirrer, reflux condenser, and nitrogen bubbler, was added copper (1) iodide (4.0 g, 0.021 mol), 2-picolinic acid (5.2 g, 0.042 mol), 3,5-dichloroiodobenzene (99 g, 0.36 mol), and cesium carbonate (233 g, 0.72 mol) under nitrogen. Dioxane (600 mL) and dimethyl malonate (91 g, 0.69 mol, 1.9 eq.) were then added to the solid mixture with stirring under nitrogen. The resulting mixture was then heated to 90° C. for 7 h, forming a pale yellow-green slurry. Water (300 mL) and hexanes (200 mL) were added to the cooled reaction mixture at room temperature, stirred for 5 min, and transferred to a separatory funnel, and extracted twice with 75 mL dioxane-hexanes (2:1). The combined organic phases were washed with saturated aqueous ammonium chloride (200 mL) and concentrated to dryness to remove all dioxane. The residue was mixed with MeOH (100 mL) and water (200 mL). After stirring for 30 min, the mixture was cooled to 0° C. with an external ice-water bath and slowly stirred for 2 h. Filtration gave 98.6 g of crude material which was dissolved in MeOH (160 mL) at 50° C., with stirring, cooled to 0° C. over 6 h then maintained at 0° C. for 2 h. Filtration gave 85.6 g of the title compound as a fine white crystalline solid. The filtrate was concentrated to remove all MeOH, and the residue was filtered to give an additional 4.12 g of the title compound for a combined 89% yield.

A second preparation of 1,3-dimethyl 2-(3,5-dichlorophenyl)propanedioate

Step A1a: Preparation of methyl 3,5-dichlorobenzeneethanimidate hydrochloride (1:1)

Hydrogen chloride was passed through a mixture of toluene (485 mL), methanol (16.8 g, 0.112 mol) and 3,5-dichlorophenylacetonitrile (100 g, 0.107 mol) at 25° C. When the hydrogen chloride uptake ceased, the mixture was sparged with nitrogen for 30 min. The mixture was filtered and the collected solid washed with toluene (150 mL) and dried overnight in a vacuum oven (50° C. at 25 in. Hg) to yield an off-white solid (98.4 g, 72%).

$^1$H NMR (DMSO-d$_6$) δ ppm 4.06 (s, 3H), 4.10 (s, 2H), 7.44-7.53 (m, 2H), 7.61 (t, 1H).

Step A1b: Preparation of methyl 3,5-dichlorobenzeneacetate

To methyl 3,5-dichlorobenzeneethanimidate hydrochloride (1:1) (i.e. the product from Step A1a) (50 g, 0.107 mol) was added to a mixture of toluene (167 mL) and water (167 mL). After 60 min the organic phase was removed, dried (MgSO$_4$), and evaporated to give the title compound as an oil (39 g, 91%).

$^1$H NMR (DMSO-d$_6$) δ ppm 3.63 (s, 3H), 3.77 (s, 2H), 7.38 (d, 2H), 7.52 (t, 1H).

Step A1c: Preparation of 1,3-dimethyl 2-(3,5-dichlorophenyl)propanedioate

A mixture sodium methoxide in methanol (28.46 g, 25%, 0.132 mol) and toluene (150 mL) was boiled with provision of a five plate Oldershaw column to remove the methanol/toluene azeotrope. The mixture was cooled to 60° C. and toluene (a volume equal to the total volume of the distillate) was added to the mixture. Dimethyl carbonate (35.95 g, 0.399 mol) was added to the reaction mixture. Methyl 3,5-dichlorobenzeneacetate (i.e. the product from Step A1b) (22.2 g, 0.101 mol) in toluene (17 mL) was added to the mixture over 70 min. When the addition was complete the mixture was stirred for a further 60 min at 60° C. The mixture was boiled and the dimethyl carbonate/methanol azeotrope was removed using the Oldershaw column. The mixture was cooled to 25° C. and acetic acid (9.5 g, 0.158 mol) was added dropwise. Water (100 mL) was added to the mixture and the organic phase separated and removed under reduced pressure. Crystallisation of the resulting residue from methanol (36 mL) gave the product as a white solid (23.9 g, 85%) melting at 72-73° C.

$^1$H NMR (CDCl$_3$) δ ppm 3.78 (s, 6H), 4.57 (s, 1H), 7.30-7.37 (m, 3H).

A third preparation of 1,3-dimethyl 2-(3,5-dichlorophenyl)propanedioate

Step A2a: Preparation of methyl 3,5-dichloro-α-cyano-benzeneacetic acid

A mixture of sodium methoxide (25% in methanol, 225.9 g, 1.045 mol) and toluene (996 mL) was boiled to remove the methanol/toluene azeotrope. Toluene was added as necessary in portions during the course of the distillation. When the head temperature reached 110° C. the distillation was continued for 20 min. The mixture was allowed to cool to room temperature and toluene was added so that the volume was the same as it was prior to distillation. Methanol (74 mL) and dimethylcarbonate (118.4 g, 1.31 mol) were added to the reaction mixture. The mixture was warmed to 50° C. and 3,5-dichlorophenylacetonitrile (148.2 g, 0.796 mol) in toluene (140 mL) was added over 3.5 h. The resulting mixture was allowed to cool to room temperature overnight, then warmed to 50° C. for a further 2 h. The mixture was allowed to cool to room temperature and acetic acid (80 g, 1.33 mol) was added drop-wise. Water (350 mL) was added to the reaction mixture and the organic phase separated and the solvent removed under reduced pressure. Crystallisation of the resulting residue from methanol (171 mL) gave the product as a white solid (148 g, 76%) melting at 97-99° C.

$^1$H NMR (CDCl$_3$) δ ppm 3.85 (s, 3H), 4.69 (s, 1H), 7.37-7.38 (m, 2H), 7.42-7.43 (m, 1H).

Step A2b: Preparation of 1,3-dimethyl 2-(3,5-dichlorophenyl)propanedioate

Methyl 3,5-dichloro-α-cyano-benzeneacetic acid (i.e. the product from Step A2a) (50 g, 0.205 mol) was added to hydrogen chloride (63.5 g, 1.73 mol) in methanol (200 mL).

The mixture was warmed to 45-50° C. After 210 min water (2 g) was added to the reaction mixture. After a further 110 min the mixture was allowed to cool to room temperature. After stirring overnight the solvent was removed under reduced pressure and the mixture was partitioned between ethyl acetate (200 mL) and water (200 mL). The organic layer was separated, dried, and evaporated. Crystallisation of the resulting residue from methanol (60 mL) gave the product as a white solid (50.68 g, 79%), the physical properties of which were identical to material prepared in Steps A and A1c above.

Step B: Preparation of potassium
2-(3,5-dichlorophenyl)propanedioate (2:1)

Potassium hydroxide (45% aqueous, 19 g, 152.7 mmol) was added to a stirred mixture of 1,3-dimethyl 2-(3,5-dichlorophenyl)propanedioate (i.e. the product of Step A, Step A1c or Step A2b) (20.0 g, 72.4 mmol) in water (40 mL) at 30° C. via a syringe pump over 2.5 h. The syringe was rinsed with water (1 mL) and the rinsate added into the reaction mixture all at once. A mild temperature rise was observed (to 30-35° C.). The resulting white slurry/suspension generally turned to a clear solution over 3 h. The mixture was then stirred at room temperature for 16 h.

A Dean-Stark trap with condenser was fitted to a 500 mL round bottom flask containing toluene (300 mL). Toluene was stirred with heating to maintain a vigorous reflux (internal temperature of 125° C.). The aqueous solution of potassium 2-(3,5-dichlorophenyl)propanedioate (2:1) (total of 59 mL, as prepared above) was added via a syringe pump into the refluxing toluene over 2 h. The temperature dropped to and stayed at 115° C. After 2.5 h, 43.9 g of water was collected and removed. After no more water was visibly collected, the mixture was maintained at the same temperature for an additional 1 h before heating was removed and stirring continued at room temperature for 16 h. Filtration of the cooled mixture gave a wet cake which was dried at 50° C. in a vacuum oven for 20 h to yield a fine white solid, a compound of the present invention (23.55 g, 98.6% after discounting 0.1 equivalents of potassium hydroxide) melting at 240-260° C. (dec.).

$^1$H NMR (CD$_3$OD) δ 7.45-7.44 (m, 2H), 7.23-7.22 (m, 1H), 4.41 (s, 1H).

Step C: Preparation of N-[(2-chloro-5-thiazolyl)methyl]-3-methyl-2-pyridinamine

To a dry 2 L three neck flask equipped with a thermo pocket and condenser was charged N-(3-methyl-2-pyridinyl)formamide (100 g), potassium carbonate (109.6 g), tetrabutylammonium bromide (4.73 g), isopropyl alcohol (7500 mL) and 2-chloro-5-(chloromethyl)thiazole (distilled, 123.9 g) under a nitrogen atmosphere. The reaction mixture was then heated to 73-75° C. and maintained at that temperature for 5.5 hours. The mixture was then cooled to 50° C., and 10% aqueous NaOH (880 g) was added via an addition funnel over a period of 20 minutes. The resulting turbid reaction mass was stirred at 57-60° C. for approximately 3.5 hours. Water (approximately 800 mL) was added over a period of 5 minutes to the reaction mixture; the reaction mixture was then cooled to 10° C. and stirred at 10° C. for 10 minutes. The slurry was filtered, and the resulting solids were washed with chilled water (2×200 mL), air-dried, and further dried under reduced pressure at 40° C. for 16 h to provide a white solid (134 g).

$^1$H NMR (dmso-d$_6$) δ 7.94 (m, 1H), 7.56 (s, 1H), 7.26 (m, 1H), 6.72 (t, 1H), 6.54 (dd, 1H), 4.61 (d, 2H), 2.04 (s, 3H).

Step D: Preparation of
2-(3,5-dichlorophenyl)propanedioyl dichloride

To an ice-water cooled mixture of oxalyl chloride (13.76 g, 108.4 mmol) in toluene (100 mL) under nitrogen was added N,N-dimethylformamide (6 drops). Potassium 2-(3,5-dichlorophenyl)propanedioate (2:1) (i.e. the product from Step B) (11.60 g, 35.67 mmol) was added in 6 batches of 1.9 g each at intervals of 15 min (Caution: off-gas observed). A temperature rise was observed but the temperature was maintained at room temperature (23-25° C.) using an external ice-water bath. The bath was removed 30 min after the complete addition of the di-potassium salt and the resulting mixture was then stirred at room temperature for an additional 2 h. Volatiles and any excess oxalyl chloride were removed under reduced pressure (20 mm Hg) for 15 min. The resulting material was used directly in the next step.

Step E: Preparation of 1-[(2-chloro-5-thiazolyl)methyl]-3-(3,5-dichlorophenyl)-2-hydroxy-9-methyl-4-oxo-4H-pyrido[1,2-a]pyridinium inner salt The 2-(3,5-dichlorophenyl)propanedioyl dichloride mixture obtained in Step D above was cooled to 0° C. in an ice-water bath, then a slurry of N-[(2-chloro-5-thiazolyl)methyl]-3-methyl-2-pyridinamine (i.e. the product from Step C) (8.68 g, 36.2 mmol) in toluene (80 mL) was added slowly over 20 min. The resulting mixture was stirred at 0° C. for 30 min, the ice-water bath was removed and stirring continued at room temperature for an additional 2 h. The reaction mixture was then cooled with an ice-water bath over 15 min, then a mixture of triethylamine (7.32 g, 72.3 mmol) in toluene (20 mL) was added dropwise over 30 min. A temperature rise was observed but the temperature was maintained at 23-30° C. After addition, the ice-water bath was removed and the mixture was stirred at room temperature for 2 h. The mixture was diluted with water (80 mL) and stirred for 30 min, filtered, and the resulting yellow cake washed with water (30 mL) and ethyl acetate (30 mL). The wet cake was dried in a vacuum oven at 50° C. for 6 h to yield the title compound as a yellow solid (14.58 g, 91.8%).

$^1$H NMR (CD$_3$COCD$_3$) δ 9.41-9.39 (m, 1H), 8.40-8.38 (m, 1H), 8.14-8.13 (m, 2H), 7.77 (s, 1H), 7.67-7.41 (m, 1H), 7.24-7.23 (m, 1H), 5.66 (s, 2H), 2.92 (s, 3H).

EXAMPLE 1A

A second preparation of 1-[(2-chloro-5-thiazolyl)methyl]-3-(3,5-dichlorophenyl)-2-hydroxy-9-methyl-4-oxo-4H-pyrido[1,2-a]pyridinium inner salt Step A: Preparation of sodium
2-(3,5-dichlorophenyl)propanedioate (2:1)

1,3-Dimethyl 2-(3,5-dichlorophenyl)propanedioate (50 g, 0.18 mol) and water (75 mL) were combined in a 500 mL reactor (jacketed) fitted with a thermometer and overhead stirrer. To the mixture was added NaOH (37% aqueous, 39.4 g, 0.36 mol, 2.02 eq.) over a period of 2.5 h at 23-25° C. via a syringe pump. After addition, water (1 mL) was used to rinse the syringe and the rinsate added to the reaction mixture. The thick, white reaction mixture turned into a clear solution after 6 h. After completion, the reaction mass was taken as such for azeo-distillation.

Toluene (250 mL) in a 500 mL jacketed reactor fitted with a Dean-Stark trap was heated to a pot temperature of 108° C. To the hot toluene, the above reaction mass was charged via a syringe pump at such a rate as to not allow the temperature not to go below 104° C. After complete distillation, about 99 g of water was collected via a Dean-Stark trap. After water collection ceased, the reaction mass was further refluxed (108° C.) for about 1 h, then cooled to room temperature (23-25° C.) and stirred for 1 h. The product was filtered and air-dried with suction for about 15 min under N, atmosphere. The product was further dried in a vacuum oven under nitrogen sweep at 50° C. for 25 h. The dried product yielded 51 g (96.5%, based on assay corrected input and actual output) of the title product as a white solid, purity by HPLC: 94.60 area % (4.32 area % of the decarboxylation by-product); moisture content (1.03%, by KF); M.P.=240-260° C. (dec.).

$^1$H NMR (CD$_3$OD) δ 7.45-7.44 (m, 2H), 7.23-7.22 (m, 1H), 4.41 (s, 1H).

Step B: Preparation of
2-(3,5-dichlorophenyl)propanedioyl dichloride

Toluene (200 mL) was added to a 1 L 4-necked round bottom flask under nitrogen atmosphere. Oxalyl chloride (25.81 g, 0.203 mol, 3 eq. was added over 5 min. The mixture was cooled to 2-5° C. and 1-formylpiperidine (0.12 g, 1.02 mmol, 0.02 eq.) was added. The above di-sodium salt obtained in Example 1A, Step A (i.e. sodium 2-(3,5-dichlorophenyl)propanedioate (2:1)) (20 g, 68 mmol) was added in 4 lots (5 g each) at the time interval of 15 minutes (slight off-gassing with mild exothermicity from 2-3° C. was observed). The reaction mixture was warmed to room temperature (23-25° C.) and maintained for 3 h. The mass was further heated to 40° C. for 1 h. After completion of the reaction, the reaction mass was distilled at 40° C. under vacuum (approximately 90-120 mm Hg) over about 30 min to remove volatile compounds and excess oxalyl chloride (during the distillation, the temperature of the reaction mass was reduced from 40° C. to 32° C., about 53 mL of the distillate was collected). After distillation, the resulting material was used directly in the next step.

$^1$H NMR (toluene-d$_8$, reaction mixture at 4 h) δ 7.10-6.70 (m, 3H), 4.49-4.45 (m, 1H).

Step C: Preparation of 1-[(2-chloro-5-thiazolyl)methyl]-3-(3,5-dichlorophenyl)-2-hydroxy-9-methyl-4-oxo-4H-pyrido[1,2-a]pyridinium inner salt The above reaction mixture was cooled to 0° C. with an ice bath, then a slurry of N-[(2-chloro-5-thiazolyl)methyl]-3-methyl-2-pyridinamine (16.36 g, 68.24 mmol, 1 eq.) in toluene (100 mL) was added to this mixture in 10 mL portions as 10 lots at an interval of 3 min. each, under nitrogen atmosphere. The conical flask was rinsed with toluene (10 mL) and added to the reaction mass of 2-(3,5-dichlorophenyl)propanedioyl dichloride with vigorous stirring. The resulting mixture was then warmed up and stirred at 20-25° C. for 2 h. Then the reaction mixture was cooled to 0° C. again, and triethylamine (13.81 g, 136.7 mmol, 2 eq.) in toluene (20 mL) was added drop wise over 1 h at 0-5° C. via a syringe pump. After the addition, the ice bath was removed and the mixture was stirred at room temperature (23-25° C.) for 6 h. Water (110 mL) was added to the reaction mass over 10 min; stirred for 30 min and filtered. The filtered solid was washed three times with water (3×50 mL), followed by a pre-cooled (5° C.) ethyl acetate (2×55 mL) wash. The wet cake was suction dried for about 30 min and further dried in a vacuum oven at 50° C. for 22 h to obtain a yellow solid (22.9 g, 74.13%).

$^1$H NMR (CD$_3$COCD$_3$) δ 9.41-9.39 (m, 1H), 8.40-8.38 (m, 1H), 8.14-8.13 (m, 2H), 7.77 (s, 1H), 7.67-7.41 (m, 1H), 7.24-7.23 (m, 1H), 5.66 (s, 2H), 2.92 (s, 3H).

EXAMPLE 2

Preparation of sodium
2-[3-(trifluoromethyl)phenyl]propanedioate (2:1)

Step A: Preparation of sodium
2-[3-(trifluoromethyl)phenyl]propanedioate (2:1)

A 100 mL round bottom flask was charged with 1,3-dimethyl 2-[3-(trifluoro-methyl)phenyl]propanedioate (5 g, 90.6% wt/wt, 16.4 mmol), and H$_2$O (10 mL). The stirred mixture was cooled to 2° C. using an external ice-water bath. Sodium hydroxide solution (50% aqueous, 3.0 g, 37.5 mmol) was added to the mixture via an additional funnel over 10 min at 2-6° C. Upon complete addition of sodium hydroxide solution, the external ice-water bath was removed and the reaction mixture was allowed to warm to room temperature and stirred at room temperature for 16 h. Activated carbon (0.5 g) was added and the reaction mixture was stirred at room temperature for 15 min then filtered.

The aqueous filtrate was charged into a 100 mL round bottom flask equipped with a Dean-Stark trap with condenser and a temperature probe. Toluene (20 mL) was added to the mixture which was then heated (bath temperature set at 115° C.) and excess water was removed azeotropically. After no additional water was visibly collected, the reaction mixture was kept at 110° C. for 1 h, then the Dean-Stark trap was removed and the mixture was cooled to room temperature. Toluene (20 mL) was added to the reaction mixture and stirred at room temperature for 30 min, then filtered. The wet solid was washed with acetonitrile (20 mL) and dried in a vacuum oven at 50° C. for 16 h to yield a white solid, a compound of the present invention (4 g, 79%) melting at >300° C.

$^1$H NMR (D$_2$O) δ 7.51-7.68 (m, 4H), 4.54 (s, 1H).

EXAMPLE 3

Preparation of 2-hydroxy-4-oxo-1-(5-pyrimidinylmethyl)-3-[3-(trifluoromethyl)phenyl]-4H-pyrido[1,2-a]pyrimidinium inner salt Step A: Preparation of
N-(5-pyrimidinylmethylene)-2-pyridinamine A solution of 2-aminopyridine (11.314 g, 120.3 mmol) and pyrimidine-5-carboxaldehyde (14.0 g, 129.6 mmol) in chloroform (300 mL) was stirred at room temperature for 15 min. The volatiles were then removed under reduced pressure (1 h at 75° C.) to yield a yellow solid. The crude solid was dissolved in chloroform (300 mL) and the solution was stirred for 15 min. The volatiles were then removed under reduced pressure (1 h at 75° C.) to yield a yellow solid. The crude solid was again dissolved in chloroform (300 mL), the solution was stirred for 15 min, and the volatiles were removed under reduced pressure (1 h at 85° C.) to yield a yellow solid. This solid was dried in a vacuum oven overnight at 80° C. to yield 22.090 g (99.8%) of the title compound.

$^1$H NMR (CDCl$_3$) δ 9.26-9.32 (m, 4H), 8.52 (d, 1H), 7.82 (t, 1H), 7.42 (d, 1H), 7.26 (t, 1H).

Step B: Preparation of N-[(5-pyrimidinyl)methyl]-2-pyridinamine

Powdered sodium borohydride (98%, 2.868 g, 75.5 mmol) was added to a solution of methanol (80 mL) and tetrahydrofuran (400 mL), and the mixture was stirred vigorously for 5 min. The product of Example 3, Step A (13.9 g, 75.5 mmol) was dissolved in tetrahydrofuran (400 mL) and the resulting solution was added dropwise to the sodium borohydride suspension at a constant rate of approximately 33 mL/min. The appearance of the reaction mixture changed from a light yellow slightly cloudy suspension to a clear red solution. Reaction progress was monitored by thin layer chromatography eluting with a 10% methanol: 40% dichloromethane: 50% toluene solvent. Upon reaction completion, acetic acid (3 mL) was added dropwise, and the reaction mixture was stirred for 5 min. Acetic acid (2 mL) and water (30 mL) were added, the reaction mixture was briefly stirred, and then ethyl acetate was added (500 mL). The reaction mixture was washed with 1 N aqueous sodium hydroxide solution (300 mL), dried over magnesium sulfate, filtered, and the solvent was removed under reduced pressure at 50° C. The resulting crude oil was dissolved in dichloromethane (50 mL) and the solution was eluted through a plug of silica gel (100 g) with ethyl acetate (3 L). The eluant was concentrated to a yellow-orange oil which slowly crystallized to provide 8.909 g (63.4%) of the title product as a pale yellow solid.

$^1$H NMR (CDCl$_3$) δ 9.12 (s, 1H), 8.76 (s, 2H), 8.10 (d, 1H), 7.42 (t, 1H), 6.64 (t, 1H), 6.42 (d, 1H), 4.99 (br s, NH), 4.61 (d, 2H).

Step C: Preparation of 1,3-dimethyl 2-[3-(trifluoromethyl)phenyl]propanedioate Dioxane (100 mL) was purged with nitrogen gas for 10 min. Phenanthrolene (1.0 g) and copper (1) iodide (1.0 g) were added to the dioxane, the suspension was allowed to stir under a nitrogen atmosphere for 5 min, and then cesium carbonate (18.72 g, 57.45 mmol), dimethyl malonate (5.46 g, 50.6 mmol), and 1-iodo-3-(trifluoromethyl)benzene (12.5 g, 46.0 mmol) were added. The reaction mixture was heated to reflux for 18 h and then cooled to room temperature. Aqueous 1 N HCl was added to the reaction mixture, the layers were separated, and the aqueous layer was extracted with ethyl acetate (3×100 mL). The combined organic layers were dried over magnesium sulfate and filtered. Celite® diatomaceous filter aid (5 g) was added to the filtrate, and the resulting suspension was concentrated under reduced pressure at 50° C. to yield a solid consisting of the crude product adsorbed onto Celite®. This solid was purified by silica gel chromatography eluting with a gradient of 100% hexanes to 25% ethyl acetate in hexanes to yield 7.36 g (58.0%) of the title product.

$^1$H NMR (CDCl$_3$) δ 7.59-7.65 (m, 3H), 7.49 (t, 1H), 4.70 (s, 1H), 3.76 (s, 6H).

Step D: Preparation of potassium 2-[3-(trifluoromethyl)phenyl]propanedioate (2:1)

A mixture of 1,3-dimethyl 2-[3-(trifluoromethyl)phenyl]propanedioate (i.e. the product of Example 3, Step C) (50.0 g, 181 mmol) and water (100 mL) in a 500 mL round bottom flask was stirred at 0° C. Potassium hydroxide (45% aqueous, 50 g, 401 mmol) was added via a syringe pump over 20 min while maintaining the reaction temperature between 0-5° C. Upon complete addition of potassium hydroxide solution, the reaction mixture was warmed to 23° C. and stirred at room temperature over night.

A Dean-Stark trap with condenser was fitted to the 500 mL round bottom flask containing the aqueous potassium 2-[3-(trifluoromethyl)phenyl]propanedioate (2:1) solution. Toluene (200 mL) was added, then the solution was heated to reflux (~86° C.) and the water was azeotropically removed. As more water was removed, the reflux temperature increased and the pot temperature reached 110° C. at the end of the distillation. After no additional water was visibly collected, the resulting mixture was maintained at reflux temperature (110° C.) for an additional 1 h before heating was removed and the resulting mixture was stirred while cooling to room temperature. Acetonitrile (250 mL) was added, and the reaction was stirred at room temperature for 1 h. The reaction mixture was filtered and the wet cake was charged back into a separate 500 mL round bottom flask, followed by acetonitrile (250 mL). The resulting mixture was stirred at room temperature for 1 h and filtered. The wet cake was washed with acetonitrile (30 mL). The solid product was dried in a vacuum oven (50° C. at 20 in. Hg) for 20 h to yield a beige solid, a compound of the present invention (62 g, 97% based on 95% HPLC area and after discounting excess KOH). M.P.=95.8° C.

$^1$H NMR (D$_2$O) δ 7.53-7.68 (m, 4H), 4.54 (s, 1H).

Step E: Synthesis of 2-hydroxy-4-oxo-1-(5-pyrimidinylmethyl)-3-[3-(trifluoromethyl)phenyl]-4H-pyrido[1,2-a]pyrimidinium inner salt To a stirred mixture of potassium 2-[3-(trifluoromethyl)phenyl]propanedioate (2:1) (i.e. the product from Example 3, Step D) (6.0 g, 18.5 mmol) and toluene (60 mL) in a 100 mL round bottom flask at 3° C. was added oxalyl chloride (5.4 g, 42.6 mmol) portion-wise via a pipette while maintaining the internal temperature at between 3-5° C. Upon complete addition of oxayl chloride, N,N-dimethylformamide (4 drops) was added to the reaction mixture at 5° C. The resulting reaction mixture was stirred at 5° C. with external cooling provided by an ice-water bath for 30 min. The bath was removed, allowing the internal temperature to warm to 22° C. The reaction mixture was stirred at 22° C. for about 5 h. Upon complete conversion to 2-[3-(trifluoromethyl)phenyl]propanedioyl dichloride, the reaction mixture was cooled to 3° C. N-[(5-pyrimidinyl)methyl]-2-pyridinamine (i.e. the product of Example 3, Step B) (3.4 g, 18.3 mmol) was added to the reaction mixture at 3° C. Triethylamine (3.75 g, 36.7 mmol) was added portion-wise to the reaction mixture via an additional funnel over 15 min while maintaining the reaction mixture temperature between 3-6° C. using an external ice-water bath. Upon complete addition of triethylamine, the ice-water bath was removed and the reaction mixture was allowed to warm to room temperature. Heptane (50 mL) was added and the resulting mixture was stirred at room temperature for 30 min then filtered. The wet solid was charged back into a clean round bottom flask, followed by water (40 mL). The reaction mixture was stirred at room temperature for 1 h, filtered and the wet solid was washed with heptane (15 mL). The solid product was dried in a vacuum oven at (50° C. at 20 mm Hg) for 20 h to obtain a yellow solid product 7.75 g. The solid product was further purified by stirring in 77 mL of a 7:1 mixture of tert-butyl methyl ether/ethyl acetate then filtered to yield of the title compound (6.2 g, 50%; 94.6% pure based on HPLC area)

¹H NMR (CDCl₃) δ 5.64 (br s, 2H), 7.43-7.48 (m, 2H), 7.50-7.52 (m, 2H), 8.03-8.11 (m, 1H), 8.13-8.16 (m, 2H) 8.83 (s, 2H), 9.19 (s, 1H), 9.55-9.58 (dd, 1H).

EXAMPLE 3A

Second preparation of 2-hydroxy-4-oxo-1-(5-pyrimidinylmethyl)-3-[3-(trifluoromethyl)phenyl]-4H-pyrido[1,2-a]pyrimidinium inner salt Step A: Preparation of sodium 2-[3-(trifluoromethyl)phenyl]propanedioate (2:1)

A mixture of 1,3-dimethyl 2-[3-(trifluoromethyl)phenyl] propanedioate (i.e. the product of Example 3, Step C) (5.0 g, 90.6 wt %, 16 mmol) and water (10 mL) in a 100-mL round bottom flask was stirred at 2° C. Sodium hydroxide (50% aqueous, 3.0 g, 38 mmol) was added via addition funnel over 10 min while maintaining the reaction temperature between 2-6° C. Upon complete addition of the sodium hydroxide solution, the reaction mixture was warmed to 23° C. and stirred at room temperature overnight.

Activated carbon (0.5 g) was added to the reaction mixture, and the mixture was stirred at room temperature for 15 min and then filtered. The aqueous filtrate was charged into a 100-mL roundbottom flask fitted with a Dean-Stark trap, a condenser, and a temperature probe. Toluene (20 mL) was added, then the solution was heated to reflux and the water was azeotropically removed. After no additional water was visibly collected, the resulting mixture was maintained at reflux temperature (110° C.) for an additional 1 h before heating was removed and the resulting mixture was stirred while cooling to room temperature. Toluene (20 mL) was added, and the mixture was stirred at room temperature for 30 min. The slurry was then filtered and the solids were washed with acetonitrile (20 mL). The solids were then dried in a vacuum oven at 50° C. for 16 h to afford the title compound as a white solid (4.0 g, 94.9 HPLC area %, 79% yield based on area %).

¹H NMR (D₂O) δ7.51-7.68 (m, 4H), 4.54 (s, 1H).

Step B: Synthesis of 2-hydroxy-4-oxo-1-(5-pyrimidinylmethyl)-3-[3-(trifluoromethyl)phenyl]-4H-pyrido[1,2-a]pyrimidinium inner salt To a stirred mixture of sodium 2-[3-(trifluoromethyl)phenyl]propanedioate (2:1) (i.e. the product from Example 3A, Step A) (5.0 g, 95.0 area %, 16 mmol) and dichloromethane (50 mL) in a 250-mL round bottom flask at −1° C. was added 1-formylpiperidine (0.09 g, 0.8 mmol). Oxalyl chloride (5.6 g, 98%, 43 mmol) was then added via addition funnel over 5 min while maintaining the internal temperature at between −3 and +1° C. The resulting reaction mixture was stirred at between −3 and +2° C. for 10 min, then at 20–22° C. for 2-3 h. Upon complete conversion to 2-[3-(trifluoromethyl)phenyl]propanedioyl dichloride, the reaction mixture was cooled to 0° C., then a mixture of N-[(5-pyrimidinyl)methyl]-2-pyridinamine (i.e. the product of Example 3, Step B) (3.2 g, 95.3%, 16.4 mmol) and 4-picoline (3.1 g, 98%, 32.6 mmol) in dichloromethane (20 mL) was added to the acid chloride mixture via syringe pump over 10 min at 0 to 3° C. Upon complete addition, the reaction mixture was warmed to 10° C. over 10 min and stirred at 9 to 12° C. for 30 min until complete conversion of the acid chloride intermediate was observed (by quenching with methanol and determining by HPLC the absence of 1,3-dimethyl 2-[(trifluoromethyl)phenyl]propanedioate). The reaction mixture was warmed to 18° C., then water (15 mL) was added to the reaction mixture at 18 to 20° C., and the two-phase mixture was stirred at 18 to 20° C. for 15 min. The mixture settled and the layers were separated. The aqueous layer was extracted with dichloromethane (2×25 mL). The organic layers were combined, and then i-propanol (30 mL) was added to the combined organic solution followed by water (1.25 mL). The resulting mixture was distilled with a pot temperature of 82° C. and with the head temperature at 42-82° C. under atmospheric pressure to remove dichloromethane and water. When the head temperature reached the boiling point of pure i-propanol, the distillation was stopped, and additional i-propanol (30 mL) was added to the hot concentrate, and the mixture was allowed to cool to room temperature and stirred at room temperature overnight during which time a solid crystallized. The mixture was then filtered and the wet solids washed with i-propanol (3×5 mL). The solid product was dried in a vacuum oven at 50-55° C. and ~250 mm Hg to afford the title compound as a yellow solid (5.0 g, 99.0 HPLC area %, 98.3 wt %, 75.9% yield from the disodium salt (i.e. sodium 2-[3-(trifluoromethyl)phenyl] propanedioate (2:1)).

By the procedures described herein together with methods known in the art, the following compounds of Tables I-1 to 1-35 can be prepared. By the procedures described herein together with methods known in the art, the methods of preparing a compound of Formula 1 can be prepared from a compound of Formula 2 as illustrated in Tables M-1 through M-155. By the procedures described herein together with methods known in the art, a compound of Formula 4 can be prepared from the compounds of Formulae 1 and 5 using the method of preparing a compound of Formula 1 from a compound of Formula 2. The following abbreviations are used in the Tables: t is tertiary, s is secondary, n is normal, i is iso, c is cyclo, Me is methyl, Et is ethyl, Pr is propyl, i-Pr is isopropyl, t-Bu is tertiary butyl, Hex is hexyl, Ph is phenyl, CN is cyano, and Bn is benzyl (—CH₂Ph). In Tables I-1 through 1-35, M-1 through M-174 and C-1 through C-42, values for Y1 through Y41 are assigned to each substituent according to the following chart:

| | |
|---|---|
| Y1 | 2-fluorophenyl |
| Y2 | 3-chlorophenyl |
| Y3 | 3-(CF₃)phenyl |
| Y4 | 3-fluorophenyl |
| Y5 | 3-cyanophenyl |
| Y6 | 4-fluorophenyl |
| Y7 | 4-chlorophenyl |
| Y8 | 4-(CF₃)phenyl |
| Y9 | 4-cyanophenyl |
| Y10 | 3-(OCF₃)phenyl |
| Y11 | 4-bromophenyl |
| Y12 | 6-chloro-3-pyridinyl |
| Y13 | 6-fluoro-3-pyridinyl |
| Y14 | 6-(CF₃)-3-pyridinyl |
| Y15 | 4,6-dichloro-3-pyridinyl |
| Y16 | 2-fluoro-6-chloro-3-pyridinyl |
| Y17 | 2,6-dichloro-3-pyridinyl |
| Y18 | 2-bromo-5-chloro-4-pyridinyl |
| Y19 | 3-bromo-5-fluorophenyl |
| Y20 | 3-chloro-5-fluorophenyl |
| Y21 | 3-fluoro-4-chlorophenyl |
| Y22 | 2,4-dichlorophenyl |
| Y23 | 2,4-difluorophenyl |
| Y24 | 2-fluoro-4-cyanophenyl |
| Y25 | 2-fluoro-4-chlorophenyl |
| Y26 | 2-methyl-4-chlorophenyl |
| Y27 | 2-fluoro-4-(CF₃)phenyl |
| Y28 | 2,4-bis(CF₃)phenyl |
| Y29 | 2-fluoro-4-bromophenyl |
| Y30 | 2-chloro-4-fluorophenyl |
| Y31 | 2-(CF₃)-4-fluorophenyl |

-continued

| | |
|---|---|
| Y32 | 2-methyl-4-(CF₃)phenyl |
| Y33 | 2-chloro-4-(CF₃)phenyl |
| Y34 | 2-(CF₃)-4-chlorophenyl |
| Y35 | 2,5-difluorophenyl |
| Y36 | 2-fluoro-5-(CF₃)phenyl |
| Y37 | 2-fluoro-5-chlorophenyl |
| Y38 | 2,5-dichlorophenyl |
| Y39 | 2-fluoro-5-(OCF₃)phenyl |
| Y40 | 2-chloro-5-(CF₃)phenyl |
| Y41 | 3-chloro-5-(CF₃)-2-pyridinyl |

TABLE I-1

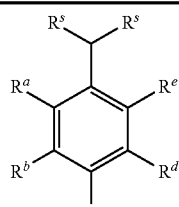

each $R^s$ is $CO_2^-Li^+$; $R^b$, $R^c$, $R^d$ and $R^e$ are H

| $R^a$ | $R^a$ | $R^a$ | $R^a$ | $R^a$ | $R^a$ | $R^a$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^a$, $R^c$, $R^d$ and $R^e$ are H

| $R^b$ | $R^b$ | $R^b$ | $R^b$ | $R^b$ | $R^b$ | $R^b$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^a$, $R^b$, $R^d$ and $R^e$ are H

| $R^c$ | $R^c$ | $R^c$ | $R^c$ | $R^c$ | $R^c$ | $R^c$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-P | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^a$ is F; $R^c$, $R^d$ and $R^e$ are H

| $R^b$ | $R^b$ | $R^b$ | $R^b$ | $R^b$ | $R^b$ | $R^b$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^a$ is F; $R^b$, $R^d$ and $R^e$ are H

| $R^c$ | $R^c$ | $R^c$ | $R^c$ | $R^c$ | $R^c$ | $R^c$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^a$ is F; $R^b$, $R^c$ and $R^e$ are H

| $R^d$ | $R^d$ | $R^d$ | $R^d$ | $R^d$ | $R^d$ | $R^d$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^a$ is F; $R^b$, $R^c$ and $R^d$ are H

| $R^e$ | $R^e$ | $R^e$ | $R^e$ | $R^e$ | $R^e$ | $R^e$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^a$ is Cl; $R^c$, $R^d$ and $R^e$ are H

| $R^b$ | $R^b$ | $R^b$ | $R^b$ | $R^b$ | $R^b$ | $R^b$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^a$ is Cl; $R^b$, $R^d$ and $R^e$ are H

| $R^c$ | $R^c$ | $R^c$ | $R^c$ | $R^c$ | $R^c$ | $R^c$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |

TABLE I-1-continued

| t-Bu | OCF₃ | Y2 | Y12 | Y22 | Y32 |
| CF₃ | OCHF₂ | Y3 | Y13 | Y23 | Y33 |

| each R$^s$ is CO₂⁻Li⁺; R$^a$ is Cl; R$^b$, R$^c$ and R$^e$ are H ||||||
|---|---|---|---|---|---|
| R$^d$ | R$^d$ | R$^d$ | R$^d$ | R$^d$ | R$^d$ |
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 |
| CF₃ | OCHF₂ | Y3 | Y13 | Y23 | Y33 |

| each R$^s$ is CO₂⁻Li⁺; R$^a$ is Cl; R$^b$, R$^c$ and R$^d$ are H ||||||
|---|---|---|---|---|---|
| R$^e$ | R$^e$ | R$^e$ | R$^e$ | R$^e$ | R$^e$ |
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 |
| CF₃ | OCHF₂ | Y3 | Y13 | Y23 | Y33 |

| each R$^s$ is CO₂⁻Li⁺; R$^a$ is OMe; R$^c$, R$^d$ and R$^e$ are H ||||||
|---|---|---|---|---|---|
| R$^b$ | R$^b$ | R$^b$ | R$^b$ | R$^b$ | R$^b$ |
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 |
| CF₃ | OCHF₂ | Y3 | Y13 | Y23 | Y33 |

| each R$^s$ is CO₂⁻Li⁺; R$^a$ is OMe; R$^b$, R$^d$ and R$^e$ are H ||||||
|---|---|---|---|---|---|
| R$^c$ | R$^c$ | R$^c$ | R$^c$ | R$^c$ | R$^c$ |
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 |
| CF₃ | OCHF₂ | Y3 | Y13 | Y23 | Y33 |

| each R$^s$ is CO₂⁻Li⁺; R$^a$ is OMe; R$^b$, R$^c$ and R$^e$ are H ||||||
|---|---|---|---|---|---|
| R$^d$ | R$^d$ | R$^d$ | R$^d$ | R$^d$ | R$^d$ |
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 |

TABLE I-1-continued

| t-Bu | OCF₃ | Y2 | Y12 | Y22 | Y32 |
| CF₃ | OCHF₂ | Y3 | Y13 | Y23 | Y33 |

| each R$^s$ is CO₂⁻Li⁺; R$^a$ is OMe; R$^b$, R$^c$ and R$^d$ are H ||||||
|---|---|---|---|---|---|
| R$^e$ | R$^e$ | R$^e$ | R$^e$ | R$^e$ | R$^e$ |
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 |
| CF₃ | OCHF₂ | Y3 | Y13 | Y23 | Y33 |

| each R$^s$ is CO₂⁻Li⁺; R$^a$ is Me; R$^c$, R$^d$ and R$^e$ are H ||||||
|---|---|---|---|---|---|
| R$^b$ | R$^b$ | R$^b$ | R$^b$ | R$^b$ | R$^b$ |
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 |
| CF₃ | OCHF₂ | Y3 | Y13 | Y23 | Y33 |

| each R$^s$ is CO₂⁻Li⁺; R$^a$ is Me; R$^b$, R$^d$ and R$^e$ are H ||||||
|---|---|---|---|---|---|
| R$^c$ | R$^c$ | R$^c$ | R$^c$ | R$^c$ | R$^c$ |
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 |
| CF₃ | OCHF₂ | Y3 | Y13 | Y23 | Y33 |

| each R$^s$ is CO₂⁻Li⁺; R$^a$ is Me; R$^b$, R$^c$ and R$^e$ are H ||||||
|---|---|---|---|---|---|
| R$^d$ | R$^d$ | R$^d$ | R$^d$ | R$^d$ | R$^d$ |
| F | CH₂F | OCH₂CF₃ | Y4 | Y14 | Y24 | Y34 |
| Cl | CHF | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 |
| CF₃ | OCHF₂ | Y3 | Y13 | Y23 | Y33 |

| each R$^s$ is CO₂⁻Li⁺; R$^a$ is Me; R$^b$, R$^c$ and R$^d$ are H ||||||
|---|---|---|---|---|---|
| R$^e$ | R$^e$ | R$^e$ | R$^e$ | R$^e$ | R$^e$ |
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |

TABLE I-1-continued

| t-Bu | OCF₃ | Y2 | Y12 | Y22 | Y32 |
| CF₃ | OCHF₂ | Y3 | Y13 | Y23 | Y33 | each $R^s$ is $CO_2^-Li^+$; $R^d$ is Cl; $R^a$, $R^c$ and $R^e$ are H

| $R^b$ | $R^b$ | $R^b$ | $R^b$ | $R^b$ | $R^b$ | $R^b$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^d$ is CF₃; $R^a$, $R^c$ and $R^e$ are H

| $R^b$ | $R^b$ | $R^b$ | $R^b$ | $R^b$ | $R^b$ | $R^b$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^b$ is Br; $R^a$, $R^c$ and $R^e$ are H

| $R^d$ | $R^d$ | $R^d$ | $R^d$ | $R^d$ | $R^d$ | $R^d$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^b$ is OCF₃; $R^a$, $R^c$ and $R^e$ are H

| $R^d$ | $R^d$ | $R^d$ | $R^d$ | $R^d$ | $R^d$ |
|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^b$ is OMe; $R^a$, $R^c$ and $R^e$ are H

| $R^d$ | $R^d$ | $R^d$ | $R^d$ | $R^d$ | $R^d$ |
|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y38 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | |

TABLE I-1-continued

| t-Bu | OCF₃ | Y2 | Y12 | Y22 | Y32 |
| CF₃ | OCHF₂ | Y3 | Y13 | Y23 | Y33 | each $R^s$ is $CO_2^-Li^+$; $R^b$ is F; $R^a$, $R^c$ and $R^e$ are H

| $R^d$ | $R^d$ | $R^d$ | $R^d$ | $R^d$ | $R^d$ | $R^d$ |
|---|---|---|---|---|---|---|
| F | CH₂F | OCH₂CF₃ | Y4 | Y14 | Y24 | Y34 |
| Cl | CHF | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^b$ is CN; $R^a$, $R^c$ and $R^e$ are H

| $R^d$ | $R^d$ | $R^d$ | $R^d$ | $R^d$ | $R^d$ | $R^d$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^b$ is Me; $R^a$, $R^c$ and $R^e$ are H

| $R^d$ | $R^d$ | $R^d$ | $R^d$ | $R^d$ | $R^d$ | $R^d$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^b$ is I; $R^a$, $R^c$ and $R^e$ are H

| $R^d$ | $R^d$ | $R^d$ | $R^d$ | $R^d$ | $R^d$ | $R^d$ |
|---|---|---|---|---|---|---|
| F | CH₂F | OCH₂CF₃ | Y4 | Y14 | Y24 | Y34 |
| Cl | CHF₂ | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |
| t-Bu | OCF₃ | Y2 | Y12 | Y22 | Y32 | |
| CF₃ | OCHF₂ | Y3 | Y13 | Y23 | Y33 | | each $R^s$ is $CO_2^-Li^+$; $R^a$ and $R^b$ are F; $R^c$ and $R^e$ are H

| $R^d$ | $R^d$ | $R^d$ | $R^d$ | $R^d$ | $R^d$ |
|---|---|---|---|---|---|
| F | CH₂F | OCH₂CF₃ | Y4 | Y14 | Y24 | Y34 |
| Cl | CHF | SCF₃ | Y5 | Y15 | Y25 | Y35 |
| Br | OMe | SCF₃ | Y6 | Y16 | Y26 | Y36 |
| I | OEt | SCHF₂ | Y7 | Y17 | Y27 | Y37 |
| Me | O—n-Pr | CO₂Me | Y8 | Y18 | Y28 | Y38 |
| Et | Ph | CO₂Et | Y9 | Y19 | Y29 | Y39 |
| Pr | O—i-Pr | CN | Y10 | Y20 | Y30 | Y40 |
| i-Pr | SF₅ | Y1 | Y11 | Y21 | Y31 | Y41 |

TABLE I-1-continued

| | | | | | |
|---|---|---|---|---|---|
| t-Bu | OCF$_3$ | Y2 | Y12 | Y22 | Y32 |
| CF$_3$ | OCHF$_2$ | Y3 | Y13 | Y23 | Y33 |

| each R$^s$ is CO$_2^-$Li$^+$; R$^a$ is F; R$^b$ is Cl; R$^c$ and R$^e$ are H | | | | | |
|---|---|---|---|---|---|
| R$^d$ | R$^d$ | R$^d$ | R$^d$ | R$^d$ | R$^d$ |
| F | CH$_2$F | OCH$_2$CF$_3$ | Y4 | Y14 | Y24 | Y34 |
| Cl | CHF$_2$ | SCF$_3$ | Y5 | Y15 | Y25 | Y35 |
| Br | OMe | SCF$_3$ | Y6 | Y16 | Y26 | Y36 |
| I | OEt | SCHF$_2$ | Y7 | Y17 | Y27 | Y37 |
| Me | O—n-Pr | CO$_2$Me | Y8 | Y18 | Y28 | Y38 |
| Et | Ph | CO$_2$Et | Y9 | Y19 | Y29 | Y39 |
| Pr | O—i-Pr | CN | Y10 | Y20 | Y30 | Y40 |
| i-Pr | SF$_5$ | Y1 | Y11 | Y21 | Y31 | Y41 |
| t-Bu | OCF$_3$ | Y2 | Y12 | Y22 | Y32 |
| CF$_3$ | OCHF$_2$ | Y3 | Y13 | Y23 | Y33 |

| R$^s$ is CO$_2^-$Li$^+$; R$^c$ is OMe; R$^a$, R$^b$ and R$^e$ are H | | | | | |
|---|---|---|---|---|---|
| R$^d$ | R$^d$ | R$^d$ | R$^d$ | R$^d$ | R$^d$ |
| F | CH$_2$F | OCH$_2$CF$_3$ | Y4 | Y14 | Y24 | Y34 |
| Cl | CHF$_2$ | SCF$_3$ | Y5 | Y15 | Y25 | Y35 |
| Br | OMe | SCF$_3$ | Y6 | Y16 | Y26 | Y36 |
| I | OEt | SCHF$_2$ | Y7 | Y17 | Y27 | Y37 |
| Me | O—n-Pr | CO$_2$Me | Y8 | Y18 | Y28 | Y38 |
| Et | Ph | CO$_2$Et | Y9 | Y19 | Y29 | Y39 |
| Pr | O—i-Pr | CN | Y10 | Y20 | Y30 | Y40 |
| i-Pr | SF$_5$ | Y1 | Y11 | Y21 | Y31 | Y41 |
| t-Bu | OCF$_3$ | Y2 | Y12 | Y22 | Y32 |
| CF$_3$ | OCHF$_2$ | Y3 | Y13 | Y23 | Y33 |

| each R$^s$ is CO$_2^-$Li$^+$; R$^c$ is Me; R$^a$, R$^b$ and R$^e$ are H | | | | | |
|---|---|---|---|---|---|
| R$^d$ | R$^d$ | R$^d$ | R$^d$ | R$^d$ | R$^d$ |
| F | CH$_2$F | OCH$_2$CF$_3$ | Y4 | Y14 | Y24 | Y34 |
| Cl | CHF$_2$ | SCF$_3$ | Y5 | Y15 | Y25 | Y35 |
| Br | OMe | SCF$_3$ | Y6 | Y16 | Y26 | Y36 |
| I | OEt | SCHF$_2$ | Y7 | Y17 | Y27 | Y37 |
| Me | O—n-Pr | CO$_2$Me | Y8 | Y18 | Y28 | Y38 |
| Et | Ph | CO$_2$Et | Y9 | Y19 | Y29 | Y39 |
| Pr | O—i-Pr | CN | Y10 | Y20 | Y30 | Y40 |
| i-Pr | SF$_5$ | Y1 | Y11 | Y21 | Y31 | Y41 |
| t-Bu | OCF$_3$ | Y2 | Y12 | Y22 | Y32 |
| CF$_3$ | OCHF$_2$ | Y3 | Y13 | Y23 | Y33 |

| each R$^s$ is CO$_2^-$Li$^+$; R$^c$ is F; R$^a$, R$^b$ and R$^e$ are H | | | | | |
|---|---|---|---|---|---|
| R$^d$ | R$^d$ | R$^d$ | R$^d$ | R$^d$ | R$^d$ |
| F | CH$_2$F | OCH$_2$CF$_3$ | Y4 | Y14 | Y24 | Y34 |
| Cl | CHF$_2$ | SCF$_3$ | Y5 | Y15 | Y25 | Y35 |
| Br | OMe | SCF$_3$ | Y6 | Y16 | Y26 | Y36 |
| I | OEt | SCHF$_2$ | Y7 | Y17 | Y27 | Y37 |
| Me | O—n-Pr | CO$_2$Me | Y8 | Y18 | Y28 | Y38 |
| Et | Ph | CO$_2$Et | Y9 | Y19 | Y29 | Y39 |
| Pr | O—i-Pr | CN | Y10 | Y20 | Y30 | Y40 |
| i-Pr | SF$_5$ | Y1 | Y11 | Y21 | Y31 | Y41 |
| t-Bu | OCF$_3$ | Y2 | Y12 | Y22 | Y32 |
| CF$_3$ | OCHF$_2$ | Y3 | Y13 | Y23 | Y33 |

| each R$^s$ is CO$_2^-$Li$^+$; R$^c$ is Cl; R$^a$, R$^b$ and R$^e$ are H | | | | | |
|---|---|---|---|---|---|
| R$^d$ | R$^d$ | R$^d$ | R$^d$ | R$^d$ | R$^d$ |
| F | CH$_2$F | OCH$_2$CF$_3$ | Y4 | Y14 | Y24 | Y34 |
| Cl | CHF$_2$ | SCF$_3$ | Y5 | Y15 | Y25 | Y35 |
| Br | OMe | SCF$_3$ | Y6 | Y16 | Y26 | Y36 |
| I | OEt | SCHF$_2$ | Y7 | Y17 | Y27 | Y37 |
| Me | O—n-Pr | CO$_2$Me | Y8 | Y18 | Y28 | Y38 |
| Et | Ph | CO$_2$Et | Y9 | Y19 | Y29 | Y39 |
| Pr | O—i-Pr | CN | Y10 | Y20 | Y30 | Y40 |
| i-Pr | SF$_5$ | Y1 | Y11 | Y21 | Y31 | Y41 |
| t-Bu | OCF$_3$ | Y2 | Y12 | Y22 | Y32 |
| CF$_3$ | OCHF$_2$ | Y3 | Y13 | Y23 | Y33 |

| each R$^s$ is CO$_2^-$Li$^+$; R$^a$ and R$^e$ are F; R$^c$ and R$^d$ are H | | | | | |
|---|---|---|---|---|---|
| R$^b$ | R$^b$ | R$^b$ | R$^b$ | R$^b$ | R$^b$ | R$^b$ |
| F | CH$_2$F | OCH$_2$CF$_3$ | Y4 | Y14 | Y24 | Y34 |
| Cl | CHF$_2$ | SCF$_3$ | Y5 | Y15 | Y25 | Y35 |
| Br | OMe | SCF$_3$ | Y6 | Y16 | Y26 | Y36 |
| I | OEt | SCHF$_2$ | Y7 | Y17 | Y27 | Y37 |
| Me | O—n-Pr | CO$_2$Me | Y8 | Y18 | Y28 | Y38 |
| Et | Ph | CO$_2$Et | Y9 | Y19 | Y29 | Y39 |
| Pr | O—i-Pr | CN | Y10 | Y20 | Y30 | Y40 |
| i-Pr | SF$_5$ | Y1 | Y11 | Y21 | Y31 | Y41 |
| t-Bu | OCF$_3$ | Y2 | Y12 | Y22 | Y32 |
| CF$_3$ | OCHF$_2$ | Y3 | Y13 | Y23 | Y33 |

Table I-2

Table I-2 is identical to Table I-1, except that the phrase "each R$^s$ is CO$_2^-$Li$^+$" in each header row is replaced with the phrase "R$^s$ is CO$_2^-$Na$^+$". The values for R$^a$, R$^b$, R$^c$, R$^d$ and R$^e$ appearing in each header row or within the table remain the same.

Table I-3

Table I-3 is identical to Table I-1, except that the phrase "each R$^s$ is CO$_2^-$Li$^+$" in each header row is replaced with the phrase "each R$^s$ is CO$_2^-$K+". The values for R$^a$, R$^b$, R$^c$, R$^d$ and R$^e$ appearing in each header row or within the table remain the same.

Table I-4

Table I-4 is identical to Table I-1, except that the phrase "each R$^s$ is CO$_2^-$Li$^+$" in each header row is replaced with the phrase "each R$^s$ is CO$_2^+$NH$_4$+". The values for R$^a$, R$^b$, R$^c$, R$^d$ and R$^e$ appearing in each header row or within the table remain the same.

Table I-5

Table I-5 is identical to Table I-1, except that the phrase "each R$^s$ is CO$_2^-$Li$^+$" in each header row is replaced with the phrase "each R$^s$ is CO$_2^-$[½ Ca]$^+$". The values for R$^a$, R$^b$, R$^c$, R$^d$ and R$^e$ appearing in each header row or within the table remain the same.

Table I-6

Table I-6 is identical to Table I-1, except that the phrase "each R$^s$ is CO$_2^-$Li$^+$" in each header row is replaced with the phrase "each R$^s$ is CO$_2^-$[½ Ba]$^+$". The values for R$^a$, R$^b$, R$^c$, R$^d$ and R$^e$ appearing in each header row or within the table remain the same.

Table I-7

Table I-7 is identical to Table I-1, except that the phrase "each R$^s$ is CO$_2^-$Li$^+$" in each header row is replaced with the phrase "each R$^s$ is CO$_2^-$[NH(Me)$_3$]$^+$". The values for R$^a$, R$^b$, R$^c$, R$^d$ and R$^e$ appearing in each header row or within the table remain the same.

Table I-8

Table I-8 is identical to Table I-1, except that the phrase "each $R^s$ is $CO_2^-Li^+$" in each header row is replaced with the phrase "each $R^s$ is $CO_2^-[NH(Et)_3]^+$". The values for $R^a$, $R^b$, $R^c$, $R^d$ and $R^e$ appearing in each header row or within the table remain the same.

Table I-9

Table I-9 is identical to Table I-1, except that the phrase "each $R^s$ is $CO_2^-Li^+$" in each header row is replaced with the phrase "each $R^s$ is $CO_2^-[NH(n-Bu)_3]^+$". The values for $R^a$, $R^b$, $R^c$, $R^d$ and $R^e$ appearing in each header row or within the table remain the same.

Table I-10

Table I-10 is identical to Table I-1, except that the phrase "each $R^s$ is $CO_2^-Li^+$" in each header row is replaced with the phrase "each $R^s$ is $CO_2^-[NH_2(Ph)_2]^+$". The values for $R^a$, $R^b$, $R^c$, $R^d$ and $R^e$ appearing in each header row or within the table remain the same.

Table I-11

Table I-11 is identical to Table I-1, except that the phrase "each $R^s$ is $CO_2^-Li^+$" in each header row is replaced with the phrase "each $R^s$ is $CO_2^-[NH_2(Bn)_2]^+$". The values for $R^a$, $R^b$, $R^c$, $R^d$ and $R^e$ appearing in each header row or within the table remain the same.

Table I-12

Table I-12 is identical to Table I-1, except that the phrase "each $R^s$ is $CO_2^-Li^+$" in each header row is replaced with the phrase "each $R^s$ is $CO_2^-[NH_2(c-Hex)_2]^+$". The values for $R^a$, $R^b$, $R^c$, $R^d$ and $R^e$ appearing in each header row or within the table remain the same.

Table I-13

Table I-13 is identical to Table I-1, except that the phrase "each $R^s$ is $CO_2^-Li^+$" in each header row is replaced with the phrase "each $R^s$ is $CO_2^-[NH_2(Me)_2]^+$". The values for $R^a$, $R^b$, $R^c$, $R^d$ and $R^e$ appearing in each header row or within the table remain the same.

Table I-14

Table I-14 is identical to Table I-1, except that the phrase "each $R^s$ is $CO_2^-Li^+$" in each header row is replaced with the phrase "each $R^s$ is $CO_2^-[NH_2(Et)_2]^+$". The values for $R^a$, $R^b$, $R^c$, $R^d$ and $R^e$ appearing in each header row or within the table remain the same.

Table I-15

Table I-15 is identical to Table I-1, except that the phrase "each $R^s$ is $CO_2^-Li^*$" in each header row is replaced with the phrase "each $R^s$ is $CO_2^-[NHEt(i-Pr)_2]^+$". The values for $R^a$, $R^b$, $R^c$, $R^d$ and $R^e$ appearing in each header row or within the table remain the same.

Table I-1A

Table I-1A is identical to Table I-1, except that the phrase "each $R^s$ is $CO_2^-Li^+$", in each header row is replaced with the phrase "one $R^s$ is $CO_2^-Li^+$, the other $R^s$ is $CO_2^-Na^+$". The values for $R^a$, $R^b$, $R^c$, $R^d$ and $R^e$ appearing in each header row or within the table remain the same.

Table I-2A

Table I-2A is identical to Table I-1, except that the phrase "each $R^s$ is $CO_2^-Li^+$" in each header row is replaced with the phrase "one $R^s$ is $CO_2^-K^+$, the other $R^s$ is $CO_2^-Na^+$". The values for $R^a$, $R^b$, $R^c$, $R^d$ and $R^e$ appearing in each header row or within the table remain the same.

Table I-3A

Table I-3A is identical to Table I-1, except that the phrase "each $R^s$ is $CO_2^-Li^+$" in each header row is replaced with the phrase "one $R^s$ is $CO_2^-NH_4^+$, the other $R^s$ is $CO_2^-Na^+$". The values $R^a$, $R^b$, $R^c$, $R^d$ and $R^e$ appearing in each header row or within the table remain the same.

Table I-4A

Table I-4A is identical to Table I-1, except that the phrase "each $R^s$ is $CO_2^-Li^+$" in each header row is replaced with the phrase "one $R^s$ is $CO_2^-[\frac{1}{2} Ca]^+$, the other $R^s$ is $CO_2^-Na^+$". The values for $R^a$, $R^b$, $R^c$, $R^d$ and $R^e$ appearing in each header row or within the table remain the same.

Table I-5A

Table I-5A is identical to Table I-1, except that the phrase "each $R^s$ is $CO_2^-Li^+$" in each header row is replaced with the phrase "one $R^s$ is $CO_2^-[\frac{1}{2} Ba]^+$, the other $R^s$ is $CO_2^-Na^+$". The values for $R^a$, $R^b$, $R^c$, $R^d$ and $R^e$ appearing in each header row or within the table remain the same.

Table I-6A

Table I-6A is identical to Table I-1, except that the phrase "each $R^s$ is $CO_2^-Li^+$" in each header row is replaced with the phrase "one $R^s$ is $CO_2^-[NH(Me)_3]^+$, the other $R^s$ is $CO_2^-Na^+$". The values for $R^a$, $R^b$, $R^c$, $R^d$ and $R^e$ appearing in each header row or within the table remain the same.

Table I-7A

Table I-7A is identical to Table I-1, except that the phrase "each $R^s$ is $CO_2^-Li^+$" in each header row is replaced with the phrase "one $R^s$ is $CO_2^-[NH(Et)_3]^+$, the other $R^s$ is $CO_2^-Na^+$". The values for $R^a$, $R^b$, $R^c$, $R^d$ and $R^e$ appearing in each header row or within the table remain the same.

Table I-8A

Table I-8A is identical to Table I-1, except that the phrase "each $R^s$ is $CO_2^-Li^+$" in each header row is replaced with the phrase "one $R^s$ is $CO_2^-[NH(n-Bu)_3]^+$, the other $R^s$ is $CO_2^-Na^+$". The values for $R^a$, $R^b$, $R^c$, $R^d$ and $R^e$ appearing in each header row or within the table remain the same.

Table I-9A

Table I-9A is identical to Table I-1, except that the phrase "each $R^s$ is $CO_2^-Li^+$" in each header row is replaced with the phrase "one $R^s$ is $CO_2^-[NH_2(Ph)_2]^+$, the other $R^s$ is $CO_2^-$ $Na^+$". The values for $R^a$, $R^b$, $R^c$, $R^d$ and $R^e$ appearing in each header row or within the table remain the same.

Table I-10A

Table I-10A is identical to Table I-1, except that the phrase "each $R^s$ is $CO_2^-Li^+$" in each header row is replaced with the phrase "one $R^s$ is $CO_2^-[NH_2(Bn)_2]^+$, the other $R^s$ is $CO_2^-Na^+$". The values for $R^a$, $R^b$, $R^c$, $R^d$ and $R^e$ appearing in each header row or within the table remain the same.

Table I-11A

Table I-11A is identical to Table I-1, except that the phrase "each $R^s$ is $CO_2^-Li^+$" in each header row is replaced with the phrase "one $R^s$ is $CO_2^-[NH_2(c-Hex)_2]^+$, the other $R^s$ is $CO_2^-Na^+$". The values for $R^a$, $R^b$, $R^c$, $R^d$ and $R^e$ appearing in each header row or within the table remain the same.

Table I-12A

Table I-12A is identical to Table I-1, except that the phrase "each $R^s$ is $CO_2^-Li^+$" in each header row is replaced with the phrase "one $R^s$ is $CO_2^-[NH_2(Me)_2]^+$, the other $R^s$ is $CO_2^-Na^+$". The values for $R^a$, $R^b$, $R^c$, $R^d$ and $R^e$ appearing in each header row or within the table remain the same.

Table I-13A

Table I-13A is identical to Table I-1, except that the phrase "each $R^s$ is $CO_2^-Li^+$" in each header row is replaced with the phrase "one $R^s$ is $CO_2^-[NH_2(Et)_2]^+$, the other $R^s$ is $CO_2^-Na^+$". The values for $R^a$, $R^b$, $R^c$, $R^d$ and $R^e$ appearing in each header row or within the table remain the same.

Table I-14A

Table I-14A is identical to Table I-1, except that the phrase "each $R^s$ is $CO_2^-Li^+$" in each header row is replaced with the phrase "one $R^s$ is $CO_2^-[NHEt(i-Pr)_2]^+$, the other $R^s$ is $CO_2^{-Na+}$". The values for $R^a$, $R^b$, $R^c$, $R^d$ and $R^e$ appearing in each header row or within the table remain the same.

Table I-1B

Table I-1B is identical to Table I-1, except that the phrase "each $R^s$ is $CO_2^-Li^+$", in each header row is replaced with the phrase "one $R^s$ is $CO_2^-Li$, the other $R^s$ is $CO_2^-K^+$". The values for $R^a$, $R^b$, $R^c$, $R^d$ and $R^e$ appearing in each header row or within the table remain the same.

Table I-2B

Table I-2B is identical to Table I-1, except that the phrase "each $R^s$ is $CO_2^-Li^+$" in each header row is replaced with the phrase "one $R^s$ is $CO_2^-Na$, the other $R^s$ is $CO_2^-K^+$". The values for $R^a$, $R^b$, $R^c$, $R^d$ and $R^e$ appearing in each header row or within the table remain the same.

Table I-3B

Table I-3B is identical to Table I-1, except that the phrase "each $R^s$ is $CO_2^-Li^+$" in each header row is replaced with the phrase "one $R^s$ is $CO_2^-NH_4+$, the other $R^s$ is $CO_2^-K^+$". The values for $R^a$, $R^b$, $R^c$, $R^d$ and $R^e$ appearing in each header row or within the table remain the same.

Table I-4B

Table I-4B is identical to Table I-1, except that the phrase "each $R^s$ is $CO_2^-Li^+$" in each header row is replaced with the phrase "one $R^s$ is $CO_2^-[½ Ca]^+$, the other $R^s$ is $CO_2^-K^+$". The values $R^a$, $R^b$, $R^c$, $R^d$ and $R^e$ appearing in each header row or within the table remain the same.

Table I-5B

Table I-5B is identical to Table I-1, except that the phrase "each $R^s$ is $CO_2^-Li^+$" in each header row is replaced with the phrase "one $R^s$ is $CO_2^-[½ Ba]^+$, the other $R^s$ is $CO_2^-K^+$". The values for $R^a$, $R^b$, $R^c$ and $R^d$ appearing in each header row or within the table remain the same.

Table I-6B

Table I-6B is identical to Table I-1, except that the phrase "each $R^s$ is $CO_2^-Li^+$" in each header row is replaced with the phrase "one $R^s$ is $CO_2^-[NH(Me)_3]^+$, the other $R^s$ is $CO_2^-K^+$". The values for $R^a$, $R^b$, $R^c$, $R^d$ and $R^e$ appearing in each header row or within the table remain the same.

Table I-7B

Table I-7B is identical to Table I-1, except that the phrase "each $R^s$ is $CO_2^-Li^+$" in each header row is replaced with the phrase "one $R^s$ is $CO_2^-[NH(Et)_3]^+$, the other $R^s$ is $CO_2^-K^+$". The values for $R^a$, $R^b$, $R^c$, $R^d$ and $R^e$ appearing in each header row or within the table remain the same.

Table I-8B

Table I-8B is identical to Table I-1, except that the phrase "each $R^s$ is $CO_2^-Li^+$" in each header row is replaced with the phrase "one $R^s$ is $CO_2^-[NH(n-Bu)_3]^+$, the other $R^s$ is $CO_2^-K^+$". The values for $R^a$, $R^b$, $R^c$, $R^d$ and $R^e$ appearing in each header row or within the table remain the same.

Table I-9B

Table I-9B is identical to Table I-1, except that the phrase "each $R^s$ is $CO_2^-Li^+$" in each header row is replaced with the phrase "one $R^s$ is $CO_2^-[NH_2(Ph)_2]^+$, the other $R^s$ is $CO_2^-K^+$". The values for $R^a$, $R^b$, $R^c$, $R^d$ and $R^e$ appearing in each header row or within the table remain the same.

Table I-10B

Table I-10B is identical to Table I-1, except that the phrase "each $R^s$ is $CO_2^-Li^+$" in each header row is replaced with the phrase "one $R^s$ is $CO_2^-[NH_2(Bn)_2]^+$, the other $R^s$ is $CO_2^-K^+$". The values for $R^a$, $R^b$, $R^c$, $R^d$ and $R^e$ appearing in each header row or within the table remain the same.

Table I-11B

Table I-11B is identical to Table I-1, except that the phrase "each $R^s$ is $CO_2^-Li^+$" in each header row is replaced with the phrase "one $R^s$ is $CO_2^-[NH_2(c-Hex)_2]^+$, the other $R^s$ is $CO_2^-K+$". The values for $R^a$, $R^b$, $R^c$, $R^d$ and $R^e$ appearing in each header row or within the table remain the same.

Table I-12B

Table I-12B is identical to Table I-1, except that the phrase "each $R^s$ is $CO_2^-Li^+$" in each header row is replaced with the

Table I-13B

Table I-13B is identical to Table I-1, except that the phrase "each $R^s$ is $CO_2^-Li^+$" in each header row is replaced with the phrase "one $R^s$ is $CO_2^-[NH_2(Et)_2]^+$, the other $R^s$ is $CO_2^-K^+$". The values for $R^a$, $R^b$, $R^c$, $R^d$ and $R^e$ appearing in each header row or within the table remain the same.

Table I-14B

Table I-14B is identical to Table I-1, except that the phrase "each $R^s$ is $CO_2^-Li^+$" in each header row is replaced with the phrase "one $R^s$ is $CO_2^-[NHEt(i-Pr)_2]^+$, the other $R^s$ is $CO_2^-K^+$". The values for $R^a$, $R^b$, $R^c$, $R^d$ and $R^e$ appearing in each header row or within the table remain the same.

Table I-1C

Table I-1C is identical to Table I-1, except that the phrase "each $R^s$ is $CO_2^-Li^+$" in each header row is replaced with the phrase "one $R^s$ is $CO_2^-Li^+$, the other $R^s$ is $CO_2^-[½ Ca]$". The values for $R^a$, $R^b$, $R^c$, $R^d$ and $R^e$ appearing in each header row or within the table remain the same.

Table I-2C

Table I-2C is identical to Table I-1, except that the phrase "each $R^s$ is $CO_2^-Li^+$" in each header row is replaced with the phrase "one $R^s$ is $CO_2^-K^+$, the other $R^s$ is $CO_2^-[½ Ca]^+$". The values for $R^a$, $R^b$, $R^c$, $R^d$ and $R^e$ appearing in each header row or within the table remain the same.

Table I-3C

Table I-3C is identical to Table I-1, except that the phrase "each $R^s$ is $CO_2^-Li^+$" in each header row is replaced with the phrase "one $R^s$ is $CO_2^-NH_4+$, the other $R^s$ is $CO_2^-[½ Ca]^+$". The values for $R^a$, $R^b$, $R^c$, $R^d$ and $R^e$ appearing in each header row or within the table remain the same.

Table I-4C

Table I-4C is identical to Table I-1, except that the phrase "each $R^s$ is $CO_2^-Li^+$" in each header row is replaced with the phrase "one $R^s$ is $CO_2^-Na^+$, the other $R^s$ is $CO_2^-[½ Ca]^+$". The values for $R^a$, $R^b$, $R^c$, $R^d$ and $R^e$ appearing in each header row or within the table remain the same.

Table I-5C

Table I-5C is identical to Table I-1, except that the phrase "each $R^s$ is $CO_2^-Li^+$" in each header row is replaced with the phrase "one $R^s$ is $CO_2^-[½ Ba]^+$, the other $R^s$ is $CO_2^-[½ Ca]^+$". The values for $R^a$, $R^b$, $R^c$, $R^d$ and $R^e$ appearing in each header row or within the table remain the same.

Table I-6C

Table I-6C is identical to Table I-1, except that the phrase "each $R^s$ is $CO_2^-Li^+$" in each header row is replaced with the phrase "one $R^s$ is $CO_2^-[NH(Me)_3]^+$, the other $R^s$ is $CO_2^-[½ Ca]^+$". The values for $R^a$, $R^b$, $R^c$, $R^d$ and $R^e$ appearing in each header row or within the table remain the same.

Table I-7C

Table I-7C is identical to Table I-1, except that the phrase "each $R^s$ is $CO_2^-Li^+$" in each header row is replaced with the phrase "one $R^s$ is $CO_2^-[NH(Et)_3]^+$, the other $R^s$ is $CO_2^-[½ Ca]^+$". The values for $R^a$, $R^b$, $R^c$, $R^d$ and $R^e$ appearing in each header row or within the table remain the same.

Table I-8C

Table I-8C is identical to Table I-1, except that the phrase "each $R^s$ is $CO_2^-Li^+$" in each header row is replaced with the phrase "one $R^s$ is $CO_2^-[NH(n-Bu)_3]^+$, the other $R^s$ is $CO_2^-[½ Ca]^+$". The values for $R^a$, $R^b$, $R^c$, $R^d$ and $R^e$ appearing in each header row or within the table remain the same.

Table I-9C

Table I-9C is identical to Table I-1, except that the phrase "each $R^s$ is $CO_2^-Li^+$" in each header row is replaced with the phrase "one $R^s$ is $CO_2^-[NH_2(Ph)_2]^+$, the other $R^s$ is $CO_2^-[½ Ca]^+$". The values for $R^a$, $R^b$, $R^c$, $R^d$ and $R^e$ appearing in each header row or within the table remain the same.

Table I-10C

Table I-10C is identical to Table I-1, except that the phrase "each $R^s$ is $CO_2^-Li^+$" in each header row is replaced with the phrase "one $R^s$ is $CO_2^-[NH_2(Bn)_2]^+$, the other $R^s$ is $CO_2^-[½ Ca]^+$". The values for $R^a$, $R^b$, $R^c$, $R^d$ and $R^e$ appearing in each header row or within the table remain the same.

Table I-11 C

Table I-11C is identical to Table I-1, except that the phrase "each $R^s$ is $CO_2^-Li^+$" in each header row is replaced with the phrase "one $R^s$ is $CO_2^-[NH_2(c-Hex)_2]^+$, the other $R^s$ is $CO_2^-[½ Ca]^+$". The values for $R^a$, $R^b$, $R^c$, $R^d$ and $R^e$ appearing in each header row or within the table remain the same.

Table I-12C

Table I-12C is identical to Table I-1, except that the phrase "each $R^s$ is $CO_2^-Li^+$" in each header row is replaced with the phrase "one $R^s$ is $CO_2^-[NH_2(Me)_2]^+$, the other $R^s$ is $CO_2^-[½ Ca]^+$". The values for $R^a$, $R^b$, $R^c$, $R^d$ and $R^e$ appearing in each header row or within the table remain the same.

Table I-13C

Table I-13C is identical to Table I-1, except that the phrase "each $R^s$ is $CO_2^-Li^+$" in each header row is replaced with the phrase "one $R^s$ is $CO_2^-[NH_2(Et)_2]^-$, the other $R^s$ is $CO_2^-[½ Ca]^+$". The values for $R^a$, $R^b$, $R^c$, $R^d$ and $R^e$ appearing in each header row or within the table remain the same.

Table I-14C

Table I-14C is identical to Table I-1, except that the phrase "each $R^s$ is $CO_2^-Li^+$" in each header row is replaced with the phrase "one $R^s$ is $CO_2^-[NHEt(i-Pr)_2]^+$, the other $R^s$ is $CO_2^-[½ Ca]^+$". The values for $R^a$, $R^b$, $R^c$, $R^d$ and $R^e$ appearing in each header row or within the table remain the same.

Table I-1D

Table I-1D is identical to Table I-1, except that the phrase "each $R^s$ is $CO_2^-Li^+$" in each header row is replaced with the phrase "one $R^s$ is $CO_2^-Li^+$, the other $R^s$ is $CO_2[NH(Et)_3]^+$". The values for $R^a$, $R^b$, $R^c$, $R^d$ and $R^e$ appearing in each header row or within the table remain the same.

Table I-2D

Table I-2D is identical to Table I-1, except that the phrase "each $R^s$ is $CO_2^-Li^+$" in each header row is replaced with the phrase "one $R^s$ is $CO_2^-K^+$, the other $R^s$ is $CO_2^-[NH(Et)_3]^+$". The values for $R^a$, $R^b$, $R^c$, $R^d$ and $R^e$ appearing in each header row or within the table remain the same.

Table I-3D

Table I-3D is identical to Table I-1, except that the phrase "each $R^s$ is $CO_2^-Li^+$" in each header row is replaced with the phrase "one $R^s$ is $CO_2^-NH_4+$, the other $R^s$ is $CO_2^-[NH(Et)_3]^+$". The values for $R^a$, $R^b$, $R^c$, $R^d$ and $R^e$ appearing in each header row or within the table remain the same.

Table I-4D

Table I-4D is identical to Table I-1, except that the phrase "each $R^s$ is $CO_2^-Li^+$" in each header row is replaced with the phrase "one $R^s$ is $CO_2^-[\frac{1}{2} Ca]^+$, the other $R^s$ is $CO_2^-[NH(Et)_3]^+$". The values for $R^a$, $R^b$, $R^c$, $R^d$ and $R^e$ appearing in each header row or within the table remain the same.

Table I-5D

Table I-5D is identical to Table I-1, except that the phrase "each $R^s$ is $CO_2^-Li^+$" in each header row is replaced with the phrase "one $R^s$ is $CO_2^-[\frac{1}{2} Ba]^+$, the other $R^s$ is $CO_2^-[NH(Et)_3]^+$". The values for $R^a$, $R^b$, $R^c$, $R^d$ and $R^e$ appearing in each header row or within the table remain the same.

Table I-6D

Table I-6D is identical to Table I-1, except that the phrase "each $R^s$ is $CO_2^-Li^+$" in each header row is replaced with the phrase "one $R^s$ is $CO_2^-[NH(Me)_3]^+$, the other $R^s$ is $CO_2^-[NH(Et)_3]^+$". The values for $R^a$, $R^b$, $R^c$, $R^d$ and $R^e$ appearing in each header row or within the table remain the same.

Table I-7D

Table I-7D is identical to Table I-1, except that the phrase "each $R^s$ is $CO_2^-Li^+$" in each header row is replaced with the phrase "one $R^s$ is $CO_2^-Na^+$, the other $R^s$ is $CO_2^-[NH(Et)_3]^+$". The values for $R^a$, $R^b$, $R^c$, $R^d$ and $R^e$ appearing in each header row or within the table remain the same.

Table I-8D

Table I-8D is identical to Table I-1, except that the phrase "each $R^s$ is $CO_2^-Li^+$" in each header row is replaced with the phrase "one $R^s$ is $CO_2^-[NH(n-Bu)_3]^+$, the other $R^s$ is $CO_2^-[NH(Et)_3]^+$". The values for $R^a$, $R^b$, $R^c$, $R^d$ and $R^e$ appearing in each header row or within the table remain the same.

Table I-9D

Table I-9D is identical to Table I-1, except that the phrase "each $R^s$ is $CO_2^-Li^+$" in each header row is replaced with the phrase "one $R^s$ is $CO_2^-[NH_2(Ph)_2]^+$, the other $R^s$ is $CO_2^-[NH(Et)_3]^+$". The values for $R^a$, $R^b$, $R^c$, $R^d$ and $R^e$ appearing in each header row or within the table remain the same.

Table I-10D

Table I-10D is identical to Table I-1, except that the phrase "each $R^s$ is $CO_2^-Li^+$" in each header row is replaced with the phrase "one $R^s$ is $CO_2^-[NH_2(Bn)_2]^+$, the other $R^s$ is $CO_2^-[NH(Et)_3]^+$". The values for $R^a$, $R^b$, $R^c$, $R^d$ and $R^e$ appearing in each header row or within the table remain the same.

Table I-11D

Table I-11D is identical to Table I-1, except that the phrase "each $R^s$ is $CO_2^-Li^+$" in each header row is replaced with the phrase "one $R^s$ is $CO_2^-[NH_2(c-Hex)_2]^+$, the other $R^s$ is $CO_2^-[NH(Et)_3]^+$". The values for $R^a$, $R^b$, $R^C$, $R^d$ and $R^e$ appearing in each header row or within the table remain the same.

Table I-12D

Table I-12D is identical to Table I-1, except that the phrase "each $R^s$ is $CO_2^-Li^+$" in each header row is replaced with the phrase "one $R^s$ is $CO_2^-[NH_2(Me)_2]^+$, the other $R^s$ is $CO_2^-[NH(Et)_3]^+$". The values for $R^a$, $R^b$, $R^c$, $R^d$ and $R^e$ appearing in each header row or within the table remain the same.

Table I-13D

Table I-13D is identical to Table I-1, except that the phrase "each $R^s$ is $CO_2^-Li^+$" in each header row is replaced with the phrase "one $R^s$ is $CO_2^-[NH_2(Et)_2]^+$, the other $R^s$ is $CO_2^-[NH(Et)_3]^+$". The values for $R^a$, $R^b$, $R^c$, $R^d$ and $R^e$ appearing in each header row or within the table remain the same.

Table I-14D

Table I-14D is identical to Table I-1, except that the phrase "each $R^s$ is $CO_2^-Li^+$" in each header row is replaced with the phrase "one $R^s$ is $CO_2^-[NHEt(i-Pr)_2]^+$, the other $R^s$ is $CO_2[NH(Et)_3]^+$". The values for $R^a$, $R^b$, $R^c$, $R^d$ and $R^e$ appearing in each header row or within the table remain the same.

TABLE I-15

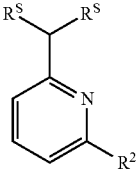

$R^2$ is $CF_3$

| $R^s$ |
|---|
| $CO_2$—$Li^+$ |
| $CO_2$—$Na^+$ |
| $CO_2$—$K^+$ |
| $CO_2$—$[NH_4]^+$ |
| $CO_2$—$[1/2\ Ca]^+$ |
| $CO_2$—$[1/2\ Ba]^+$ |
| $CO_2$—$[NH(Me)_3]^+$ |
| $CO_2$—$[NH(Et)_3]^+$ |
| $CO_2$—$[NH(n-Bu)_3]^+$ |
| $CO_2$—$[NH_2(Ph)_2]^+$ |
| $CO_2$—$[NH_2(Bn)_2]^+$ |
| $CO_2$—$[NH_2(c-Hex)_2]^+$ |

TABLE I-15-continued

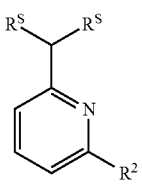

$R^2$ is $CF_3$ $R^S$

CO$_2$—[NH$_2$(Me)$_2$]$^+$
CO$_2$—[NH$_2$(Et)$_2$]$^+$
CO$_2$—[NHEt(i-Pr)$_2$]$^+$

Table I-16 is constructed the same way as Table I-15 except that the phrase "$R^2$ is $CF_3$" in the header row is replaced with the "$R^2$ is H" as shown below for Table I-16. Tables I-17 through I-24 are constructed similarly.

| Table | $R^2$ is |
|---|---|
| I-16 | H |
| I-17 | Cl |
| I-18 | Br |
| I-19 | I |
| I-20 | 2-chloro-4-(trifluoromethyl)phenyl |
| I-21 | 2-fluoro-5-(trifluoromethyl)phenyl |
| I-22 | 2-chloro-4-cyanophenyl |
| I-23 | 2-fluoro-4-cyanophenyl |
| I-24 | 3-chloro-5-trifluoromethyl-2-pyridyl |

TABLE I-25

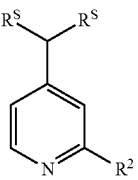

$R^2$ is $CF_3$ $R^S$

CO$_2$—Li$^+$
CO$_2$—Na$^+$
CO$_2$—K$^+$
CO$_2$—[NH$_4$]$^+$
CO$_2$—[1/2 Ca]$^+$
CO$_2$—[1/2 Ba]$^+$
CO$_2$—[NH(Me)$_3$]$^+$
CO$_2$—[NH(Et)$_3$]$^+$
CO$_2$—[NH(n-Bu)$_3$]$^+$
CO$_2$—[NH$_2$(Ph)$_2$]$^+$
CO$_2$—[NH$_2$(Bn)$_2$]$^+$
CO$_2$—[NH$_2$(c-Hex)$_2$]$^+$
CO$_2$—[NH$_2$(Me)$_2$]$^+$
CO$_2$—[NH$_2$(Et)$_2$]$^+$
CO$_2$—[NHEt(i-Pr)$_2$]$^+$

Table I-26 is constructed the same way as Table I-25 except that the phrase "$R^2$ is $CF_3$" in the header row is replaced with the phrase "$R^2$ is H" as shown below for Table I-26. Tables I-27 through I-34 are constructed similarly.

| Table | $R^2$ is |
|---|---|
| I-26 | H |
| I-27 | Cl |
| I-28 | Br |
| I-29 | I |
| I-30 | 2-chloro-4-(trifluoromethyl)phenyl |
| I-31 | 2-fluoro-5-(trifluoromethyl)phenyl |
| I-32 | 2-chloro-4-cyanophenyl |
| I-33 | 2-fluoro-4-cyanophenyl |
| I-34 | 3-chloro-5-trifluoromethyl-2-pyridyl |

TABLE M-1

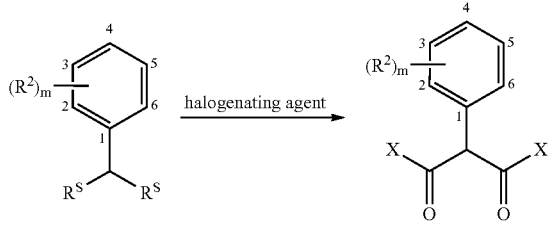

each $R^S$ is CO—Li$^+$; X is Cl; and the halogenating reagent is (COCl)$_2$

| $(R^2)_m$ |
|---|
| 2-F |
| 2-Cl |
| 2-Br |
| 2-I |
| 2-Me |
| 2-Et |
| 2-n-Pr |
| 2-CN |
| 2-OMe |
| 2-OEt |
| 3-F |
| 3-Cl |
| 3-Br |
| 3-I |
| 3-Me |
| 3-Et |
| 3-n-Pr |
| 3-i-Pr |
| 3-OMe |
| 3-OEt |
| 3-t-Bu |
| 3-CF$_3$ |
| 3-CH$_2$F |
| 3-CHF$_2$ |
| 3-O-n-Pr |
| 3-Ph |
| 3-O-i-Pr |
| 3-SF$_5$ |
| 3-OCF$_3$ |
| 3-OCHF$_2$ |
| 3-OCH$_2$F |
| 3-OCH$_2$CF$_3$ |
| 3-SCF$_3$ |
| 3-SCHF$_2$ |
| 3-SCH$_2$F |
| 3-CN |
| 3-Y1 |
| 3-Y2 |
| 3-Y3 |
| 3-Y4 |
| 3-Y5 |
| 3-Y6 |
| 3-Y7 |
| 3-Y8 |
| 3-Y9 |

TABLE M-1-continued

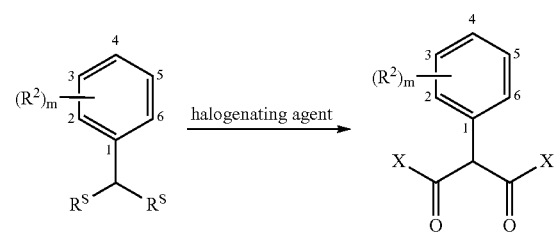

each $R^S$ is CO—Li$^+$; X is Cl; and the halogenating reagent is (COCl)$_2$

| $(R^2)_m$ |
|---|
| 3-Y10 |
| 3-Y11 |
| 3-Y12 |
| 3-Y13 |
| 3-Y14 |
| 3-Y15 |
| 3-Y16 |
| 3-Y17 |
| 3-Y18 |
| 3-Y19 |
| 3-Y20 |
| 3-Y21 |
| 3-Y22 |
| 3-Y23 |
| 3-Y24 |
| 3-Y25 |
| 3-Y26 |
| 3-Y27 |
| 3-Y28 |
| 3-Y29 |
| 3-Y30 |
| 3-Y31 |
| 3-Y32 |
| 3-Y33 |
| 3-Y34 |
| 3-Y35 |
| 3-Y36 |
| 3-Y37 |
| 3-Y38 |
| 3-Y39 |
| 3-Y40 |
| 3-Y41 |
| 4-F |
| 4-Cl |
| 4-Br |
| 4-I |
| 4-Me |
| 4-Et |
| 4-n-Pr |
| 4-i-Pr |
| 4-OMe |
| 4-OEt |
| 4-t-Bu |
| 4-CF$_3$ |
| 4-CH$_2$F |
| 4-CHF$_2$ |
| 4-O-n-Pr |
| 4-Ph |
| 4-O-i-Pr |
| 4-SF$_5$ |
| 4-OCF$_3$ |
| 4-OCHF$_2$ |
| 4-OCH$_2$F |
| 4-OCH$_2$CF$_3$ |
| 4-SCF$_3$ |
| 4-SCHF$_2$ |
| 4-SCH$_2$F |
| 4-CN |
| 2,3-di-F |
| 2-F-3-Cl |
| 2-F-3-Br |
| 2-F-3-I |
| 2-F-3-Me |
| 2-F-3-Et |

TABLE M-1-continued

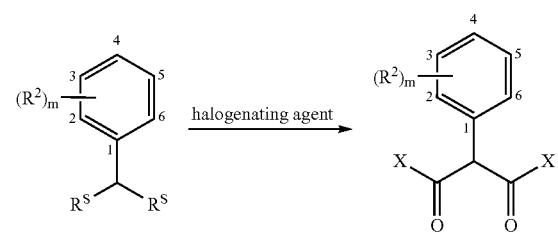

each $R^S$ is CO—Li$^+$; X is Cl; and the halogenating reagent is (COCl)$_2$

| $(R^2)_m$ |
|---|
| 2-F-3-n-Pr |
| 2-F-3-i-Pr |
| 2-F-3-OMe |
| 2-F-3-OEt |
| 2-F-3-t-Bu |
| 2-F-3-CF$_3$ |
| 2-F-3-CH$_2$F |
| 2-F-3-CHF$_2$ |
| 2-F-3-O-n-Pr |
| 2-F-3-Ph |
| 2-F-3-O-i-Pr |
| 2-F-3-SF$_5$ |
| 2-F-3-OCF$_3$ |
| 2-F-3-OCHF$_2$ |
| 2-F-3-OCH$_2$F |
| 2-F-3-OCH$_2$CF$_3$ |
| 2-F-3-SCF$_3$ |
| 2-F-3-SCHF$_2$ |
| 2-F-3-SCH$_2$F |
| 2-F-3-CN |
| 2-F-3-Y1 |
| 2-F-3-Y2 |
| 2-F-3-Y3 |
| 2-F-3-Y4 |
| 2-F-3-Y5 |
| 2-F-3-Y6 |
| 2-F-3-Y7 |
| 2-F-3-Y8 |
| 2-F-3-Y9 |
| 2-F-3-Y10 |
| 2-F-3-Y11 |
| 2-F-3-Y12 |
| 2-F-3-Y13 |
| 2-F-3-Y14 |
| 2-F-3-Y15 |
| 2-F-3-Y16 |
| 2-F-3-Y17 |
| 2-F-3-Y18 |
| 2-F-3-Y19 |
| 2-F-3-Y20 |
| 2-F-3-Y21 |
| 2-F-3-Y22 |
| 2-F-3-Y23 |
| 2-F-3-Y24 |
| 2-F-3-Y25 |
| 2-F-3-Y26 |
| 2-F-3-Y27 |
| 2-F-3-Y28 |
| 2-F-3-Y29 |
| 2-F-3-Y30 |
| 2-F-3-Y31 |
| 2-F-3-Y32 |
| 2-F-3-Y33 |
| 2-F-3-Y34 |
| 2-F-3-Y35 |
| 2-F-3-Y36 |
| 2-F-3-Y37 |
| 2-F-3-Y38 |
| 2-F-3-Y39 |
| 2-F-3-Y40 |
| 2-F-3-Y41 |
| 2,4-di-F |
| 2-F-4-Cl |
| 2-F-4-Br |

TABLE M-1-continued

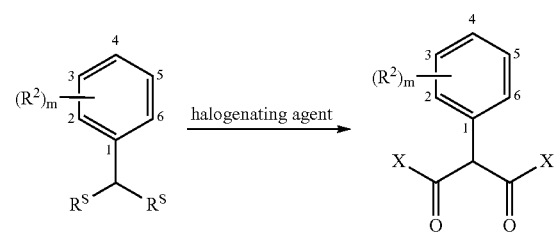

each $R^S$ is CO—Li$^+$; X is Cl; and the halogenating reagent is (COCl)$_2$ ($R^2$)$_m$ 2-F-4-I
2-F-4-Me
2-F-4-Et
2-F-4-n-Pr
2-F-4-i-Pr
2-F-4-OMe
2-F-4-OEt
2-F-4-t-Bu
2-F-4-CF$_3$
2-F-4-CH$_2$F
2-F-4-CHF$_2$
2-F-4-O-n-Pr
2-F-4-Ph
2-F-4-O-i-Pr
2-F-4-SF$_5$
2-F-4-OCF$_3$
2-F-4-OCHF$_2$
2-F-4-OCH$_2$F
2-F-4-OCH$_2$CF$_3$
2-F-4-SCF$_3$
2-F-4-SCHF$_2$
2-F-4-SCH$_2$F
2-F-4-CN
2,5-di-F
2-F-5-Cl
2-F-5-Br
2-F-5-I
2-F-5-Me
2-F-5-Et
2-F-5-n-Pr
2-F-5-i-Pr
2-F-5-OMe
2-F-5-OEt
2-F-5-t-Bu
2-F-5-CF$_3$
2-F-5-CH$_2$F
2-F-5-CHF$_2$
2-F-5-O-n-Pr
2-F-5-Ph
2-F-5-O-i-Pr
2-F-5-SF$_5$
2-F-5-OCF$_3$
2-F-5-OCHF$_2$
2-F-5-OCH$_2$F
2-F-5-OCH$_2$CF$_3$
2-F-5-SCF$_3$
2-F-5-SCHF$_2$
2-F-5-SCH$_2$F
2-F-5-CN
2-F-5-Y1
2-F-5-Y2
2-F-5-Y3
2-F-5-Y4
2-F-5-Y5
2-F-5-Y6
2-F-5-Y7
2-F-5-Y8
2-F-5-Y9
2-F-5-Y10
2-F-5-Y11
2-F-5-Y12
2-F-5-Y13
2-F-5-Y14
2-F-5-Y15

TABLE M-1-continued

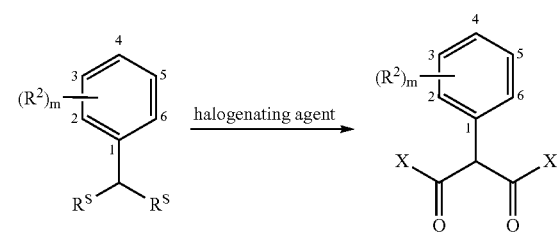

each $R^S$ is CO—Li$^+$; X is Cl; and the halogenating reagent is (COCl)$_2$ ($R^2$)$_m$ 2-F-5-Y16
2-F-5-Y17
2-F-5-Y18
2-F-5-Y19
2-F-5-Y20
2-F-5-Y21
2-F-5-Y22
2-F-5-Y23
2-F-5-Y24
2-F-5-Y25
2-F-5-Y26
2-F-5-Y27
2-F-5-Y28
2-F-5-Y29
2-F-5-Y30
2-F-5-Y31
2-F-5-Y32
2-F-5-Y33
2-F-5-Y34
2-F-5-Y35
2-F-5-Y36
2-F-5-Y37
2-F-5-Y38
2-F-5-Y39
2-F-5-Y40
2-F-5-Y41
2,6-di-F
2-F-6-Cl
2-F-6-Br
2-F-6-I
2-F-6-Me
2-F-6-Et
2-F-6-n-Pr
2-F-6-CN
2-F-6-OMe
2-F-6-OEt
2-MeO-3-F
2-MeO-3-Cl
2-MeO-3-Br
2-MeO-3-I
2-MeO-3-Me
2-MeO-3-Et
2-MeO-3-n-Pr
2-MeO-3-i-Pr
2,3-di-OMe
2-MeO-3-OEt
2-MeO-3-t-Bu
2-MeO-3-CF$_3$
2-MeO-3-CH$_2$F
2-MeO-3-CHF$_2$
2-MeO-3-O-n-Pr
2-MeO-3-Ph
2-MeO-3-O-i-Pr
2-MeO-3-SF$_5$
2-MeO-3-OCF$_3$
2-MeO-3-OCHF$_2$
2-MeO-3-OCH$_2$F
2-MeO-3-OCH$_2$CF$_3$
2-MeO-3-SCF$_3$
2-MeO-3-SCHF$_2$
2-MeO-3-SCH$_2$F
2-MeO-3-CN
2-MeO-3-Y1
2-MeO-3-Y2

TABLE M-1-continued

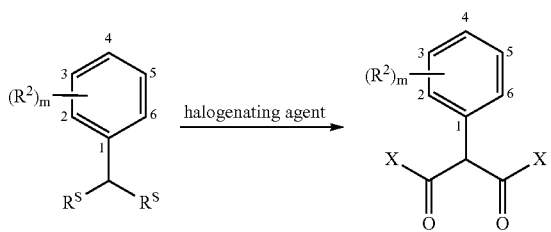

each $R^S$ is CO—Li$^+$; X is Cl; and the halogenating reagent is (COCl)$_2$ $(R^2)_m$ 2-MeO-3-Y3
2-MeO-3-Y4
2-MeO-3-Y5
2-MeO-3-Y6
2-MeO-3-Y7
2-MeO-3-Y8
2-MeO-3-Y9
2-MeO-3-Y10
2-MeO-3-Y11
2-MeO-3-Y12
2-MeO-3-Y13
2-MeO-3-Y14
2-MeO-3-Y15
2-MeO-3-Y16
2-MeO-3-Y17
2-MeO-3-Y18
2-MeO-3-Y19
2-MeO-3-Y20
2-MeO-3-Y21
2-MeO-3-Y22
2-MeO-3-Y23
2-MeO-3-Y24
2-MeO-3-Y25
2-MeO-3-Y26
2-MeO-3-Y27
2-MeO-3-Y28
2-MeO-3-Y29
2-MeO-3-Y30
2-MeO-3-Y31
2-MeO-3-Y32
2-MeO-3-Y33
2-MeO-3-Y34
2-MeO-3-Y35
2-MeO-3-Y36
2-MeO-3-Y37
2-MeO-3-Y38
2-MeO-3-Y39
2-MeO-3-Y40
2-MeO-3-Y41
2-MeO-4-F
2-MeO-4-Cl
2-MeO-4-Br
2-MeO-4-I
2-MeO-4-Me
2-MeO-4-Et
2-MeO-4-n-Pr
2-MeO-4-i-Pr
2,4-di-OMe
2-MeO-4-OEt
2-MeO-4-t-Bu
2-MeO-4-CF$_3$
2-MeO-4-CH$_2$F
2-MeO-4-CHF$_2$
2-MeO-4-O-n-Pr
2-MeO-4-Ph
2-MeO-4-O-i-Pr
2-MeO-4-SF$_5$
2-MeO-4-OCF$_3$
2-MeO-4-OCHF$_2$
2-MeO-4-OCH$_2$F
2-MeO-4-OCH$_2$CF$_3$
2-MeO-4-SCF$_3$
2-MeO-4-SCHF$_2$
2-MeO-4-SCH$_2$F TABLE M-1-continued

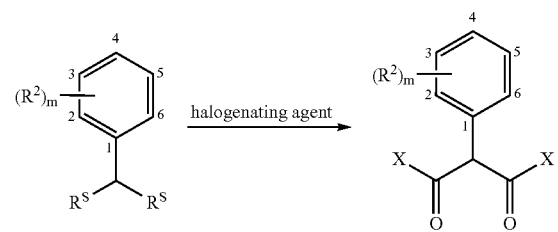

each $R^S$ is CO—Li$^+$; X is Cl; and the halogenating reagent is (COCl)$_2$ $(R^2)_m$ 2-MeO-4-CN
2-MeO-5-F
2-MeO-5-Cl
2-MeO-5-Br
2-MeO-5-I
2-MeO-5-Me
2-MeO-5-Et
2-MeO-5-n-Pr
2-MeO-5-i-Pr
2,5-di-OMe
2-MeO-5-OEt
2-MeO-5-t-Bu
2-MeO-5-CF$_3$
2-MeO-5-CH$_2$F
2-MeO-5-CHF$_2$
2-MeO-5-O-n-Pr
2-MeO-5-Ph
2-MeO-5-O-i-Pr
2-MeO-5-SF$_5$
2-MeO-5-OCF$_3$
2-MeO-5-OCHF$_2$
2-MeO-5-OCH$_2$F
2-MeO-5-OCH$_2$CF$_3$
2-MeO-5-SCF$_3$
2-MeO-5-SCHF$_2$
2-MeO-5-SCH$_2$F
2-MeO-5-CN
2-MeO-5-Y1
2-MeO-5-Y2
2-MeO-5-Y3
2-MeO-5-Y4
2-MeO-5-Y5
2-MeO-5-Y6
2-MeO-5-Y7
2-MeO-5-Y8
2-MeO-5-Y9
2-MeO-5-Y10
2-MeO-5-Y11
2-MeO-5-Y12
2-MeO-5-Y13
2-MeO-5-Y14
2-MeO-5-Y15
2-MeO-5-Y16
2-MeO-5-Y17
2-MeO-5-Y18
2-MeO-5-Y19
2-MeO-5-Y20
2-MeO-5-Y21
2-MeO-5-Y22
2-MeO-5-Y23
2-MeO-5-Y24
2-MeO-5-Y25
2-MeO-5-Y26
2-MeO-5-Y27
2-MeO-5-Y28
2-MeO-5-Y29
2-MeO-5-Y30
2-MeO-5-Y31
2-MeO-5-Y32
2-MeO-5-Y33
2-MeO-5-Y34
2-MeO-5-Y35
2-MeO-5-Y36
2-MeO-5-Y37

TABLE M-1-continued

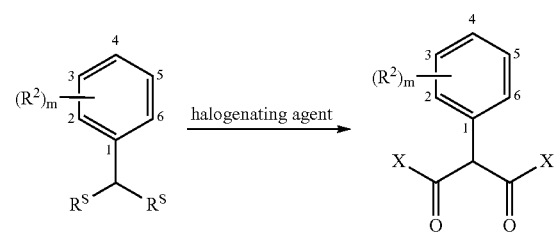

each $R^S$ is CO—Li$^+$; X is Cl; and the halogenating reagent is (COCl)$_2$

| $(R^2)_m$ |
|---|
| 2-MeO-5-Y38 |
| 2-MeO-5-Y39 |
| 2-MeO-5-Y40 |
| 2-MeO-5-Y41 |
| 2-MeO-6-F |
| 2-MeO-6-Cl |
| 2-MeO-6-Br |
| 2-MeO-6-I |
| 2-MeO-6-Me |
| 2-MeO-6-Et |
| 2-MeO-6-n-Pr |
| 2-MeO-6-CN |
| 2,6-di-OMe |
| 2-MeO-6-OEt |
| 3-F-5-Cl |
| 3,5-di-Cl |
| 3-Br-5-Cl |
| 3-i-5-Cl |
| 3-Me-5-Cl |
| 3-Et-5-Cl |
| 3-n-Pr-5-Cl |
| 3-i-Pr-5-Cl |
| 3-OMe-5-Cl |
| 3-OEt-5-Cl |
| 3-t-Bu-5-Cl |
| 3-CF$_3$-5-Cl |
| 3-CH$_2$F-5-Cl |
| 3-CHF$_2$-5-Cl |
| 3-O-n-Pr-5-Cl |
| 3-Ph-5-Cl |
| 3-O-i-Pr-5-Cl |
| 3-SF$_5$-5-Cl |
| 3-OCF$_3$-5-Cl |
| 3-OCHF$_2$-5-Cl |
| 3-OCH$_2$F-5-Cl |
| 3-OCH$_2$CF$_3$-5-Cl |
| 3-SCF$_3$-5-Cl |
| 3-SCHF$_2$-5-Cl |
| 3-SCH$_2$F-5-Cl |
| 3-CN-5-Cl |
| 3-Y1-5-Cl |
| 3-Y2-5-Cl |
| 3-Y3-5-Cl |
| 3-Y4-5-Cl |
| 3-Y5-5-Cl |
| 3-Y6-5-Cl |
| 3-Y7-5-Cl |
| 3-Y8-5-Cl |
| 3-Y9-5-Cl |
| 3-Y10-5-Cl |
| 3-Y11-5-Cl |
| 3-Y12-5-Cl |
| 3-Y13-5-Cl |
| 3-Y14-5-Cl |
| 3-Y15-5-Cl |
| 3-Y16-5-Cl |
| 3-Y17-5-Cl |
| 3-Y18-5-Cl |
| 3-Y19-5-Cl |
| 3-Y20-5-Cl |
| 3-Y21-5-Cl |
| 3-Y22-5-Cl |
| 3-Y23-5-Cl |
| 3-Y24-5-Cl |

TABLE M-1-continued

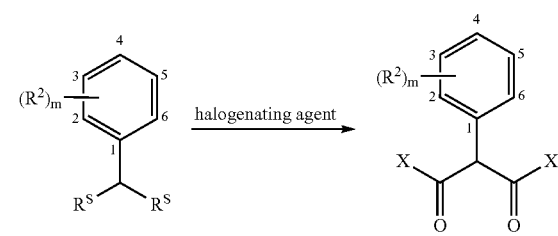

each $R^S$ is CO—Li$^+$; X is Cl; and the halogenating reagent is (COCl)$_2$

| $(R^2)_m$ |
|---|
| 3-Y25-5-Cl |
| 3-Y26-5-Cl |
| 3-Y27-5-Cl |
| 3-Y28-5-Cl |
| 3-Y29-5-Cl |
| 3-Y30-5-Cl |
| 3-Y31-5-Cl |
| 3-Y32-5-Cl |
| 3-Y33-5-Cl |
| 3-Y34-5-Cl |
| 3-Y35-5-Cl |
| 3-Y36-5-Cl |
| 3-Y37-5-Cl |
| 3-Y38-5-Cl |
| 3-Y39-5-Cl |
| 3-Y40-5-Cl |
| 3-Y41-5-Cl |
| 3-F-5-CF$_3$ |
| 3-Cl-5-CF$_3$ |
| 3-Br-5-CF$_3$ |
| 3-i-5-CF$_3$ |
| 3-Me-5-CF$_3$ |
| 3-Et-5-CF$_3$ |
| 3-n-Pr-5-CF$_3$ |
| 3-i-Pr-5-CF$_3$ |
| 3-OMe-5-CF$_3$ |
| 3-OEt-5-CF$_3$ |
| 3-t-Bu-5-CF$_3$ |
| 3,5-di-CF$_3$ |
| 3-CH$_2$F-5-CF$_3$ |
| 3-CHF$_2$-5-CF$_3$ |
| 3-O-n-Pr-5-CF$_3$ |
| 3-Ph-5-CF$_3$ |
| 3-O-i-Pr-5-CF$_3$ |
| 3-SF$_5$-5-CF$_3$ |
| 3-OCF$_3$-5-CF$_3$ |
| 3-OCHF$_2$-5-CF$_3$ |
| 3-OCH$_2$F-5-CF$_3$ |
| 3-OCH$_2$CF$_3$-5-CF$_3$ |
| 3-SCF$_3$-5-CF$_3$ |
| 3-SCHF$_2$-5-CF$_3$ |
| 3-SCH$_2$F-5-CF$_3$ |
| 3-CN-5-CF$_3$ |
| 3-F-5-OCF$_3$ |
| 3-Br-5-OCF$_3$ |
| 3-i-5-OCF$_3$ |
| 3-Me-5-OCF$_3$ |
| 3-Et-5-OCF$_3$ |
| 3-n-Pr-5-OCF$_3$ |
| 3-i-Pr-5-OCF$_3$ |
| 3-OMe-5-OCF$_3$ |
| 3-OEt-5-OCF$_3$ |
| 3-t-Bu-5-OCF$_3$ |
| 3-CF$_3$-5-OCF$_3$ |
| 3-CH$_2$F-5-OCF$_3$ |
| 3-CHF$_2$-5-OCF$_3$ |
| 3-O-n-Pr-5-OCF$_3$ |
| 3-Ph-5-OCF$_3$ |
| 3-O-i-Pr-5-OCF$_3$ |
| 3-SF$_5$-5-OCF$_3$ |
| 3,5-di-OCF$_3$ |
| 3-OCHF$_2$-5-OCF$_3$ |
| 3-OCH$_2$F-5-OCF$_3$ |
| 3-OCH$_2$CF$_3$-5-OCF$_3$ |

TABLE M-1-continued

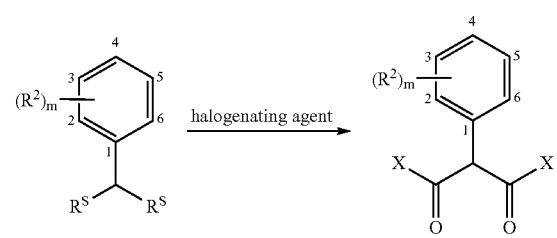

each $R^S$ is CO—Li$^+$; X is Cl; and the halogenating reagent is (COCl)$_2$ ($R^2$)$_m$ 3-SCF$_3$-5-OCF$_3$
3-SCHF$_2$-5-OCF$_3$
3-SCH$_2$F-5-OCF$_3$
3-CN-5-OCF$_3$
3,5-di-F
3-Cl-5-F
3-Br-5-F
3-i-5-F
3-Me-5-F
3-Et-5-F
3-n-Pr-5-F
3-i-Pr-5-F
3-OMe-5-F
3-OEt-5-F
3-t-Bu-5-F
3-CF$_3$-5-F
3-CH$_2$F-5-F
3-CHF$_2$-5-F
3-O-n-Pr-5-F
3-Ph-5-F
3-O-i-Pr-5-F
3-SF$_5$-5-F$_3$
3-OCF$_3$-5-F
3-OCHF$_2$-5-F
3-OCH$_2$F-5-F
3-OCH$_2$CF$_3$-5-F
3-SCF$_3$-5-F
3-SCHF$_2$-5-F
3-SCH$_2$F-5-F
3-CN-5-F
3-F-5-OMe
3-Cl-5-OMe
3-Br-5-OMe
3-i-5-OMe
3-Me-5-OMe
3-Et-5-OMe
3-n-Pr-5-OMe
3-i-Pr-5-OMe
3,5-di-OMe
3-OEt-5-OMe
3-t-Bu-5-OMe
3-CF$_3$-5-OMe
3-CH$_2$F-5-OMe
3-CHF$_2$-5-OMe
3-O-n-Pr-5-OMe
3-Ph-5-OMe
3-O-i-Pr-5-OMe
3-SF$_5$-5-OMe
3-OCF$_3$-5-OMe
3-OCHF$_2$-5-OMe
3-OCH$_2$F-5-OMe
3-OCH$_2$CF$_3$-5-OMe
3-SCF$_3$-5-OMe
3-SCHF$_2$-5-OMe
3-SCH$_2$F-5-OMe
3-CN-5-OMe
2,3,6-tri-F
2,6-di-F-3-Cl
2,6-di-F-3-Br
2,6-di-F-3-I
2,6-di-F-3-Me
2,6-di-F-3-Et
2,6-di-F-3-n-Pr
2,6-di-F-3-i-Pr

TABLE M-1-continued

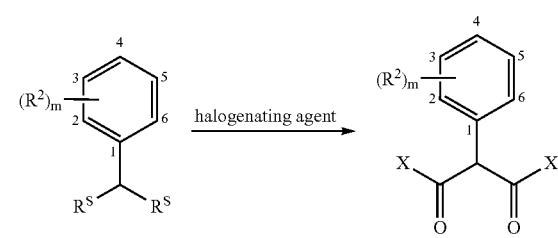

each $R^S$ is CO—Li$^+$; X is Cl; and the halogenating reagent is (COCl)$_2$ ($R^2$)$_m$ 2,6-di-F-3-OMe
2,6-di-F-3-OEt
2,6-di-F-3-t-Bu
2,6-di-F-3-CF$_3$
2,6-di-F-3-CH$_2$F
2,6-di-F-3-CHF$_2$
2,6-di-F-3-O-n-Pr
2,6-di-F-3-Ph
2,6-di-F-3-O-i-Pr
2,6-di-F-3-SF$_5$
2,6-di-F-3-OCF$_3$
2,6-di-F-3-OCHF$_2$
2,6-di-F-3-OCH$_2$F
2,6-di-F-3-OCH$_2$CF$_3$
2,6-di-F-3-SCF$_3$
2,6-di-F-3-SCHF$_2$
2,6-di-F-3-SCH$_2$F
2,6-di-F-3-CN
2,3,5-tri-F
2,3-di-F-5-Cl
2,3-di-F-5-Br
2,3-di-F-5-I
2,3-di-F-5-Me
2,3-di-F-5-Et
2,3-di-F-5-n-Pr
2,3-di-F-5-i-Pr
2,3-di-F-5-OMe
2,3-di-F-5-OEt
2,3-di-F-5-t-Bu
2,3-di-F-5-CF$_3$
2,3-di-F-5-CH$_2$F
2,3-di-F-5-CHF$_2$
2,3-di-F-5-O-n-Pr
2,3-di-F-5-Ph
2,3-di-F-5-O-i-Pr
2,3-di-F-5-SF$_5$
2,3-di-F-5-OCF$_3$
2,3-di-F-5-OCHF$_2$
2,3-di-F-5-OCH$_2$F
2,3-di-F-5-OCH$_2$CF$_3$
2,3-di-F-5-SCF$_3$
2,3-di-F-5-SCHF$_2$
2,3-di-F-5-SCH$_2$F
2,3-di-F-5-CN Table M-2 is constructed the same way as Table M-1 except that the phrase "each $R^s$, X and the halogenating reagent" in the header row of Table M-1 is replaced with the respective "each $R^s$, X and the halogenating reagent" values listed below. For example, the header row in Table M-2 is "each $R^Y$ is CO$_2^-$Na$^+$; X is Cl; and the halogenating reagent is COCl$_2$". Tables M-3 through M-75 are constructed similarly.

| Table | each $R^s$ is | each X is | the halogenating reagent is |
|---|---|---|---|
| M-2 | CO$_2^{-Na+}$ | Cl | COCl$_2$ |
| M-3 | CO$_2^{-K+}$ | Cl | COCl$_2$ |
| M-4 | CO$_2^-$[NH$_4$]$^+$ | Cl | COCl$_2$ |
| M-5 | CO$_2^-$[1/2 Ca]$^+$ | Cl | COCl$_2$ |
| M-6 | CO$_2^-$[1/2 Ba]$^+$ | Cl | COCl$_2$ |

TABLE M-76

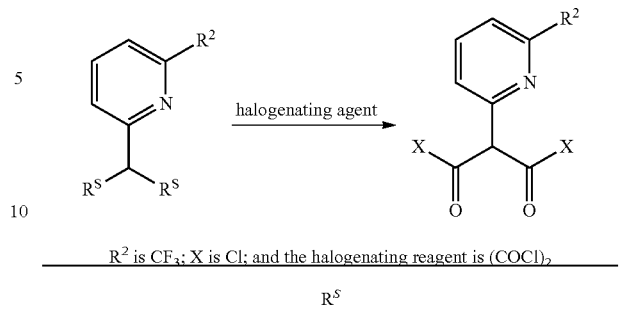

$R^2$ is $CF_3$; X is Cl; and the halogenating reagent is $(COCl)_2$

| $R^S$ |
|---|
| $CO_2$—$Li^+$ |
| $CO_2$—$Na^+$ |
| $CO_2$—$K^+$ |
| $CO_2$—$[NH_4]^+$ |
| $CO_2$—$[1/2\ Ca]^+$ |
| $CO_2$—$[1/2\ Ba]^+$ |
| $CO_2$—$[NH(Me)_3]^+$ |
| $CO_2$—$[NH(Et)_3]^+$ |
| $CO_2$—$[NH(n-Bu)_3]^+$ |
| $CO_2$—$[NH_2(Ph)_2]^+$ |
| $CO_2$—$[NH_2(Bn)_2]^+$ |
| $CO_2$—$[NH_2(c-Hex)_2]^+$ |
| $CO_2$—$[NH_2(Me)_2]^+$ |
| $CO_2$—$[NH_2(Et)_2]^+$ |
| $CO_2$—$[NHEt(i-Pr)_2]^+$ |

Table M-77 is constructed the same way as Table M-76 except that the phrase in the header row (i.e. "$R^2$ is $CF_3$; X is Cl; and the halogenating reagent is $(COCl)_2$") is replaced with the header row for Table M-77 shown below. For example, the header row in Table M-77 is "$R^2$ is H; X is Cl; and the halogenating reagent is $(COCl)_2$". Tables M-78 through M-125 are constructed similarly.

| Table | $R^2$ is | X is | the halogenating reagent is |
|---|---|---|---|
| M-77 | H | Cl | $(COCl)_2$ |
| M-78 | Cl | Cl | $(COCl)_2$ |
| M-79 | Br | Cl | $(COCl)_2$ |
| M-80 | I | Cl | $(COCl)_2$ |
| M-81 | 2-chloro-4-(trifluoromethyl)phenyl | Cl | $(COCl)_2$ |
| M-82 | 2-fluoro-5-(trifluoromethyl)phenyl | Cl | $(COCl)_2$ |
| M-83 | 2-chloro-4-cyanophenyl | Cl | $(COCl)_2$ |
| M-84 | 2-fluoro-4-cyanophenyl | Cl | $(COCl)_2$ |
| M-85 | 3-chloro-5-trifluoromethyl-2-pyridyl | Cl | $(COCl)_2$ |
| M-86 | $CF_3$ | Cl | $SOCl_2$ |
| M-87 | H | Cl | $SOCl_2$ |
| M-88 | Cl | Cl | $SOCl_2$ |
| M-89 | Br | Cl | $SOCl_2$ |
| M-90 | I | Cl | $SOCl_2$ |
| M-91 | 2-chloro-4-(trifluoromethyl)phenyl | Cl | $SOCl_2$ |
| M-92 | 2-fluoro-5-(trifluoromethyl)phenyl | Cl | $SOCl_2$ |
| M-93 | 2-chloro-4-cyanophenyl | Cl | $SOCl_2$ |
| M-94 | 2-fluoro-4-cyanophenyl | Cl | $SOCl_2$ |
| M-95 | 3-chloro-5-trifluoromethyl-2-pyridyl | Cl | $SOCl_2$ |
| M-96 | $CF_3$ | Br | $SOBr_2$ |
| M-97 | H | Br | $SOBr_2$ |
| M-98 | Cl | Br | $SOBr_2$ |
| M-99 | Br | Br | $SOBr_2$ |
| M-100 | I | Br | $SOBr_2$ |
| M-101 | 2-chloro-4-(trifluoromethyl)phenyl | Br | $SOBr_2$ |
| M-102 | 2-fluoro-5-(trifluoromethyl)phenyl | Br | $SOBr_2$ |
| M-103 | 2-chloro-4-cyanophenyl | Br | $SOBr_2$ |
| M-104 | 2-fluoro-4-cyanophenyl | Br | $SOBr_2$ |
| M-105 | 3-chloro-5-trifluoromethyl-2-pyridyl | Br | $SOBr_2$ |
| M-106 | $CF_3$ | Cl | phosgene |
| M-107 | H | Cl | phosgene |
| M-108 | Cl | Cl | phosgene |
| M-109 | Br | Cl | phosgene |
| M-110 | I | Cl | phosgene |

-continued

| Table | each $R^S$ is | each X is | the halogenating reagent is |
|---|---|---|---|
| M-7 | $CO_2^-[NH(Me)_3]^+$ | Cl | $COCl_2$ |
| M-8 | $CO_2^-[NH(Et)_3]^+$ | Cl | $COCl_2$ |
| M-9 | $CO_2^-[NH(n-Bu)_3]^+$ | Cl | $COCl_2$ |
| M-10 | $CO_2^-[NH_2(Ph)_2]^+$ | Cl | $COCl_2$ |
| M-11 | $CO_2^-[NH_2(Bn)_2]^+$ | Cl | $COCl_2$ |
| M-12 | $CO_2^-[NH_2(c-Hex)_2]^+$ | Cl | $COCl_2$ |
| M-13 | $CO_2^-[NH_2(Me)_2]^+$ | Cl | $COCl_2$ |
| M-14 | $CO_2^-[NH_2(Et)_2]^+$ | Cl | $COCl_2$ |
| M-15 | $CO_2^-[NHEt(i-Pr)_2]^+$ | Cl | $COCl_2$ |
| M-16 | $CO_2^-Li^+$ | Cl | $SOCl_2$ |
| M-17 | $CO_2^-Na^+$ | Cl | $SOCl_2$ |
| M-18 | $CO_2^-K^+$ | Cl | $SOCl_2$ |
| M-19 | $CO_2^-[NH_4]^+$ | Cl | $SOCl_2$ |
| M-20 | $CO_2^-[1/2\ Ca]^+$ | Cl | $SOCl_2$ |
| M-21 | $CO_2^-[1/2\ Ba]^+$ | Cl | $SOCl_2$ |
| M-22 | $CO_2^-[NH(Me)_3]^+$ | Cl | $SOCl_2$ |
| M-23 | $CO_2^-[NH(Et)_3]^+$ | Cl | $SOCl_2$ |
| M-24 | $CO_2^-[NH(n-Bu)_3]^+$ | Cl | $SOCl_2$ |
| M-25 | $CO_2^-[NH_2(Ph)_2]^+$ | Cl | $SOCl_2$ |
| M-26 | $CO_2^-[NH_2(Bn)_2]^+$ | Cl | $SOCl_2$ |
| M-27 | $CO_2^-[NH_2(c-Hex)_2]^+$ | Cl | $SOCl_2$ |
| M-28 | $CO_2^-[NH_2(Me)_2]^+$ | Cl | $SOCl_2$ |
| M-29 | $CO_2^-[NH_2(Et)_2]^+$ | Cl | $SOCl_2$ |
| M-30 | $CO_2^-[NHEt(i-Pr)_2]^+$ | Cl | $SOCl_2$ |
| M-31 | $CO_2^-Li^+$ | Cl | triphosgene |
| M-32 | $CO_2^-Na^+$ | Cl | triphosgene |
| M-33 | $CO_2^-K^+$ | Cl | triphosgene |
| M-34 | $CO_2^-[NH_4]^+$ | Cl | triphosgene |
| M-35 | $CO_2^-[1/2\ Ca]^+$ | Cl | triphosgene |
| M-36 | $CO_2^-[1/2\ Ba]^+$ | Cl | triphosgene |
| M-37 | $CO_2^-[NH(Me)_3]^+$ | Cl | triphosgene |
| M-38 | $CO_2^-[NH(Et)_3]^+$ | Cl | triphosgene |
| M-39 | $CO_2^-[NH(n-Bu)_3]^+$ | Cl | triphosgene |
| M-40 | $CO_2^-[NH_2(Ph)_2]^+$ | Cl | triphosgene |
| M-41 | $CO_2^-[NH_2(Bn)_2]^+$ | Cl | triphosgene |
| M-42 | $CO_2^-[NH_2(c-Hex)_2]^+$ | Cl | triphosgene |
| M-43 | $CO_2^-[NH_2(Me)_2]^+$ | Cl | triphosgene |
| M-44 | $CO_2^-[NH_2(Et)_2]^+$ | Cl | triphosgene |
| M-45 | $CO_2^-[NHEt(i-Pr)_2]^+$ | Cl | triphosgene |
| M-46 | $CO_2^-Li^+$ | Br | $SOBr_2$ |
| M-47 | $CO_2^-Na^+$ | Br | $SOBr_2$ |
| M-48 | $CO_2^-K^+$ | Br | $SOBr_2$ |
| M-49 | $CO_2^-[NH_4]^+$ | Br | $SOBr_2$ |
| M-50 | $CO_2^-[1/2\ Ca]^+$ | Br | $SOBr_2$ |
| M-51 | $CO_2^-[1/2\ Ba]^+$ | Br | $SOBr_2$ |
| M-52 | $CO_2^-[NH(Me)_3]^+$ | Br | $SOBr_2$ |
| M-53 | $CO_2^-[NH(Et)_3]^+$ | Br | $SOBr_2$ |
| M-54 | $CO_2^-[NH(n-Bu)_3]^+$ | Br | $SOBr_2$ |
| M-55 | $CO_2^-[NH_2(Ph)_2]^+$ | Br | $SOBr_2$ |
| M-56 | $CO_2^-[NH_2(Bn)_2]^+$ | Br | $SOBr_2$ |
| M-57 | $CO_2^-[NH_2(c-Hex)_2]^+$ | Br | $SOBr_2$ |
| M-58 | $CO_2^-[NH_2(Me)_2]^+$ | Br | $SOBr_2$ |
| M-59 | $CO_2^-[NH_2(Et)_2]^+$ | Br | $SOBr_2$ |
| M-60 | $CO_2^-[NHEt(i-Pr)_2]^+$ | Br | $SOBr_2$ |
| M-61 | $CO_2^-Li^+$ | Cl | phosgene |
| M-62 | $CO_2^-Na^+$ | Cl | phosgene |
| M-63 | $CO_2^-K^+$ | Cl | phosgene |
| M-64 | $CO_2^-[NH_4]^+$ | Cl | phosgene |
| M-65 | $CO_2^-[1/2\ Ca]^+$ | Cl | phosgene |
| M-66 | $CO_2^-[1/2\ Ba]^+$ | Cl | phosgene |
| M-67 | $CO_2^-[NH(Me)_3]^+$ | Cl | phosgene |
| M-68 | $CO_2^-[NH(Et)_3]^+$ | Cl | phosgene |
| M-69 | $CO_2^-[NH(n-Bu)_3]^+$ | Cl | phosgene |
| M-70 | $CO_2^-[NH_2(Ph)_2]^+$ | Cl | phosgene |
| M-71 | $CO_2^-[NH_2(Bn)_2]^+$ | Cl | phosgene |
| M-72 | $CO_2^-[NH_2(c-Hex)_2]^+$ | Cl | phosgene |
| M-73 | $CO_2^-[NH_2(Me)_2]^+$ | Cl | phosgene |
| M-74 | $CO_2^-[NH_2(Et)_2]^+$ | Cl | phosgene |
| M-75 | $CO_2^-[NHEt(i-Pr)_2]^+$ | Cl | phosgene |

-continued

| Table | R² is | X is | the halogenating reagent is |
|---|---|---|---|
| M-111 | 2-chloro-4-(trifluoromethyl)phenyl | Cl | phosgene |
| M-112 | 2-fluoro-5-(trifluoromethyl)phenyl | Cl | phosgene |
| M-113 | 2-chloro-4-cyanophenyl | Cl | phosgene |
| M-114 | 2-fluoro-4-cyanophenyl | Cl | phosgene |
| M-115 | 3-chloro-5-trifluoromethyl-2-pyridyl | Cl | phosgene |
| M-116 | CF₃ | Cl | triphosgene |
| M-117 | H | Cl | triphosgene |
| M-118 | Cl | Cl | triphosgene |
| M-119 | Br | Cl | triphosgene |
| M-120 | I | Cl | triphosgene |
| M-121 | 2-chloro-4-(trifluoromethyl)phenyl | Cl | triphosgene |
| M-122 | 2-fluoro-5-(trifluoromethyl)phenyl | Cl | triphosgene |
| M-123 | 2-chloro-4-cyanophenyl | Cl | triphosgene |
| M-124 | 2-fluoro-4-cyanophenyl | Cl | triphosgene |
| M-125 | 3-chloro-5-trifluoromethyl-2-pyridyl | Cl | triphosgene |

TABLE M-125

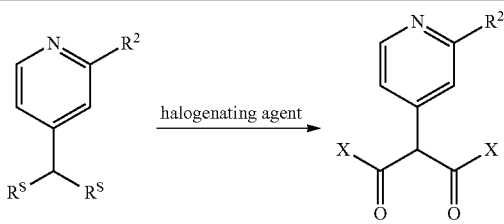

R² is CF₃; X is Cl; and the halogenating reagent is (COCl)₂

| R$^S$ |
|---|
| CO₂—Li⁺ |
| CO₂—Na⁺ |
| CO₂—K⁺ |
| CO₂—[NH₄]⁺ |
| CO₂—[1/2 Ca]⁺ |
| CO₂—[1/2 Ba]⁺ |
| CO₂—[NH(Me)₃]⁺ |
| CO₂—[NH(Et)₃]⁺ |
| CO₂—[NH(n-Bu)₃]⁺ |
| CO₂—[NH₂(Ph)₂]⁺ |
| CO₂—[NH₂(Bn)₂]⁺ |
| CO₂—[NH₂(c-Hex)₂]⁺ |
| CO₂—[NH₂(Me)₂]⁺ |
| CO₂—[NH₂(Et)₂]⁺ |
| CO₂—[NHEt(i-Pr)₂]⁺ |

Table M-126 is constructed the same way as Table M-125 except that the phrase in the header row (i.e. "R² is CF₃; X is Cl; and the halogenating reagent is (COCl)₂") is replaced with the respective header row for Table M-126 listed below. For example, the header row in Table M-126 is "R² is H; X is Cl; and the halogenating reagent is (COCl)₂". Tables M-127 through M-174 are constructed similarly.

| Table | R² is | X is | the halogenating reagent is |
|---|---|---|---|
| M-126 | H | Cl | (COCl)₂ |
| M-127 | Cl | Cl | (COCl)₂ |
| M-128 | Br | Cl | (COCl)₂ |
| M-129 | I | Cl | (COCl)₂ |
| M-130 | 2-chloro-4-(trifluoromethyl)phenyl | Cl | (COCl)₂ |
| M-131 | 2-fluoro-5-(trifluoromethyl)phenyl | Cl | (COCl)₂ |
| M-132 | 2-chloro-4-cyanophenyl | Cl | (COCl)₂ |
| M-133 | 2-fluoro-4-cyanophenyl | Cl | (COCl)₂ |
| M-134 | 3-chloro-5-trifluoromethyl-2-pyridyl | Cl | (COCl)₂ |
| M-135 | CF₃ | Cl | SOCl₂ |

-continued

| Table | R² is | X is | the halogenating reagent is |
|---|---|---|---|
| M-136 | H | Cl | SOCl₂ |
| M-137 | Cl | Cl | SOCl₂ |
| M-138 | Br | Cl | SOCl₂ |
| M-139 | I | Cl | SOCl₂ |
| M-140 | 2-chloro-4-(trifluoromethyl)phenyl | Cl | SOCl₂ |
| M-141 | 2-fluoro-5-(trifluoromethyl)phenyl | Cl | SOCl₂ |
| M-142 | 2-chloro-4-cyanophenyl | Cl | SOCl₂ |
| M-143 | 2-fluoro-4-cyanophenyl | Cl | SOCl₂ |
| M-144 | 3-chloro-5-trifluoromethyl-2-pyridyl | Cl | SOCl₂ |
| M-145 | CF₃ | Br | SOBr₂ |
| M-146 | H | Br | SOBr₂ |
| M-147 | Cl | Br | SOBr₂ |
| M-148 | Br | Br | SOBr₂ |
| M-149 | I | Br | SOBr₂ |
| M-150 | 2-chloro-4-(trifluoromethyl)phenyl | Br | SOBr₂ |
| M-151 | 2-fluoro-5-(trifluoromethyl)phenyl | Br | SOBr₂ |
| M-152 | 2-chloro-4-cyanophenyl | Br | SOBr₂ |
| M-153 | 2-fluoro-4-cyanophenyl | Br | SOBr₂ |
| M-154 | 3-chloro-5-trifluoromethyl-2-pyridyl | Br | SOBr₂ |
| M-155 | CF₃ | Cl | phosgene |
| M-156 | H | Cl | phosgene |
| M-157 | Cl | Cl | phosgene |
| M-158 | Br | Cl | phosgene |
| M-159 | I | Cl | phosgene |
| M-160 | 2-chloro-4-(trifluoromethyl)phenyl | Cl | phosgene |
| M-161 | 2-fluoro-5-(trifluoromethyl)phenyl | Cl | phosgene |
| M-162 | 2-chloro-4-cyanophenyl | Cl | phosgene |
| M-163 | 2-fluoro-4-cyanophenyl | Cl | phosgene |
| M-164 | 3-chloro-5-trifluoromethyl-2-pyridyl | Cl | phosgene |
| M-165 | CF₃ | Cl | triphosgene |
| M-166 | H | Cl | triphosgene |
| M-167 | Cl | Cl | triphosgene |
| M-168 | Br | Cl | triphosgene |
| M-169 | I | Cl | triphosgene |
| M-170 | 2-chloro-4-(trifluoromethyl)phenyl | Cl | triphosgene |
| M-171 | 2-fluoro-5-(trifluoromethyl)phenyl | Cl | triphosgene |
| M-172 | 2-chloro-4-cyanophenyl | Cl | triphosgene |
| M-173 | 2-fluoro-4-cyanophenyl | Cl | triphosgene |
| M-174 | 3-chloro-5-trifluoromethyl-2-pyridyl | Cl | triphosgene |

TABLE C-1

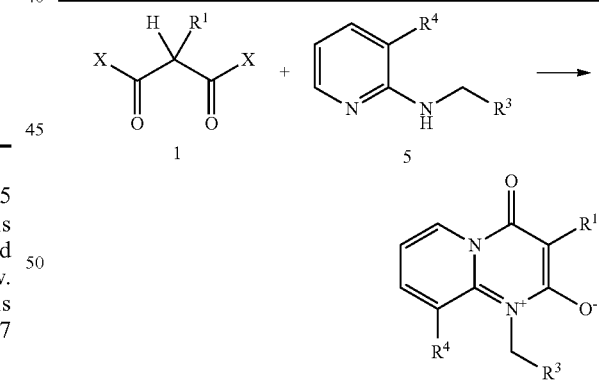

X is Cl; R³ is 2-chloro-5-pyridinyl; R⁴ is H

| (R²)$_m$ |
|---|
| 2-F |
| 2-Cl |
| 2-Br |
| 2-I |
| 2-Me |
| 2-Et |
| 2-n-Pr |
| 2-CN |

TABLE C-1-continued

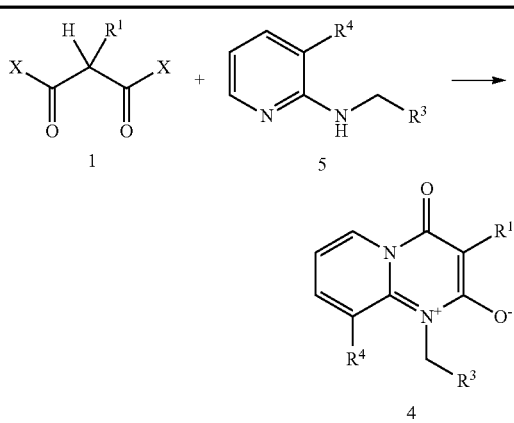

X is Cl; $R^3$ is 2-chloro-5-pyridinyl; $R^4$ is H $(R^2)_m$

2-OMe
2-OEt
3-F
3-Cl
3-Br
3-I
3-Me
3-Et
3-n-Pr
3-i-Pr
3-OMe
3-OEt
3-t-Bu
3-$CF_3$
3-$CH_2F$
3-$CHF_2$
3-O-n-Pr
3-Ph
3-O-i-Pr
3-$SF_5$
3-$OCF_3$
3-$OCHF_2$
3-$OCH_2F$
3-$OCH_2CF_3$
3-$SCF_3$
3-$SCHF_2$
3-$SCH_2F$
3-CN
3-Y1
3-Y2
3-Y3
3-Y4
3-Y5
3-Y6
3-Y7
3-Y8
3-Y9
3-Y10
3-Y11
3-Y12
3-Y13
3-Y14
3-Y15
3-Y16
3-Y17
3-Y18
3-Y19
3-Y20
3-Y21
3-Y22
3-Y23
3-Y24
3-Y25
3-Y26
3-Y27

TABLE C-1-continued

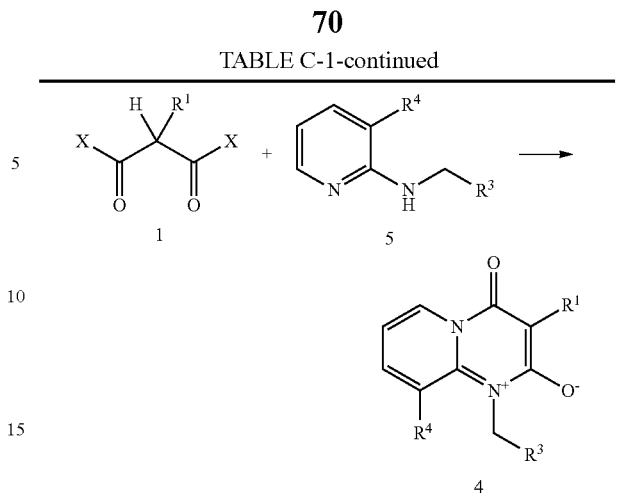

X is Cl; $R^3$ is 2-chloro-5-pyridinyl; $R^4$ is H $(R^2)_m$

3-Y28
3-Y29
3-Y30
3-Y31
3-Y32
3-Y33
3-Y34
3-Y35
3-Y36
3-Y37
3-Y38
3-Y39
3-Y40
3-Y41
4-F
4-Cl
4-Br
4-I
4-Me
4-Et
4-n-Pr
4-i-Pr
4-OMe
4-OEt
4-t-Bu
4-$CF_3$
4-$CH_2F$
4-$CHF_2$
4-O-n-Pr
4-Ph
4-O-i-Pr
4-$SF_5$
4-$OCF_3$
4-$OCHF_2$
4-$OCH_2F$
4-$OCH_2CF_3$
4-$SCF_3$
4-$SCHF_2$
4-$SCH_2F$
4-CN
2,3-di-F
2-F-3-Cl
2-F-3-Br
2-F-3-I
2-F-3-Me
2-F-3-Et
2-F-3-n-Pr
2-F-3-i-Pr
2-F-3-OMe
2-F-3-OEt
2-F-3-t-Bu
2-F-3-$CF_3$
2-F-3-$CH_2F$
2-F-3-$CHF_2$
2-F-3-O-n-Pr

TABLE C-1-continued

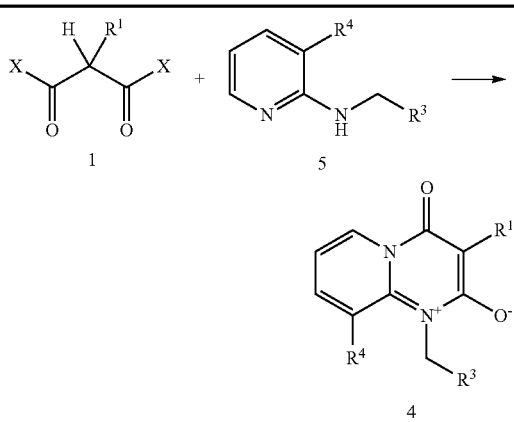

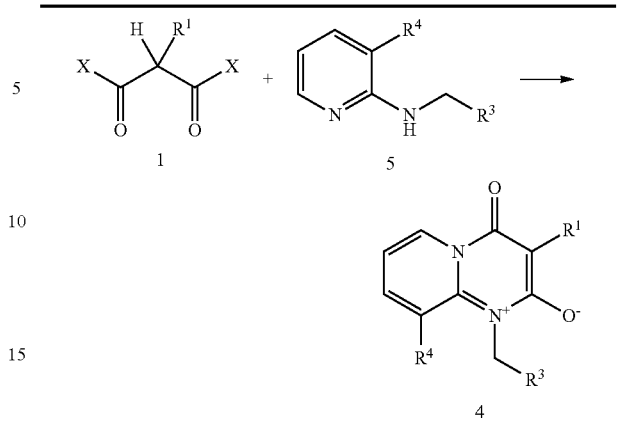

X is Cl; R³ is 2-chloro-5-pyridinyl; R⁴ is H

| (R²)ₘ | (R²)ₘ |
|---|---|
| 2-F-3-Ph | 2-F-4-I |
| 2-F-3-O-i-Pr | 2-F-4-Me |
| 2-F-3-SF₅ | 2-F-4-Et |
| 2-F-3-OCF₃ | 2-F-4-n-Pr |
| 2-F-3-OCHF₂ | 2-F-4-i-Pr |
| 2-F-3-OCH₂F | 2-F-4-OMe |
| 2-F-3-OCH₂CF₃ | 2-F-4-OEt |
| 2-F-3-SCF₃ | 2-F-4-t-Bu |
| 2-F-3-SCHF₂ | 2-F-4-CF₃ |
| 2-F-3-SCH₂F | 2-F-4-CH₂F |
| 2-F-3-CN | 2-F-4-CHF₂ |
| 2-F-3-Y1 | 2-F-4-O-n-Pr |
| 2-F-3-Y2 | 2-F-4-Ph |
| 2-F-3-Y3 | 2-F-4-O-i-Pr |
| 2-F-3-Y4 | 2-F-4-SF₅ |
| 2-F-3-Y5 | 2-F-4-OCF₃ |
| 2-F-3-Y6 | 2-F-4-OCHF₂ |
| 2-F-3-Y7 | 2-F-4-OCH₂F |
| 2-F-3-Y8 | 2-F-4-OCH₂CF₃ |
| 2-F-3-Y9 | 2-F-4-SCF₃ |
| 2-F-3-Y10 | 2-F-4-SCHF₂ |
| 2-F-3-Y11 | 2-F-4-SCH₂F |
| 2-F-3-Y12 | 2-F-4-CN |
| 2-F-3-Y13 | 2,5-di-F |
| 2-F-3-Y14 | 2-F-5-Cl |
| 2-F-3-Y15 | 2-F-5-Br |
| 2-F-3-Y16 | 2-F-5-I |
| 2-F-3-Y17 | 2-F-5-Me |
| 2-F-3-Y18 | 2-F-5-Et |
| 2-F-3-Y19 | 2-F-5-n-Pr |
| 2-F-3-Y20 | 2-F-5-i-Pr |
| 2-F-3-Y21 | 2-F-5-OMe |
| 2-F-3-Y22 | 2-F-5-OEt |
| 2-F-3-Y23 | 2-F-5-t-Bu |
| 2-F-3-Y24 | 2-F-5-CF₃ |
| 2-F-3-Y25 | 2-F-5-CH₂F |
| 2-F-3-Y26 | 2-F-5-CHF₂ |
| 2-F-3-Y27 | 2-F-5-O-n-Pr |
| 2-F-3-Y28 | 2-F-5-Ph |
| 2-F-3-Y29 | 2-F-5-O-i-Pr |
| 2-F-3-Y30 | 2-F-5-SF₅ |
| 2-F-3-Y31 | 2-F-5-OCF₃ |
| 2-F-3-Y32 | 2-F-5-OCHF₂ |
| 2-F-3-Y33 | 2-F-5-OCH₂F |
| 2-F-3-Y34 | 2-F-5-OCH₂CF₃ |
| 2-F-3-Y35 | 2-F-5-SCF₃ |
| 2-F-3-Y36 | 2-F-5-SCHF₂ |
| 2-F-3-Y37 | 2-F-5-SCH₂F |
| 2-F-3-Y38 | 2-F-5-CN |
| 2-F-3-Y39 | 2-F-5-Y1 |
| 2-F-3-Y40 | 2-F-5-Y2 |
| 2-F-3-Y41 | 2-F-5-Y3 |
| 2,4-di-F | 2-F-5-Y4 |
| 2-F-4-Cl | 2-F-5-Y5 |
| 2-F-4-Br | 2-F-5-Y6 |

TABLE C-1-continued

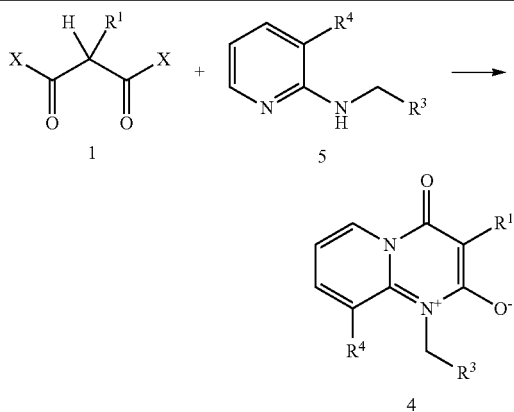

X is Cl; R³ is 2-chloro-5-pyridinyl; R⁴ is H (R²)ₘ

2-F-5-Y7
2-F-5-Y8
2-F-5-Y9
2-F-5-Y10
2-F-5-Y11
2-F-5-Y12
2-F-5-Y13
2-F-5-Y14
2-F-5-Y15
2-F-5-Y16
2-F-5-Y17
2-F-5-Y18
2-F-5-Y19
2-F-5-Y20
2-F-5-Y21
2-F-5-Y22
2-F-5-Y23
2-F-5-Y24
2-F-5-Y25
2-F-5-Y26
2-F-5-Y27
2-F-5-Y28
2-F-5-Y29
2-F-5-Y30
2-F-5-Y31
2-F-5-Y32
2-F-5-Y33
2-F-5-Y34
2-F-5-Y35
2-F-5-Y36
2-F-5-Y37
2-F-5-Y38
2-F-5-Y39
2-F-5-Y40
2-F-5-Y41
2,6-di-F
2-F-6-Cl
2-F-6-Br
2-F-6-I
2-F-6-Me
2-F-6-Et
2-F-6-n-Pr
2-F-6-CN
2-F-6-OMe
2-F-6-OEt
2-MeO-3-F
2-MeO-3-Cl
2-MeO-3-Br
2-MeO-3-I
2-MeO-3-Me
2-MeO-3-Et
2-MeO-3-n-Pr
2-MeO-3-i-Pr
2,3-di-OMe
2-MeO-3-OEt

TABLE C-1-continued

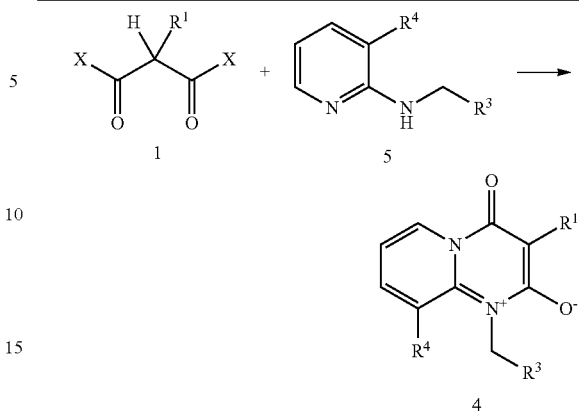

X is Cl; R³ is 2-chloro-5-pyridinyl; R⁴ is H (R²)ₘ

2-MeO-3-t-Bu
2-MeO-3-CF₃
2-MeO-3-CH₂F
2-MeO-3-CHF₂
2-MeO-3-O-n-Pr
2-MeO-3-Ph
2-MeO-3-O-i-Pr
2-MeO-3-SF₅
2-MeO-3-OCF₃
2-MeO-3-OCHF₂
2-MeO-3-OCH₂F
2-MeO-3-OCH₂CF₃
2-MeO-3-SCF₃
2-MeO-3-SCHF₂
2-MeO-3-SCH₂F
2-MeO-3-CN
2-MeO-3-Y1
2-MeO-3-Y2
2-MeO-3-Y3
2-MeO-3-Y4
2-MeO-3-Y5
2-MeO-3-Y6
2-MeO-3-Y7
2-MeO-3-Y8
2-MeO-3-Y9
2-MeO-3-Y10
2-MeO-3-Y11
2-MeO-3-Y12
2-MeO-3-Y13
2-MeO-3-Y14
2-MeO-3-Y15
2-MeO-3-Y16
2-MeO-3-Y17
2-MeO-3-Y18
2-MeO-3-Y19
2-MeO-3-Y20
2-MeO-3-Y21
2-MeO-3-Y22
2-MeO-3-Y23
2-MeO-3-Y24
2-MeO-3-Y25
2-MeO-3-Y26
2-MeO-3-Y27
2-MeO-3-Y28
2-MeO-3-Y29
2-MeO-3-Y30
2-MeO-3-Y31
2-MeO-3-Y32
2-MeO-3-Y33
2-MeO-3-Y34
2-MeO-3-Y35
2-MeO-3-Y36
2-MeO-3-Y37
2-MeO-3-Y38
2-MeO-3-Y39

TABLE C-1-continued

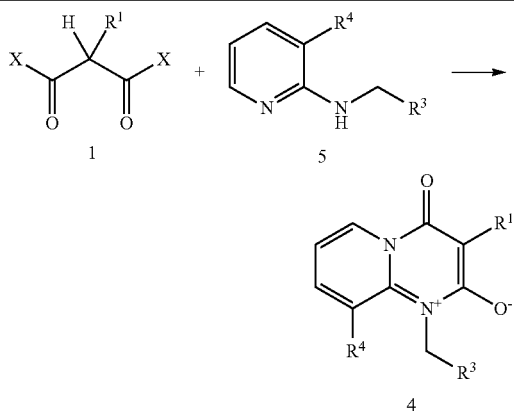

X is Cl; R³ is 2-chloro-5-pyridinyl; R⁴ is H $(R^2)_m$

2-MeO-3-Y40
2-MeO-3-Y41
2-MeO-4-F
2-MeO-4-Cl
2-MeO-4-Br
2-MeO-4-I
2-MeO-4-Me
2-MeO-4-Et
2-MeO-4-n-Pr
2-MeO-4-i-Pr
2,4-di-OMe
2-MeO-4-OEt
2-MeO-4-t-Bu
2-MeO-4-CF₃
2-MeO-4-CH₂F
2-MeO-4-CHF₂
2-MeO-4-O-n-Pr
2-MeO-4-Ph
2-MeO-4-O-i-Pr
2-MeO-4-SF₅
2-MeO-4-OCF₃
2-MeO-4-OCHF₂
2-MeO-4-OCH₂F
2-MeO-4-OCH₂CF₃
2-MeO-4-SCF₃
2-MeO-4-SCHF₂
2-MeO-4-SCH₂F
2-MeO-4-CN
2-MeO-5-F
2-MeO-5-Cl
2-MeO-5-Br
2-MeO-5-I
2-MeO-5-Me
2-MeO-5-Et
2-MeO-5-n-Pr
2-MeO-5-i-Pr
2,5-di-OMe
2-MeO-5-OEt
2-MeO-5-t-Bu
2-MeO-5-CF₃
2-MeO-5-CH₂F
2-MeO-5-CHF₂
2-MeO-5-O-n-Pr
2-MeO-5-Ph
2-MeO-5-O-i-Pr
2-MeO-5-SF₅
2-MeO-5-OCF₃
2-MeO-5-OCHF₂
2-MeO-5-OCH₂F
2-MeO-5-OCH₂CF₃
2-MeO-5-SCF₃
2-MeO-5-SCHF₂
2-MeO-5-SCH₂F
2-MeO-5-CN
2-MeO-5-Y1

TABLE C-1-continued

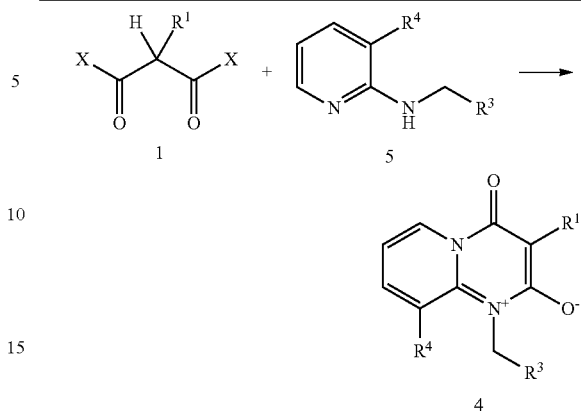

X is Cl; R³ is 2-chloro-5-pyridinyl; R⁴ is H $(R^2)_m$

2-MeO-5-Y2
2-MeO-5-Y3
2-MeO-5-Y4
2-MeO-5-Y5
2-MeO-5-Y6
2-MeO-5-Y7
2-MeO-5-Y8
2-MeO-5-Y9
2-MeO-5-Y10
2-MeO-5-Y11
2-MeO-5-Y12
2-MeO-5-Y13
2-MeO-5-Y14
2-MeO-5-Y15
2-MeO-5-Y16
2-MeO-5-Y17
2-MeO-5-Y18
2-MeO-5-Y19
2-MeO-5-Y20
2-MeO-5-Y21
2-MeO-5-Y22
2-MeO-5-Y23
2-MeO-5-Y24
2-MeO-5-Y25
2-MeO-5-Y26
2-MeO-5-Y27
2-MeO-5-Y28
2-MeO-5-Y29
2-MeO-5-Y30
2-MeO-5-Y31
2-MeO-5-Y32
2-MeO-5-Y33
2-MeO-5-Y34
2-MeO-5-Y35
2-MeO-5-Y36
2-MeO-5-Y37
2-MeO-5-Y38
2-MeO-5-Y39
2-MeO-5-Y40
2-MeO-5-Y41
2-MeO-6-F
2-MeO-6-Cl
2-MeO-6-Br
2-MeO-6-I
2-MeO-6-Me
2-MeO-6-Et
2-MeO-6-n-Pr
2-MeO-6-CN
2,6-di-OMe
2-MeO-6-OEt
3-F-5-Cl
3,5-di-Cl
3-Br-5-Cl
3-i-5-Cl
3-Me-5-Cl

TABLE C-1-continued

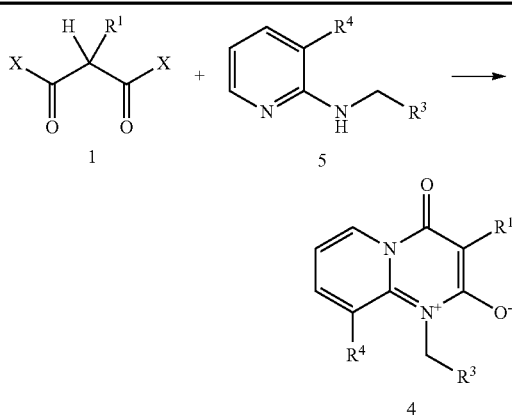

X is Cl; R³ is 2-chloro-5-pyridinyl; R⁴ is H (R²)$_m$

3-Et-5-Cl
3-n-Pr-5-Cl
3-i-Pr-5-Cl
3-OMe-5-Cl
3-OEt-5-Cl
3-t-Bu-5-Cl
3-CF$_3$-5-Cl
3-CH$_2$F-5-Cl
3-CHF$_2$-5-Cl
3-O-n-Pr-5-Cl
3-Ph-5-Cl
3-O-i-Pr-5-Cl
3-SF$_5$-5-Cl
3-OCF$_3$-5-Cl
3-OCHF$_2$-5-Cl
3-OCH$_2$F-5-Cl
3-OCH$_2$CF$_3$-5-Cl
3-SCF$_3$-5-Cl
3-SCHF$_2$-5-Cl
3-SCH$_2$F-5-Cl
3-CN-5-Cl
3-Y1-5-Cl
3-Y2-5-Cl
3-Y3-5-Cl
3-Y4-5-Cl
3-Y5-5-Cl
3-Y6-5-Cl
3-Y7-5-Cl
3-Y8-5-Cl
3-Y9-5-Cl
3-Y10-5-Cl
3-Y11-5-Cl
3-Y12-5-Cl
3-Y13-5-Cl
3-Y14-5-Cl
3-Y15-5-Cl
3-Y16-5-Cl
3-Y17-5-Cl
3-Y18-5-Cl
3-Y19-5-Cl
3-Y20-5-Cl
3-Y21-5-Cl
3-Y22-5-Cl
3-Y23-5-Cl
3-Y24-5-Cl
3-Y25-5-Cl
3-Y26-5-Cl
3-Y27-5-Cl
3-Y28-5-Cl
3-Y29-5-Cl
3-Y30-5-Cl
3-Y31-5-Cl
3-Y32-5-Cl
3-Y33-5-Cl
3-Y34-5-Cl

TABLE C-1-continued

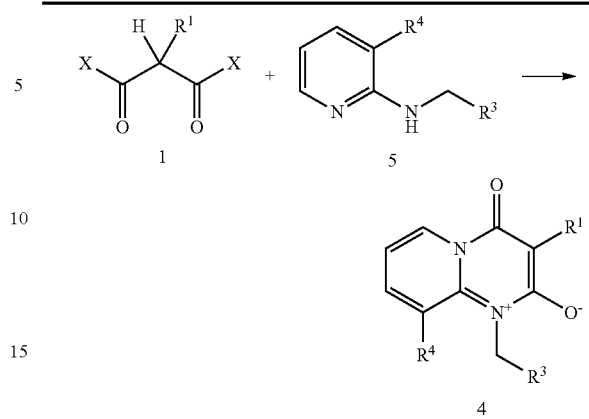

X is Cl; R³ is 2-chloro-5-pyridinyl; R⁴ is H (R²)$_m$

3-Y35-5-Cl
3-Y36-5-Cl
3-Y37-5-Cl
3-Y38-5-Cl
3-Y39-5-Cl
3-Y40-5-Cl
3-Y41-5-Cl
3-F-5-CF$_3$
3-Cl-5-CF$_3$
3-Br-5-CF$_3$
3-i-5-CF$_3$
3-Me-5-CF$_3$
3-Et-5-CF$_3$
3-n-Pr-5-CF$_3$
3-i-Pr-5-CF$_3$
3-OMe-5-CF$_3$
3-OEt-5-CF$_3$
3-t-Bu-5-CF$_3$
3,5-di-CF$_3$
3-CH$_2$F-5-CF$_3$
3-CHF$_2$-5-CF$_3$
3-O-n-Pr-5-CF$_3$
3-Ph-5-CF$_3$
3-O-i-Pr-5-CF$_3$
3-SF$_5$-5-CF$_3$
3-OCF$_3$-5-CF$_3$
3-OCHF$_2$-5-CF$_3$
3-OCH$_2$F-5-CF$_3$
3-OCH$_2$CF$_3$-5-CF$_3$
3-SCF$_3$-5-CF$_3$
3-SCHF$_2$-5-CF$_3$
3-SCH$_2$F-5-CF$_3$
3-CN-5-CF$_3$
3-F-5-OCF$_3$
3-Cl-5-OCF$_3$
3-Br-5-OCF$_3$
3-i-5-OCF$_3$
3-Me-5-OCF$_3$
3-Et-5-OCF$_3$
3-n-Pr-5-OCF$_3$
3-i-Pr-5-OCF$_3$
3-OMe-5-OCF$_3$
3-OEt-5-OCF$_3$
3-t-Bu-5-OCF$_3$
3-CF$_3$-5-OCF$_3$
3-CH$_2$F-5-OCF$_3$
3-CHF$_2$-5-OCF$_3$
3-O-n-Pr-5-OCF$_3$
3-Ph-5-OCF$_3$
3-O-i-Pr-5-OCF$_3$
3-SF$_5$-5-OCF$_3$
3,5-di-OCF$_3$
3-OCHF$_2$-5-OCF$_3$
3-OCH$_2$F-5-OCF$_3$
3-OCH$_2$CF$_3$-5-OCF$_3$

TABLE C-1-continued

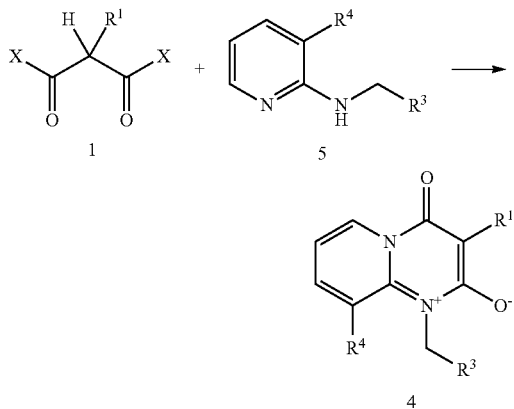

X is Cl; R³ is 2-chloro-5-pyridinyl; R⁴ is H (R²)ₘ

3-SCF₃-5-OCF₃
3-SCHF₂-5-OCF₃
3-SCH₂F-5-OCF₃
3-CN-5-OCF₃
3,5-di-F
3-Cl-5-F
3-Br-5-F
3-i-5-F₃
3-Me-5-F
3-Et-5-F
3-n-Pr-5-F
3-i-Pr-5-F
3-OMe-5-F
3-OEt-5-F
3-t-Bu-5-F
3-CF₃-5-F
3-CH₂F-5-F
3-CHF₂-5-F
3-O-n-Pr-5-F
3-Ph-5-F
3-O-i-Pr-5-F
3-SF₅-5-F₃
3-OCF₃-5-F
3-OCHF₂-5-F
3-OCH₂F-5-F
3-OCH₂CF₃-5-F
3-SCF₃-5-F
3-SCHF₂-5-F
3-SCH₂F-5-F
3-CN-5-F
3-F-5-OMe
3-Cl-5-OMe
3-Br-5-OMe
3-i-5-OMe
3-Me-5-OMe
3-Et-5-OMe
3-n-Pr-5-OMe
3-i-Pr-5-OMe
3,5-di-OMe
3-OEt-5-OMe
3-t-Bu-5-OMe
3-CF₃-5-OMe
3-CH₂F-5-OMe
3-CHF₂-5-OMe
3-O-n-Pr-5-OMe
3-Ph-5-OMe
3-O-i-Pr-5-OMe
3-SF₅-5-OMe
3-OCF₃-5-OMe
3-OCHF₂-5-OMe
3-OCH₂F-5-OMe
3-OCH₂CF₃-5-OMe
3-SCF₃-5-OMe
3-SCHF₂-5-OMe
3-SCH₂F-5-OMe

TABLE C-1-continued

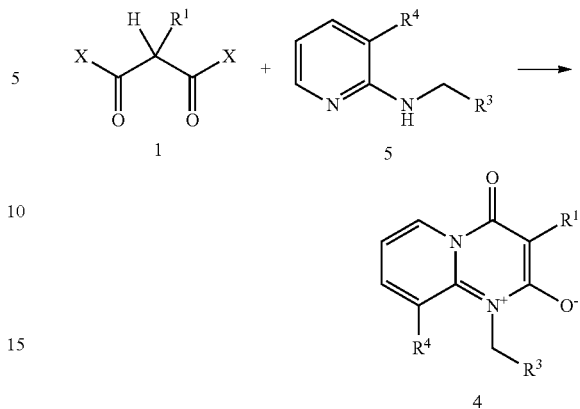

X is Cl; R³ is 2-chloro-5-pyridinyl; R⁴ is H (R²)ₘ

3-CN-5-OMe
2,3,6-tri-F
2,6-di-F-3-Cl
2,6-di-F-3-Br
2,6-di-F-3-I
2,6-di-F-3-Me
2,6-di-F-3-Et
2,6-di-F-3-n-Pr
2,6-di-F-3-i-Pr
2,6-di-F-3-OMe
2,6-di-F-3-OEt
2,6-di-F-3-t-Bu
2,6-di-F-3-CF₃
2,6-di-F-3-CH₂F
2,6-di-F-3-CHF₂
2,6-di-F-3-O-n-Pr
2,6-di-F-3-Ph
2,6-di-F-3-O-i-Pr
2,6-di-F-3-SF₅
2,6-di-F-3-OCF₃
2,6-di-F-3-OCHF₂
2,6-di-F-3-OCH₂F
2,6-di-F-3-OCH₂CF₃
2,6-di-F-3-SCF₃
2,6-di-F-3-SCHF₂
2,6-di-F-3-SCH₂F
2,6-di-F-3-CN
2,3,5-tri-F
2,3-di-F-5-Cl
2,3-di-F-5-Br
2,3-di-F-5-I
2,3-di-F-5-Me
2,3-di-F-5-Et
2,3-di-F-5-n-Pr
2,3-di-F-5-i-Pr
2,3-di-F-5-OMe
2,3-di-F-5-OEt
2,3-di-F-5-t-Bu
2,3-di-F-5-CF₃
2,3-di-F-5-CH₂F
2,3-di-F-5-CHF₂
2,3-di-F-5-O-n-Pr
2,3-di-F-5-Ph
2,3-di-F-5-O-i-Pr
2,3-di-F-5-SF₅
2,3-di-F-5-OCF₃
2,3-di-F-5-OCHF₂
2,3-di-F-5-OCH₂F
2,3-di-F-5-OCH₂CF₃
2,3-di-F-5-SCF₃
2,3-di-F-5-SCHF₂
2,3-di-F-5-SCH₂F
2,3-di-F-5-CN Table C-2 is constructed the same way as Table C-1 except that the phrase in the header row (i.e. "X is Cl; $R^3$ is 2-chloro-5-pyridinyl; $R^4$ is H") is replaced with the phrase listed for Table C-2 below. For example, the header row in Table C-2 is "X is Cl; $R^3$ is 5-pyrimidinyl; $R^4$ is H". Tables C-3 through C-14 are constructed similarly.

| Table | Row Heading |
| --- | --- |
| C-2 | X is Cl; $R^3$ is 5-pyrimidinyl; $R^4$ is H |
| C-3 | X is Cl; $R^3$ is 2-Me-5-pyrimidinyl; $R^4$ is H |
| C-4 | X is Cl; $R^3$ is 5-thiazolyl; $R^4$ is H |
| C-5 | X is Cl; $R^3$ is 2-Me-5-thiazolyl; $R^4$ is H |
| C-6 | X is Cl; $R^3$ is 2-Cl-5-thiazolyl; $R^4$ is H |
| C-7 | X is Cl; $R^3$ is 2-Cl-5-thiazolyl; $R^4$ is Me |
| C-8 | X is Br; $R^3$ is 2-chloro-5-pyridinyl; $R^4$ is H |
| C-9 | X is Br; $R^3$ is 5-pyrimidinyl; $R^4$ is H |
| C-10 | X is Br; $R^3$ is 2-Me-5-pyrimidinyl; $R^4$ is H |
| C-11 | X is Br; $R^3$ is 5-thiazolyl; $R^4$ is H |
| C-12 | X is Br; $R^3$ is 2-Me-5-thiazolyl; $R^4$ is H |
| C-13 | X is Br; $R^3$ is 2-Cl-5-thiazolyl; $R^4$ is H |
| C-14 | X is Br; $R^3$ is 2-Cl-5-thiazolyl; $R^4$ is Me |

TABLE C-15

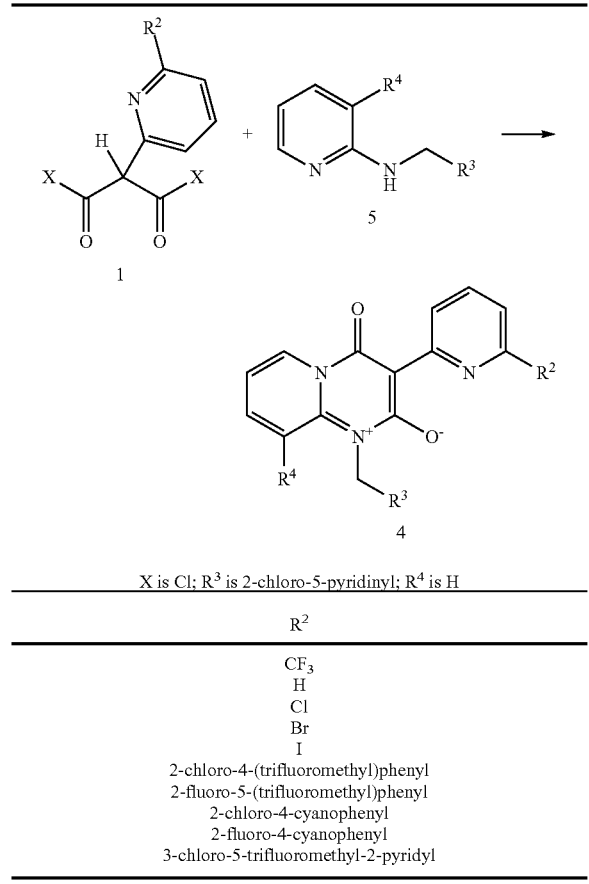

X is Cl; $R^3$ is 2-chloro-5-pyridinyl; $R^4$ is H $R^2$

CF$_3$
H
Cl
Br
I
2-chloro-4-(trifluoromethyl)phenyl
2-fluoro-5-(trifluoromethyl)phenyl
2-chloro-4-cyanophenyl
2-fluoro-4-cyanophenyl
3-chloro-5-trifluoromethyl-2-pyridyl Table C-16 is constructed the same way as Table C-15 except that the phrase in the header row (i.e. "X is Cl; $R^3$ is 2-chloro-5-pyridinyl; $R^4$ is H") is replaced with the phrase listed for Table C-16 below. For example, the header row in Table C-16 is "X is Cl; $R^3$ is 5-pyrimidinyl; $R^4$ is H". Tables C-17 through C-28 are constructed similarly.

| Table | Row Heading |
| --- | --- |
| C-16 | X is Cl; $R^3$ is 5-pyrimidinyl; $R^4$ is H |
| C-17 | X is Cl; $R^3$ is 2-Me-5-pyrimidinyl; $R^4$ is H |
| C-18 | X is Cl; $R^3$ is 5-thiazolyl; $R^4$ is H |
| C-19 | X is Cl; $R^3$ is 2-Me-5-thiazolyl; $R^4$ is H |
| C-20 | X is Cl; $R^3$ is 2-Cl-5-thiazolyl; $R^4$ is H |
| C-21 | X is Cl; $R^3$ is 2-Cl-5-thiazolyl; $R^4$ is Me |
| C-22 | X is Br; $R^3$ is 2-chloro-5-pyridinyl; $R^4$ is H |
| C-23 | X is Br; $R^3$ is 5-pyrimidinyl; $R^4$ is H |
| C-24 | X is Br; $R^3$ is 2-Me-5-pyrimidinyl; $R^4$ is H |
| C-25 | X is Br; $R^3$ is 5-thiazolyl; $R^4$ is H |
| C-26 | X is Br; $R^3$ is 2-Me-5-thiazolyl; $R^4$ is H |
| C-27 | X is Br; $R^3$ is 2-Cl-5-thiazolyl; $R^4$ is H |
| C-28 | X is Br; $R^3$ is 2-Cl-5-thiazolyl; $R^4$ is Me |

TABLE C-29

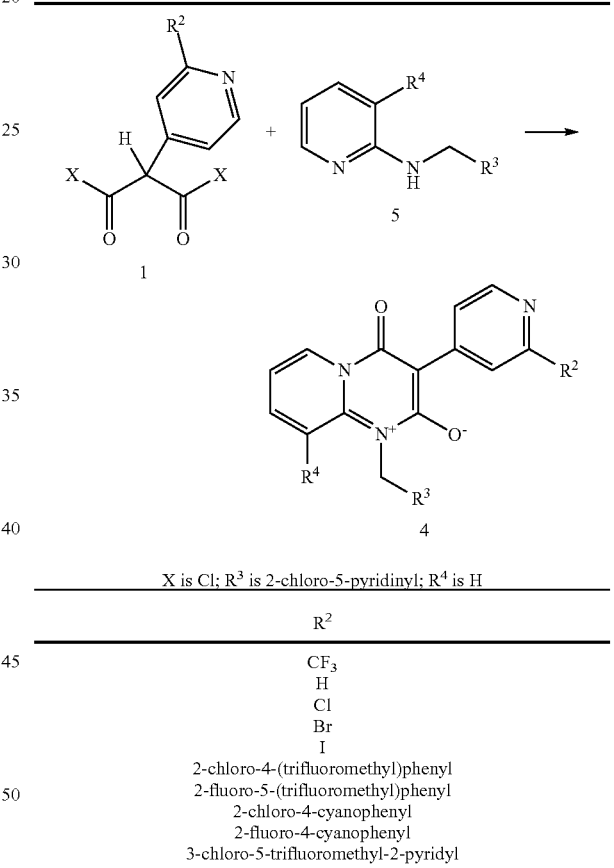

X is Cl; $R^3$ is 2-chloro-5-pyridinyl; $R^4$ is H $R^2$

CF$_3$
H
Cl
Br
I
2-chloro-4-(trifluoromethyl)phenyl
2-fluoro-5-(trifluoromethyl)phenyl
2-chloro-4-cyanophenyl
2-fluoro-4-cyanophenyl
3-chloro-5-trifluoromethyl-2-pyridyl Table C-30 is constructed the same way as Table C-29 except that the phrase in the header row (i.e. "X is Cl; $R^3$ is 2-chloro-5-pyridinyl; $R^4$ is H") is replaced with the phrase listed for Table C-30 below. For example, the header row in Table C-30 is "X is Cl; $R^3$ is 5-pyrimidinyl; $R^4$ is H". Tables C-31 through C-42 are constructed similarly.

| Table | Row Heading |
| --- | --- |
| C-30 | X is Cl; $R^3$ is 5-pyrimidinyl; $R^4$ is H |
| C-31 | X is Cl; $R^3$ is 2-Me-5-pyrimidinyl; $R^4$ is H |
| C-32 | X is Cl; $R^3$ is 5-thiazolyl; $R^4$ is H |

-continued

| Table | Row Heading |
|---|---|
| C-33 | X is Cl; $R^3$ is 2-Me-5-thiazolyl; $R^4$ is H |
| C-34 | X is Cl; $R^3$ is 2-Cl-5-thiazolyl; $R^4$ is H |
| C-35 | X is Cl; $R^3$ is 2-Cl-5-thiazolyl; $R^4$ is Me |
| C-36 | X is Br; $R^3$ is 2-chloro-5-pyridinyl; $R^4$ is H |
| C-37 | X is Br; $R^3$ is 5-pyrimidinyl; $R^4$ is H |
| C-38 | X is Br; $R^3$ is 2-Me-5-pyrimidinyl; $R^4$ is H |
| C-39 | X is Br; $R^3$ is 5-thiazolyl; $R^4$ is H |
| C-40 | X is Br; $R^3$ is 2-Me-5-thiazolyl; $R^4$ is H |
| C-41 | X is Br; $R^3$ is 2-Cl-5-thiazolyl; $R^4$ is H |
| C-42 | X is Br; $R^3$ is 2-Cl-5-thiazolyl; $R^4$ is Me |

The invention claimed is:

1. A compound of Formula 2

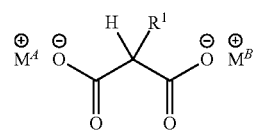

wherein $R^1$ is phenyl optionally substituted with Q and up to 3 substituents independently selected from $R^2$;

each $R^2$ is independently halogen, $C_1$-$C_4$ alkyl, $C_1$-$C_4$ haloalkyl, $C_1$-$C_4$ alkoxy or $C_1$-$C_4$ haloalkoxy;

Q is pyridinyl optionally substituted with up to 2 substituents independently selected from halogen and $C_1$-$C_4$ haloalkyl; and each $M^A$ and $M^B$ is independently Li, Na, K, $NH_4$, $NH(CH_2CH_3)_3$, $NH(CH_2CH_2CH_2CH_3)_3$, $NH_2(Bn)_2$, $NH_2(cyclohexyl)_2$ or $NH_2(phenyl)_2$.

2. A compound of claim 1 wherein $R^1$ is phenyl optionally substituted with up to 2 substituents independently selected from $R^2$;

each $R^2$ is independently halogen, $C_1$-$C_2$ alkyl, $C_1$-$C_2$ haloalkyl, $C_1$-$C_2$ alkoxy or $C_1$-$C_2$ haloalkoxy; and each $M^A$ and $M^B$ is independently Na, K, $NH_4$ or $NH(CH_2CH_3)_3$.

3. A compound of claim 2 wherein $R^1$ is phenyl substituted with 2 substituents selected from $R^2$ at the 3- and 5-positions;

each $R^2$ is independently Cl or —$CF_3$; and each $M^A$ and $M^B$ is independently Na, K or $NH_4$.

4. A compound of claim 2 wherein $R^1$ is phenyl substituted with 1 substituent selected from $R^2$ at the 3-position;

each $R^2$ is independently —$CF_3$ or —$OCF_3$; and each $M^A$ and $M^B$ is independently Na, K or $NH_4$.

5. A method for preparing a compound of Formula 1

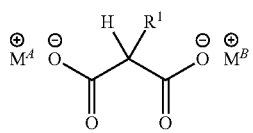

wherein $R^1$ is phenyl optionally substituted with Q and up to 3 substituents independently selected from $R^2$;

each $R^2$ is independently halogen, $C_1$-$C_4$ alkyl, $C_1$-$C_4$ haloalkyl, $C_1$-$C_4$ alkoxy or $C_1$-$C_4$ haloalkoxy;

Q is pyridinyl optionally substituted with up to 2 substituents independently selected from halogen and $C_1$-$C_4$ haloalkyl; and X is Cl or Br comprising contacting a compound of Formula 2

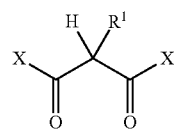

wherein $R^1$ is phenyl optionally substituted with Q and up to 3 substituents independently selected from $R^2$;

each $R^2$ is independently halogen, $C_1$-$C_4$ alkyl, $C_1$-$C_4$ haloalkyl, $C_1$-$C_4$ alkoxy or $C_1$-$C_4$ haloalkoxy;

Q is pyridinyl optionally substituted with up to 2 substituents independently selected from halogen and $C_1$-$C_4$ haloalkyl; and each $M^A$ and $M^B$ is independently Li, Na, K, $NH_4$, $NH(CH_2CH_3)_3$, $NH(CH_2CH_2CH_2CH_3)_3$, $NH_2(Bn)_2$, $NH_2(cyclohexyl)_2$ or $NH_2(phenyl)_2$, with a halogenating agent, wherein the halogenating agent is oxalyl chloride, thionyl chloride, phosgene, triphosgene, cyanuric chloride, phosphorous oxychloride, phosphorous trichloride, phosphorous pentachloride, diphosgene, sulfuryl chloride, thionyl bromide, triphenylphosphine dibromide or phosphorous tribromide.

6. The method of claim 5 wherein $R^1$ is phenyl optionally substituted with up to 2 substituents independently selected from $R^2$;

each $R^2$ is independently halogen, $C_1$-$C_2$ alkyl, $C_1$-$C_2$ haloalkyl, $C_1$-$C_2$ alkoxy or $C_1$-$C_2$ haloalkoxy; and each $M^A$ and $M^B$ independently Na, K, $NH_4$, $NH(CH_2CH_3)_3$ or $NH(C_2CH_2CH_2CH_3)_3$.

7. The method of claim 5 wherein the halogenating agent is oxalyl chloride, thionyl chloride, phosgene, triphosgene or cyanuric chloride; and X is Cl.

8. A method of preparing a compound of Formula 4

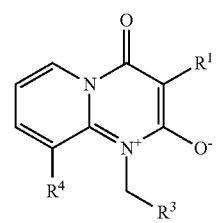

wherein $R^1$ is phenyl optionally substituted with Q and up to 3 substituents independently selected from $R^2$;

each $R^2$ is independently halogen, $C_1$-$C_4$ alkyl, $C_1$-$C_4$ haloalkyl, $C_1$-$C_4$ alkoxv or $C_1$-$C_4$ haloalkoxy;

Q is pyridinyl optionally substituted with up to 2 substituents independently selected from halogen and $C_1$-$C_4$ haloalkyl;

R³ is thiazolyl or pyrimidinyl, each optionally substituted with halogen or $C_1$-$C_2$ alkyl; and R⁴ is H or $C_1$-$C_4$ alkyl;

comprising preparing a compound of Formula 1

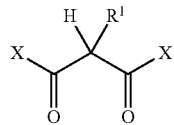

1 wherein

R¹ is phenyl optionally substituted with Q and up to 3 substituents independently selected from R²;

each R² is independently halogen, $C_1$-$C_4$ alkyl, $C_1$-$C_4$ haloalkyl, $C_1$-$C_4$ alkoxy or $C_1$-$C_4$ haloalkoxy;

Q is pyridinyl optionally substituted with up to 2 substituents independently selected from halogen and $C_1$-$C_4$ haloalkyl; and X is Cl or Br by contacting a compound of Formula 2

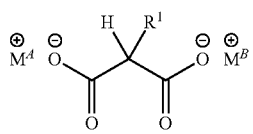

2 wherein

R¹ is phenyl optionally substituted with Q and up to 3 substituents independently selected from R²;

each R² is independently halogen, $C_1$-$C_4$ alkyl, $C_1$-$C_4$ haloalkyl, $C_1$-$C_4$ alkoxy or $C_1$-$C_4$ haloalkoxy;

Q is pyridinyl optionally substituted with up to 2 substituents independently selected from halogen and $C_1$-$C_4$ haloalkyl; and each $M^A$ and $M^B$ is independently Li, Na, K, NH₄, NH(CH₂CH₃)₃, NH(CH₂CH₂CH₂CH₃)₃, NH₂(Bn)₂, NH₂(cyclohexyl)₂ or NH₂(phenyl)₂;

with a halogenating agent wherein the halogenating agent is oxalyl chloride, thionyl chloride, phosgene, triphosgene, cyanuric chloride, phosphorous oxychloride, phosphorous trichloride, phosphorous pentachloride, diphosgene, sulfuryl chloride, thionyl bromide, triphenylphosphine dibromide or phosphorous tribromide;

to produce a compound of Formula 1; and reacting a compound of Formula 5

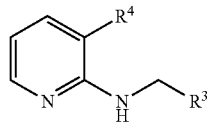

5 wherein

R³ is thiazolyl or pyrimidinyl, each optionally substituted with halogen or $C_1$-$C_2$ alkyl; and R⁴ is H or $C_1$-$C_4$ alkyl;

with the compound of Formula 1 to prepare the compound of Formula 4.

9. The method of claim 8 wherein

R¹ is phenyl optionally substituted with up to 2 substituents independently selected from R²;

each R² is independently Cl or —CF₃;

R³ is 2-chloro-5-thiazolyl;

R⁴ is CH₃; and each $M^A$ and $M^B$ is independently Na, K, NH₄, NH(CH₂CH₃)₃.

10. The method of claim 8 wherein

R¹ is phenyl substituted with 1 substituent selected from R²;

each R² is independently —CF₃ or —OCF₃;

R³ is 5-pyrimidinyl; and

R⁴ is H; and each $M^A$ and $M^B$ is independently Na, K or NH₄.

11. The method of claim 5 wherein the contacting is performed in an aprotic organic solvent.

12. The method of claim 11 wherein the aprotic organic solvent is toluene, dichloromethane, cyclohexane, benzene, 1,2-dichloroethane, ethyl acetate, butyl acetate or a combination of any of the foregoing.

13. The method of claim 5 wherein the contacting is performed in the presence of pyridine or a compound of Formula 3

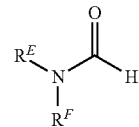

3 wherein $R^E$ is $C_1$-$C_4$ alkyl;

$R^F$ is $C_1$-$C_4$ alkyl; or $R^E$ and $R^F$ are taken together as $C_4$-$C_6$ alkylene.

* * * * *